(12) United States Patent
Kanno et al.

(10) Patent No.: US 9,290,623 B2
(45) Date of Patent: Mar. 22, 2016

(54) COMPOSITION FOR FORMING SILICON-CONTAINING RESIST UNDERLAYER FILM HAVING CYCLIC DIESTER GROUP

(71) Applicant: NISSAN CHEMICAL INDUSTRIES, LTD., Tokyo (JP)

(72) Inventors: Yuta Kanno, Toyama (JP); Daisuke Sakuma, Funabashi (JP); Kenji Takase, Toyama (JP); Makoto Nakajima, Toyama (JP); Shuhei Shigaki, Toyama (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/654,254

(22) PCT Filed: Dec. 17, 2013

(86) PCT No.: PCT/JP2013/083740
§ 371 (c)(1),
(2) Date: Jun. 19, 2015

(87) PCT Pub. No.: WO2014/098076
PCT Pub. Date: Jun. 26, 2014

(65) Prior Publication Data
US 2015/0322212 A1   Nov. 12, 2015

(30) Foreign Application Priority Data

Dec. 19, 2012  (JP) .................. 2012-276780

(51) Int. Cl.
*G03F 7/11*  (2006.01)
*C08G 77/18*  (2006.01)
(Continued)

(52) U.S. Cl.
CPC .............. *C08G 77/18* (2013.01); *C07F 7/1836* (2013.01); *C08G 77/14* (2013.01); *C08G 77/26* (2013.01);
(Continued)

(58) Field of Classification Search
CPC ........................................... C07F 7/1836
See application file for complete search history.

(56) References Cited

U.S. PATENT DOCUMENTS

| | | | |
|---|---|---|---|
| 2008/0171802 A1* | 7/2008 | Richard ................ | A61K 8/585 523/105 |
| 2010/0062368 A1* | 3/2010 | DiPietro et al. ......... | C08F 12/20 430/285.1 |
| 2012/0080404 A1* | 4/2012 | Lee et al. ............ | B81C 1/00031 216/37 |

FOREIGN PATENT DOCUMENTS

| | | |
|---|---|---|
| JP | 2004-310019 A | 11/2004 |
| JP | 2007-226170 A | 9/2007 |

(Continued)

OTHER PUBLICATIONS

Mar. 4, 2014 Written Opinion issued in International Patent Application No. PCT/JP2013/083740.
(Continued)

*Primary Examiner* — Cynthia Hamilton
(74) *Attorney, Agent, or Firm* — Oliff PLC

(57) ABSTRACT

A resist underlayer film that can be used as a hardmask. A resist underlayer film forming composition for lithography, includes: as a silane, a hydrolyzable silane, a hydrolysis product thereof, or a hydrolysis-condensation product thereof, wherein the hydrolyzable silane includes a hydrolyzable silane of Formula (1) or a hydrolyzable silane containing a combination of a hydrolyzable silane of Formula (1) with a hydrolyzable silane of Formula (2) in a content of less than 50% by mole in all silanes;
Formula (1): $R^1_a R^2_b Si(R^3)_{4-(a+b)}$ wherein $R^1$ is an organic group containing Formula (1-1), Formula (1-2), or Formula (1-3):

Formula (1-1)

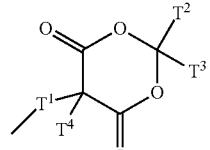

Formula (1-2)

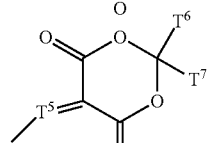

Formula (1-3)

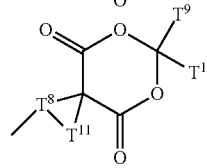

a is 1 and b is an integer of 0 to 2, where a+b is an integer of 1 to 3;
Formula (2): $R^4_a R^5_b Si(R^6)_{4-(a+b)}$ wherein, $R^4$ is an organic group containing Formula (2-1), Formula (2-2), or Formula (2-3):

Formula (2-1)

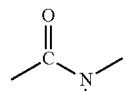

Formula (2-2)

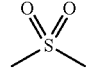

Formula (2-3)

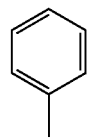

a is 1 and b is an integer of 0 to 2, where a+b is an integer of 1 to 3.

15 Claims, 4 Drawing Sheets

(51) Int. Cl.
*C07F 7/18* (2006.01)
*H01L 21/308* (2006.01)
*H01L 21/311* (2006.01)
*G03F 7/075* (2006.01)
*C08G 77/14* (2006.01)
*C08G 77/26* (2006.01)
*C08G 77/28* (2006.01)
*G03F 7/26* (2006.01)

(52) U.S. Cl.
CPC .............. *C08G 77/28* (2013.01); *G03F 7/0752* (2013.01); *G03F 7/11* (2013.01); *G03F 7/26* (2013.01); *H01L 21/3081* (2013.01); *H01L 21/3086* (2013.01); *H01L 21/31133* (2013.01); *H01L 21/31144* (2013.01)

(56) References Cited

FOREIGN PATENT DOCUMENTS

| | | |
|---|---|---|
| JP | 2009-244722 A | 10/2009 |
| JP | 2009-282524 A | 12/2009 |
| JP | 2010-085878 A | 4/2010 |
| JP | 2010-085912 A | 4/2010 |
| WO | 2006/057782 A1 | 6/2006 |
| WO | 2011/033965 A1 | 3/2011 |
| WO | 2011/102470 A1 | 8/2011 |

OTHER PUBLICATIONS

Francis M. Houlihan. "Advances in Resist Technology and Processing XVII," Proceedings of SPIE, The International Society for Optical Engineering, vol. 3999, pp. 330-334, 357-364, 365-374, Mar. 1, 2000.

* cited by examiner

COMPOSITION FOR FORMING SILICON-CONTAINING RESIST UNDERLAYER FILM HAVING CYCLIC DIESTER GROUP

TECHNICAL FIELD

The present invention relates to a composition for forming an underlayer film between a substrate and a resist (for example, a photoresist and an electron beam resist) that are used in the production of semiconductor devices. More in detail, the present invention relates to a resist underlayer film forming composition for lithography for forming an underlayer film used for an underlayer of a photoresist in a lithography process of the production of semiconductor devices. In addition, the present invention relates to a forming method of a resist pattern using the underlayer film forming composition.

BACKGROUND ART

Conventionally, in the production of semiconductor devices, fine processing by lithography using a photoresist has been performed. The fine processing is a processing method for forming fine convexo-concave shapes corresponding to the following pattern on the surface of a substrate by: forming a thin film of a photoresist on a semiconductor substrate such as a silicon wafer; irradiating the resultant thin film with active rays such as ultraviolet rays through a mask pattern in which a pattern of a semiconductor device is depicted; developing the thin film; and subjecting the substrate to etching processing using the resultant photoresist pattern as a protecting film.

However, recently, high integration of semiconductor devices has progressed and the adopted active rays tend to have a shorter wavelength, such as an ArF excimer laser (193 nm), replacing a KrF excimer laser (248 nm). Following such a tendency, the influence of reflection of active rays on a semiconductor substrate has become a large issue.

As an underlayer film between the semiconductor substrate and the photoresist, the use of a film known as a hardmask containing a metal element such as silicon or titanium has been performed. In this case, the resist and the hardmask have components largely differ from each other, so that the removal rates of the resist and the hardmask by dry etching largely depend on the type of a gas used for dry etching. By appropriately selecting the type of a gas, the hardmask can be removed by dry etching without a large decrease in the film thickness of the photoresist.

As described above, in the production of semiconductor devices in recent years, for achieving various effects such as the reflection preventing effect, a resist underlayer film has become disposed between the semiconductor substrate and the photoresist. The studies of a composition for a resist underlayer film have been performed; however, due to the diversity of characteristics required for the composition and so on, development of a novel material for the resist underlayer film is desired.

For example, a resist underlayer film containing a polysiloxane using a silane having an ester bond is described (see Patent Document 1, Patent Document 2, and Patent Document 3).

PRIOR ART DOCUMENTS

Patent Documents

Patent Document 1: Japanese Patent Application Publication No. 2007-226170 (JP 2007-226170 A)

Patent Document 2: Japanese Patent Application Publication No. 2004-310019 (JP 2004-310019 A)

Patent Document 3: International Publication No. WO 2006/057782 pamphlet

SUMMARY OF THE INVENTION

Problem to be Solved by the Invention

It is an object of the present invention to provide a resist underlayer film forming composition for lithography usable in the production of semiconductor devices. More in detail, it is an object of the present invention to provide a resist underlayer film forming composition for lithography for forming a resist underlayer film usable as a hardmask. In addition, it is an object of the present invention to provide a resist underlayer film forming composition for lithography for forming a resist underlayer film usable as an anti-reflective coating. Furthermore, it is an object of the present invention to provide a resist underlayer film for lithography causing no intermixing with a resist and having a dry etching rate higher than that of the resist, and a resist underlayer film forming composition for forming the underlayer film.

In particular, it is an object of the present invention to provide a resist underlayer film forming composition for forming a resist underlayer film capable of forming an excellent resist pattern shape when a resist as an upper layer of the resist underlayer film is exposed to light and the resist is developed with an alkaline developer or an organic solvent, and capable of transferring a rectangular resist pattern to an underlayer of the resist underlayer film by dry etching in a post-process.

Means for Solving the Problem

The present invention relates to, according to a first aspect, a resist underlayer film forming composition for lithography, comprising: as a silane, a hydrolyzable silane, a hydrolysis product thereof, or a hydrolysis-condensation product thereof, in which the hydrolyzable silane includes a hydrolyzable silane of Formula (1) or a hydrolyzable silane containing a combination of a hydrolyzable silane of Formula (1) with a hydrolyzable silane of Formula (2), and a hydrolyzable silane of Formula (1) or a hydrolyzable silane containing a combination of a hydrolyzable silane of Formula (1) with a hydrolyzable silane of Formula (2) is contained in a content of less than 50% by mole in all silanes, Formula (1):

$$R^1_a R^2_b Si(R^3)_{4-(a+b)} \quad \text{Formula (1)}$$

[in Formula (1), $R^1$ is an organic group containing Formula (1-1), Formula (1-2), or Formula (1-3):

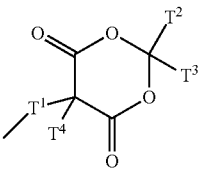

Formula (1-1)

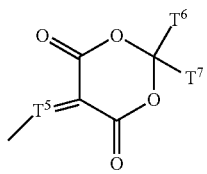

Formula (1-2)

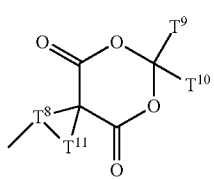

Formula (1-3)

(in Formula (1-1), Formula (1-2), and Formula (1-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups and atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is independently a hydrogen atom, an alkyl group, an alkenyl group, or a hydrolyzable silyl group bonded optionally through an alkylene group; and $T^{11}$ is an alkylene group) and is bonded to a silicon atom through a Si—C bond; $R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond; $R^3$ is an alkoxy group, an acyloxy group, or a halogen group; and a is an integer of 1 and b is an integer of 0 to 2, where a+b is an integer of 1 to 3], Formula (2):

$R^4_a R^5_b Si(R^6)_{4-(a+b)}$   Formula (2)

[in Formula (2), $R^4$ is an organic group containing Formula (2-1), Formula (2-2), or Formula (2-3):

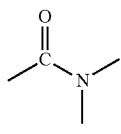

Formula (2-1)

Formula (2-2)

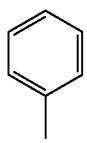

Formula (2-3)

and is bonded to a silicon atom through a Si—C bond; $R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond; $R^6$ is an alkoxy group, an acyloxy group, or a halogen group; and a is an integer of 1 and b is an integer of 0 to 2, where a+b is an integer of 1 to 3];

according to a second aspect, the resist underlayer film forming composition according to the first aspect, in which the hydrolyzable silane of Formula (1) or the hydrolyzable silane containing a combination of a hydrolyzable silane of Formula (1) with a hydrolyzable silane of Formula (2) is contained in a content of 5 to 45% by mole in all silanes;

according to a third aspect, the resist underlayer film forming composition according to the first aspect or the second aspect, in which a hydrolyzable silane of Formula (2) is a hydrolyzable silane in which $R^4$ is an organic group containing a group of Formula (2-1), a hydrolyzable silane in which $R^4$ is an organic group containing a group of Formula (2-2), a hydrolyzable silane in which $R^4$ is an organic group containing a group of Formula (2-3), or a mixture of these hydrolyzable silanes;

according to a fourth aspect, the resist underlayer film forming composition according to any one of the first aspect to the third aspect, in which a hydrolyzable silane containing a combination of a hydrolyzable silane of Formula (1) with a hydrolyzable silane of Formula (2) contains a hydrolyzable silane of Formula (1) and a hydrolyzable silane of Formula (2) in a molar ratio of 1:0.01 to 10;

according to a fifth aspect, the resist underlayer film forming composition for lithography according to any one of the first aspect to the fourth aspect, in which the hydrolyzable silane contains a hydrolyzable silane of Formula (1) or a hydrolyzable silane containing a combination of a hydrolyzable silane of Formula (1) with a hydrolyzable silane of Formula (2), and further a hydrolyzable silane of Formula (3):

$R^7_a R^8_b Si(R^9)_{4-(a+b)}$   Formula (3)

(in Formula (3), $R^7$ is an organic group containing Formula (3-1), Formula (3-2), Formula (3-3), Formula (3-4), Formula (3-5), or Formula (3-6):

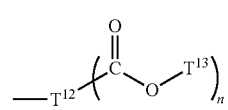

Formula (3-1)

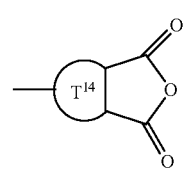

Formula (3-2)

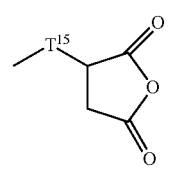

Formula (3-3)

Formula (3-4)

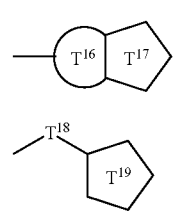

Formula (3-5)

-continued

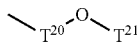

Formula (3-6)

(in Formula (3-1), Formula (3-2), Formula (3-3), Formula (3-4), Formula (3-5), and Formula (3-6), each of $T^{12}$, $T^{15}$, $T^{18}$, and $T^{20}$ is an alkylene group, a cyclic alkylene group, an alkenylene group, an arylene group, a sulfur atom, an oxygen atom, an oxycarbonyl group, an amido group, a secondary amino group, or a combination of these groups or atoms; $T^{13}$ is an alkyl group; each of $T^{14}$ and $T^{16}$ is an aliphatic ring or an aromatic ring; each of $T^{17}$ and $T^{19}$ is a lactone ring; $T^{21}$ is a $C_{1-10}$ alkyl group, a $C_{6-20}$ aryl group, a $C_{2-10}$ alkenyl group, or a group containing a $C_{1-10}$ alkylene group, a $C_{6-20}$ arylene group, an ether group, an ester group, a sulfide group, a carbonyl group, or a combination of these groups; and n is an integer of 1 or 2), and is bonded to a silicon atom through a Si—C bond; $R^8$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond; $R^9$ is an alkoxy group, an acyloxy group, or a halogen group; and a is an integer of 1 and b is an integer of 0 to 2, where a+b is an integer of 1 to 3];

according to a sixth aspect, the resist underlayer film forming composition according to the fifth aspect, comprising a hydrolyzable silane of Formula (1) and a hydrolyzable silane of Formula (2) and a hydrolyzable silane of Formula (3) in a molar ratio of 1:0 to 10:0.01 to 10;

according to a seventh aspect, the resist underlayer film forming composition for lithography according to any one of the first aspect to the sixth aspect, in which the hydrolyzable silane contains a hydrolyzable silane of Formula (1), a combination of a hydrolyzable silane of Formula (1) with a hydrolyzable silane of Formula (2), a combination of a hydrolyzable silane of Formula (1) with a hydrolyzable silane of Formula (3), or a combination of a hydrolyzable silane of Formula (1) and a hydrolyzable silane of Formula (2) and a hydrolyzable silane of Formula (3), and a still other hydrolyzable silane, and the other hydrolyzable silane is at least one organic silicon compound selected from the group consisting of Formula (4) and Formula (5):

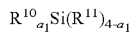   Formula (4)

(in Formula (4), $R^{10}$ is an alkyl group, an aryl group, a halogenated alkyl group, a halogenated aryl group, an alkenyl group, or an organic group having an epoxy group, an acryloyl group, a methacryloyl group, a mercapto group, or a cyano group and is bonded to a silicon atom through a Si—C bond; $R^{11}$ is an alkoxy group, an acyloxy group, or a halogen group; and $a_1$ is an integer of 0 to 3),

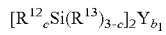   Formula (5)

(in Formula (5), $R^{12}$ is an alkyl group and is bonded to a silicon atom through a Si—C bond; $R^{13}$ is an alkoxy group, an acyloxy group, or a halogen group; Y is an alkylene group or an arylene group; $b_1$ is an integer of 0 or 1; and c is an integer of 0 or 1);

according to an eighth aspect, a resist underlayer film forming composition, comprising: a hydrolysis product of a hydrolyzable silane of Formula (1) and a hydrolyzable silane of Formula (2) as described in any one of the first aspect to the seventh aspect and a hydrolyzable silane of Formula (4) as described in the seventh aspect, as a polymer;

according to a ninth aspect, a resist underlayer film forming composition, comprising: a hydrolysis product of a hydrolyzable silane of Formula (1) and a hydrolyzable silane of Formula (2) as described in any one of the first aspect to the seventh aspect, a hydrolyzable silane of Formula (3) as described in any one of the fifth aspect to the seventh aspect, and a hydrolyzable silane of Formula (4) as described in the seventh aspect, as a polymer;

according to a tenth aspect, the resist underlayer film forming composition according to any one of the first aspect to the ninth aspect, further comprising an acid as a hydrolysis catalyst;

according to an eleventh aspect, the resist underlayer film forming composition according to any one of the first aspect to the tenth aspect, further comprising water;

according to a twelfth aspect, a resist underlayer film obtained by applying the resist underlayer film forming composition as described in any one of the first aspect to the eleventh aspect onto a semiconductor substrate and baking the composition;

according to a thirteenth aspect, a method for producing a semiconductor device, the method comprising: applying the resist underlayer film forming composition as described in any one of the first aspect to the eleventh aspect onto a semiconductor substrate and baking the composition to form a resist underlayer film; applying a composition for a resist onto the underlayer film to form a resist film; exposing the resist film to light; developing the resist after the exposure to obtain a resist pattern; etching the resist underlayer film using the resist pattern; and processing the semiconductor substrate using the patterned resist and the patterned resist underlayer film;

according to a fourteenth aspect, a method for producing a semiconductor device, the method comprising: forming an organic underlayer film on a semiconductor substrate; applying the resist underlayer film forming composition as described in any one of the first aspect to the eleventh aspect onto the organic underlayer film and baking the composition to form a resist underlayer film; applying a composition for a resist onto the resist underlayer film to form a resist film; exposing the resist film to light; developing the resist after the exposure to obtain a resist pattern; etching the resist underlayer film using the resist pattern; etching the organic underlayer film using the patterned resist underlayer film; and processing the semiconductor substrate using the patterned organic underlayer film; and according to a fifteenth aspect, a silane compound of Formula (A):

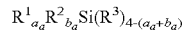   Formula (A)

[in Formula (A), $R^1$ is an organic group containing Formula (A-1), Formula (A-2), or Formula (A-3):

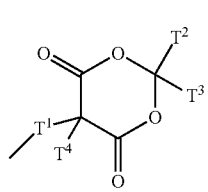

Formula (A-1)

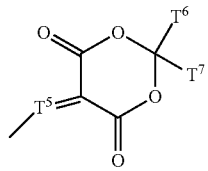

Formula (A-2)

-continued

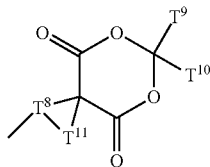

Formula (A-3)

(in Formula (A-1), Formula (A-2), or Formula (A-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups or atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is independently a hydrogen atom, an alkyl group, an alkenyl group, or a hydrolyzable silyl group bonded optionally through an alkylene group; and $T^{11}$ is an alkylene group) and is bonded to a silicon atom through a Si—C bond; $R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond; $R^3$ is an alkoxy group, an acyloxy group, or a halogen group; $a_a$ is an integer of 1 and $b_a$ is an integer of 0 or 1, where $a_a+b_a$ is an integer of 1 or 2].

Effects of the Invention

In the present invention, the substrate is coated in such an order that the substrate is coated with the resist underlayer film (containing an inorganic silicon-based compound) of the present invention either with or without an organic underlayer film interposed therebetween, and then the resist underlayer film is coated with a resist film (an organic resist film)

Then, the resist underlayer film of the present invention functions as a hardmask, and a hydrolyzable group such as an alkoxy group, an acyloxy group, and a halogen group in the structure of a hydrolyzable silane of Formula (1) is hydrolyzed or partially hydrolyzed and then, the resultant silanol group is subjected to a condensation reaction to form a polymer having a polysiloxane structure. The polyorganosiloxane structure (intermediate film) is effective as a hardmask for etching an organic underlayer film existing as an underlayer of the intermediate film or for processing (etching) the substrate. That is, the intermediate film has satisfactory dry etching resistance during the substrate processing or against an oxygen-based dry etching gas for etching the organic underlayer film.

These bonding moieties contained in the polyorganosiloxane have a carbon-nitrogen bond or a carbon-oxygen bond, so that the bonding moieties have a dry etching rate by using a halogen-based gas higher than that of a carbon-carbon bond and then, are effective upon transferring a pattern of the upper layer resist to the resist underlayer film.

Thus, a resist underlayer film formed from the composition of the present invention possesses properties of enhancing the dry etching rate of the resist underlayer film relative to the upper layer resist and dry etching resistance of the resist underlayer film during the substrate processing or the like.

Accordingly, by using as a hardmask, a polyorganosiloxane produced from a hydrolysis product of a hydrolyzable silane of Formula (1) having a Meldrum's acid group or a hydrolyzable silane containing a combination of a hydrolyzable silane of Formula (1) with a hydrolyzable silane of Formula (2) or a hydrolyzable silane containing further a combination of these hydrolyzable silanes with a hydrolyzable silane of Formula (3), where these hydrolyzable silanes are contained in the composition of the present invention, when the upper layer resist is exposed to light and is developed with an alkaline developer or an organic solvent, an excellent resist pattern shape can be formed and a rectangular resist pattern can be transferred to an underlayer by dry etching in a post-process.

MODES FOR CARRYING OUT THE INVENTION

Figure 1:
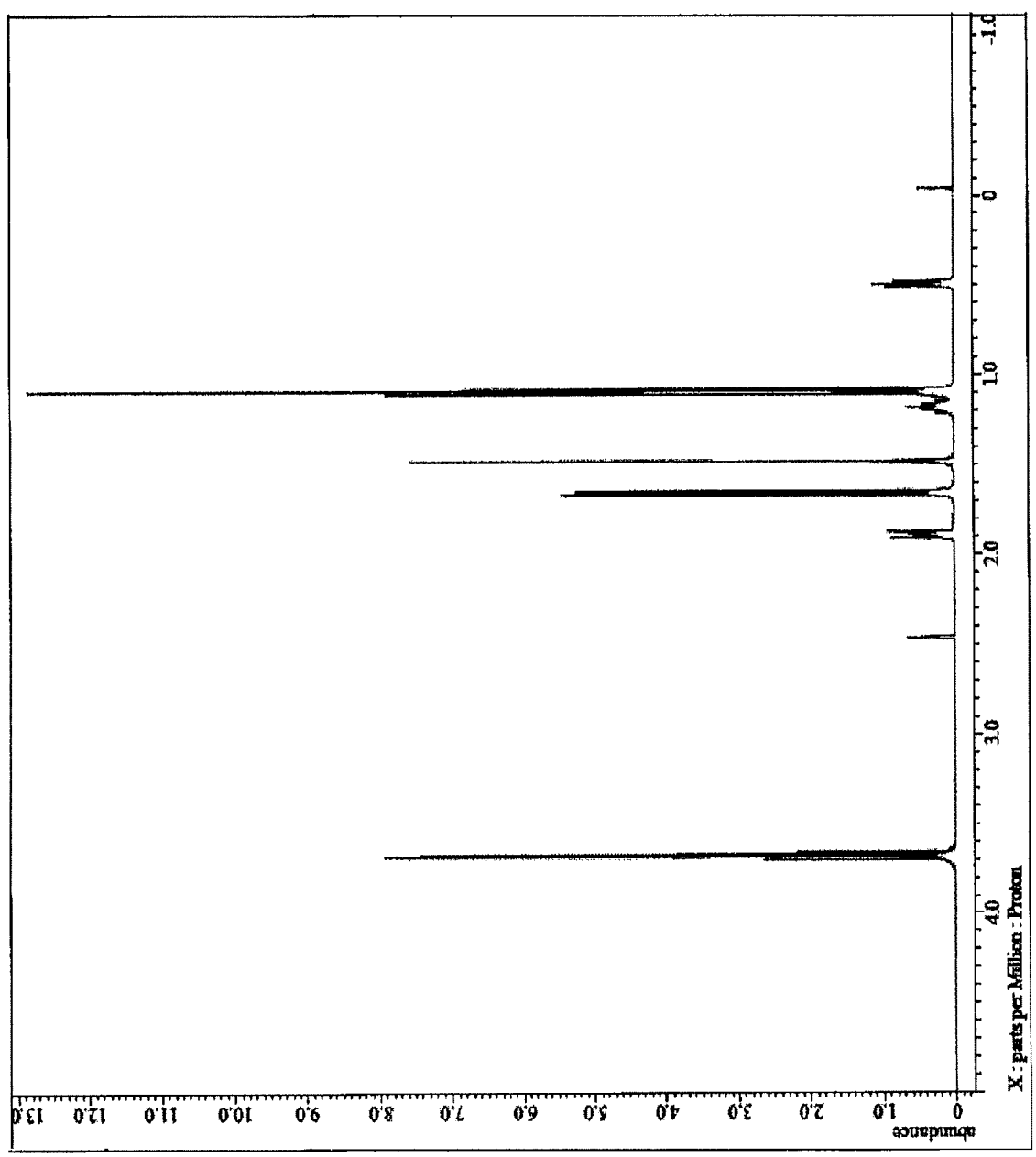
FIG. 1 shows an NMR spectrum of a compound 1.

The present invention provides a resist underlayer film forming composition for lithography characterized by containing as a silane, a hydrolyzable silane, a hydrolysis product thereof, or a hydrolysis-condensation product thereof, characterized in that the silane includes a hydrolyzable silane of Formula (1) or a hydrolyzable silane containing a combination of a hydrolyzable silane of Formula (1) with a hydrolyzable silane of Formula (2), and a content of a hydrolyzable silane of Formula (1) or a hydrolyzable silane containing a combination of a hydrolyzable silane of Formula (1) with a hydrolyzable silane of Formula (2) is less than 50% by mole in all silanes. The present invention is also a novel silane compound of Formula (A) and the silane compound of Formula (A) has the same structure as that of the hydrolyzable silane compound of Formula (1).

The hydrolyzable silane of Formula (1) or the hydrolyzable silane containing a combination of a hydrolyzable silane of Formula (1) with a hydrolyzable silane of Formula (2) may be used in the composition of the present invention in a content in a range of less than 50% by mole, or 5 to 45% by mole, or 5 to 40% by mole, or 5 to 35% by mole, or 5 to 30% by mole, or 10 to 20% by mole in all silanes.

The resist underlayer film forming composition of the present invention contains a hydrolyzable silane of Formula (1) or a hydrolyzable silane of a combination of a hydrolyzable silane of Formula (1) with a hydrolyzable silane of Formula (2), a hydrolysis product thereof, or a hydrolysis-condensation product thereof, and a solvent. In addition, the composition may contain as optional components, an acid, water, an alcohol, a curing catalyst, an acid generator, other organic polymers, a light absorptive compound, a surfactant, or the like.

The solid content in the resist underlayer film forming composition of the present invention is, for example, 0.1 to 50% by mass, 0.1 to 30% by mass, or 0.1 to 25% by mass. Here, the solid content is a component remaining after removing a solvent component from all components of the resist underlayer film forming composition.

The content of a hydrolyzable silane, a hydrolysis product thereof, or a hydrolysis-condensation product thereof in the solid content is 20% by mass or more, for example, 50 to 100% by mass, 60 to 100% by mass, or 70 to 100% by mass.

Then, the hydrolyzable silane, the hydrolysis product thereof, and the hydrolysis-condensation product thereof may also be used as a mixture thereof. The hydrolyzable silane is hydrolyzed and the resultant hydrolysis product thereof is subjected to condensation to produce the hydrolysis-condensation product thereof which may be used in the composition. When the hydrolysis-condensation product is obtained, a partially-hydrolyzed product produced by incomplete hydrolysis and a silane compound are mixed in the hydrolysis-condensation product and such a mixture may also be used in the composition. The condensation product is a polymer having a polysiloxane structure. The polysiloxane contains a hydrolysis product of a hydrolyzable silane of Formula (1) or a hydrolyzable silane containing a combination of a hydrolyzable silane of Formula (1) with a hydrolyzable silane of Formula (2). To a hydrolysis-condensation product (polysiloxane) of a hydrolysis product of a hydrolyzable silane of Formula (1) or a hydrolyzable silane containing a combination of a hydrolyzable silane of Formula (1) with a hydrolyzable silane of Formula (2), a hydrolyzable silane of Formula (1) or a hydrolyzable silane containing a combination of a hydrolyzable silane of Formula (1) and a hydrolyzable silane of Formula (2) may be added.

To a hydrolysis-condensation product (polysiloxane) not containing a hydrolysis product of a hydrolyzable silane of Formula (1) or a hydrolyzable silane containing a combination of a hydrolyzable silane of Formula (1) with a hydrolyzable silane of Formula (2), a hydrolyzable silane of Formula (1) or a hydrolyzable silane containing a combination of a hydrolyzable silane of Formula (1) with a hydrolyzable silane of Formula (2) may be added.

In a hydrolyzable silane of Formula (1) used in the present invention, $R^1$ is an organic group containing a group of Formula (1-1), Formula (1-2), or Formula (1-3) and is bonded to a silicon atom through a Si—C bond. $R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond. $R^3$ is an alkoxy group, an acyloxy group, or a halogen group. a is an integer of 1 and b is an integer of 0 or 1, where a+b is an integer of 1 or 2. Further, a is an integer of 1 and b is an integer of 0 to 2, where a+b is an integer of 1 to 3.

In a group of Formula (1-1), Formula (1-2), or Formula (1-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups and atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is a hydrogen atom, an alkyl group, an alkenyl group, or a hydrolyzable silyl group bonded optionally through an alkylene group; and $T^{11}$ is an alkylene group.

Examples of the alkylene group capable of being used for $T^2$, $T^3$, $T^4$, $T^6$, $T^7$, $T^9$, and $T^{10}$ include the below-described alkylene groups and the hydrolyzable silyl group is a group in which 1 to 3, preferably 3 hydrolyzable group(s) containing an alkoxy group, an acyloxy group, or a halogen group is(are) bonded to a silicon atom. Examples of these hydrolyzable groups include the below-described hydrolyzable groups.

The hydrolyzable silane of Formula (1) may be a hydrolyzable silane in which $R^1$ contains an organic group containing a group of Formula (1-1), a hydrolyzable silane in which $R^1$ contains an organic group containing a group of Formula (1-2), a hydrolyzable silane in which $R^1$ contains an organic group containing a group of Formula (1-3), or a mixture of these hydrolyzable silanes.

In a hydrolyzable silane of Formula (2) used in the present invention, $R^4$ is an organic group containing a group of Formula (2-1), Formula (2-2), or Formula (2-3) and is bonded to a silicon atom through a Si—C bond. $R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond. $R^6$ is an alkoxy group, an acyloxy group, or a halogen group. a is an integer of 1 and b is an integer of 0 or 1, where a+b is an integer of 1 or 2. Further, a is an integer of 1 and b is an integer of 0 to 2, where a+b is an integer of 1 to 3.

The hydrolyzable silane of Formula (2) may be a hydrolyzable silane in which $R^4$ contains an organic group containing a group of Formula (2-1), a hydrolyzable silane in which $R^4$ contains an organic group containing a group of Formula (2-2), a hydrolyzable silane in which $R^4$ contains an organic group containing a group of Formula (2-3), or a mixture of these hydrolyzable silanes.

The resist underlayer film forming composition for lithography of the present invention may contain a hydrolyzable silane of Formula (1) and a hydrolyzable silane of Formula (2) in a molar ratio of 1:0.01 to 10, or 1:0.1 to 10, or 1:0.1 to 5.

In the resist underlayer film forming composition for lithography of the present invention, the hydrolyzable silane contains a hydrolyzable silane of Formula (1) or a combination of a hydrolyzable silane of Formula (1) with a hydrolyzable silane of Formula (2), and further, a hydrolyzable silane of Formula (3). In the hydrolyzable silane of Formula (3), $R^7$ is an organic group containing a group of Formula (3-1), Formula (3-2), Formula (3-3), Formula (3-4), Formula (3-5), or Formula (3-6) and is bonded to a silicon atom through a Si—C bond. $R^8$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond. $R^9$ is an alkoxy group, an acyloxy group, or a halogen group. a is an integer of 1 and b is an integer of 0 or 1, where a+b is an integer of 1 or 2. Further, a is an integer of 1 and b is an integer of 0 to 2, where a+b is an integer of 1 to 3.

In a group of Formula (3-1), Formula (3-2), Formula (3-3), Formula (3-4), Formula (3-5), or Formula (3-6), each of $T^{12}$, $T^{15}$, and $T^{18}$ is an alkylene group, a cyclic alkylene group, an alkenylene group, an arylene group, a sulfur atom, an oxygen atom, an oxycarbonyl group, an amido group, a secondary amino group, or a combination of these groups and atoms; $T^{13}$ is an alkyl group; each of $T^{14}$ and $T^{16}$ is an aliphatic ring or an aromatic ring; each of $T^{17}$ and $T^{19}$ is a lactone ring; $T^{21}$ is a $C_{1-10}$ alkyl group, a $C_{6-20}$ aryl group, a $C_{2-10}$ alkenyl group, or a group containing a $C_{1-10}$ alkylene group, a $C_{6-20}$ arylene group, an ether group, an ester group, a sulfide group, a carbonyl group, or a combination of these groups. n is an integer of 1 or 2.

In the present invention, a hydrolyzable silane of Formula (1) and a hydrolyzable silane of Formula (2) and a hydrolyzable silane of Formula (3) may be contained in a molar ratio of 1:0 to 10:0.01 to 10 or 1:0 to 10:0 to 10.

The alkyl group is a linear or branched alkyl group having a carbon atom number of 1 to 10 and examples of the alkyl group include a methyl group, an ethyl group, an n-propyl group, an isopropyl group, an n-butyl group, an isobutyl group, a sec-butyl group, a tert-butyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, and a 1-ethyl-2-methyl-n-propyl group.

As the alkyl group, a cyclic alkyl group may also be used and examples of a $C_{1-10}$ cyclic alkyl group include a cyclopropyl group, a cyclobutyl group, a 1-methyl-cyclopropyl group, a 2-methyl-cyclopropyl group, a cyclopentyl group, a 1-methyl-cyclobutyl group, a 2-methyl-cyclobutyl group, a 3-methyl-cyclobutyl group, a 1,2-dimethyl-cyclopropyl group, a 2,3-dimethyl-cyclopropyl group, a 1-ethyl-cyclopropyl group, a 2-ethyl-cyclopropyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-isopropyl-cyclopropyl group, a 2-isopropyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

Examples of the alkylene group include alkylene groups derived from the above alkyl groups. Examples of the alkylene group include a methylene group derived from a methyl group, an ethylene group derived from an ethyl group, a propylene group derived from a propyl group.

Examples of the alkenyl group include $C_{2-10}$ alkenyl groups such as an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethyl ethenyl group, a 1-methyl-1-propenyl group, a 1-methyl-2-propenyl group, a 1-pentenyl group, a 2-pentenyl group, a 3-pentenyl group, a 4-pentenyl group, a 1-n-propyl ethenyl group, a 1-methyl-1-butenyl group, a 1-methyl-2-butenyl group, a 1-methyl-3-butenyl group, a 2-ethyl-2-propenyl group, a 2-methyl-1-butenyl group, a 2-methyl-2-butenyl group, a 2-methyl-3-butenyl group, a 3-methyl-1-butenyl group, a 3-methyl-2-butenyl group, a 3-methyl-3-butenyl group, a 1,1-dimethyl-2-propenyl group, a 1-isopropyl ethenyl group, a 1,2-dimethyl-1-propenyl group, a 1,2-dimethyl-2-propenyl group, a 1-cyclopentenyl group, a 2-cyclopentenyl group, a 3-cyclopentenyl group, a 1-hexenyl group, a 2-hexenyl group, a 3-hexenyl group, a 4-hexenyl group, a 5-hexenyl group, a 1-methyl-1-pentenyl group, a 1-methyl-2-pentenyl group, a 1-methyl-3-pentenyl group, a 1-methyl-4-pentenyl group, a 1-n-butyl ethenyl group, a 2-methyl-1-pentenyl group, a 2-methyl-2-pentenyl group, a 2-methyl-3-pentenyl group, a 2-methyl-4-pentenyl group, a 2-n-propyl-2-propenyl group, a 3-methyl-1-pentenyl group, a 3-methyl-2-pentenyl group, a 3-methyl-3-pentenyl group, a 3-methyl-4-pentenyl group, a 3-ethyl-3-butenyl group, a 4-methyl-1-pentenyl group, a 4-methyl-2-pentenyl group, a 4-methyl-3-pentenyl group, a 4-methyl-4-pentenyl group, a 1,1-dimethyl-2-butenyl group, a 1,1-dimethyl-3-butenyl group, a 1,2-dimethyl-1-butenyl group, a 1,2-dimethyl-2-butenyl group, a 1,2-dimethyl-3-butenyl group, a 1-methyl-2-ethyl-2-propenyl group, a 1-sec-butyl ethenyl group, a 1,3-dimethyl-1-butenyl group, a 1,3-dimethyl-2-butenyl group, a 1,3-dimethyl-3-butenyl group, a 1-isobutyl ethenyl group, a 2,2-dimethyl-3-butenyl group, a 2,3-dimethyl-1-butenyl group, a 2,3-dimethyl-2-butenyl group, a 2,3-dimethyl-3-butenyl group, a 2-isopropyl-2-propenyl group, a 3,3-dimethyl-1-butenyl group, a 1-ethyl-1-butenyl group, a 1-ethyl-2-butenyl group, a 1-ethyl-3-butenyl group, a 1-n-propyl-1-propenyl group, a 1-n-propyl-2-propenyl group, a 2-ethyl-1-butenyl group, a 2-ethyl-2-butenyl group, a 2-ethyl-3-butenyl group, a 1,1,2-trimethyl-2-propenyl group, a 1-tert-butyl ethenyl group, a 1-methyl-1-ethyl-2-propenyl group, a 1-ethyl-2-methyl-1-propenyl group, a 1-ethyl-2-methyl-2-propenyl group, a 1-isopropyl-1-propenyl group, a 1-isopropyl-2-propenyl group, a 1-methyl-2-cyclopentenyl group, a 1-methyl-3-cyclopentenyl group, a 2-methyl-1-cyclopentenyl group, a 2-methyl-2-cyclopentenyl group, a 2-methyl-3-cyclopentenyl group, a 2-methyl-4-cyclopentenyl group, a 2-methyl-5-cyclopentenyl group, a 2-methylene-cyclopentyl group, a 3-methyl-1-cyclopentenyl group, a 3-methyl-2-cyclopentenyl group, a 3-methyl-3-cyclopentenyl group, a 3-methyl-4-cyclopentenyl group, a 3-methyl-5-cyclopentenyl group, a 3-methylene-cyclopentyl group, a 1-cyclohexenyl group, a 2-cyclohexenyl group, and a 3-cyclohexenyl group.

Examples of the alkenylene group include alkenylene groups derived from the above alkenyl groups.

Examples of the aryl group include $C_{6-20}$ aryl groups such as a phenyl group, an o-methylphenyl group, an m-methylphenyl group, a p-methylphenyl group, an o-chlorophenyl group, an m-chlorophenyl group, a p-chlorophenyl group, an o-fluorophenyl group, a p-mercaptophenyl group, an o-methoxyphenyl group, a p-methoxyphenyl group, a p-aminophenyl group, a p-cyanophenyl group, an α-naphthyl group, a β-naphthyl group, an o-biphenylyl group, an m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, and a 9-phenanthryl group.

Examples of the arylene group include arylene groups derived from the above aryl groups.

Examples of the above-exemplified groups also include organic groups in which the above-exemplified groups are substituted with a halogen atom such as a fluorine atom, a chlorine atom, a bromine atom, and an iodine atom.

By using a sulfur atom, a sulfide bond can be formed. By using an oxygen atom, an ether bond can be formed. By using an oxycarbonyl group, an ester bond can be formed. By using an amido group, an amide bond can be formed. By using a secondary amino group and a tertiary amino group, an amino group can be formed. By using these functional groups in combination with the above-exemplified groups, each bond can be formed.

Examples of the organic group having an epoxy group include glycidoxymethyl, glycidoxyethyl, glycidoxypropyl, glycidoxybutyl, and epoxycyclohexyl.

Examples of the organic group having an acryloyl group include acryloylmethyl, acryloylethyl, and acryloylpropyl.

Examples of the organic group having a methacryloyl group include methacryloylmethyl, methacryloylethyl, and methacryloylpropyl. Examples of the organic group having a mercapto group include ethylmercapto, butylmercapto, hexylmercapto, and octylmercapto.

Examples of the organic group having an amino group include aminomethyl, aminoethyl, and aminopropyl.

Examples of the organic group having a cyano group include cyanoethyl and cyanopropyl.

Examples of the alkylidine group include alkylidyne groups derived from the above alkyl groups such as a methylidine group, an ethylidine group, and a propylidine group. Examples of the alkanetriyl group include alkanetriyl groups derived from the above alkyl groups such as a methanetriyl group, an ethanetriyl group, and a propanetriyl group.

Examples of the alkoxy group include $C_{1-20}$ alkoxy groups having a linear, branched, or cyclic alkyl moiety, such as a methoxy group, an ethoxy group, an n-propoxy group, an isopropoxy group, an n-butoxy group, an isobutoxy group, a sec-butoxy group, a tert-butoxy group, an n-pentyloxy group, a 1-methyl-n-butoxy group, a 2-methyl-n-butoxy group, a 3-methyl-n-butoxy group, a 1,1-dimethyl-n-propoxy group, a 1,2-dimethyl-n-propoxy group, a 2,2-dimethyl-n-propoxy group, a 1-ethyl-n-propoxy group, an n-hexyloxy group, a 1-methyl-n-pentyloxy group, a 2-methyl-n-pentyloxy group, a 3-methyl-n-pentyloxy group, a 4-methyl-n-pentyloxy group, a 1,1-dimethyl-n-butoxy group, a 1,2-dimethyl-n-butoxy group, a 1,3-dimethyl-n-butoxy group, a 2,2-dimethyl-n-butoxy group, a 2,3-dimethyl-n-butoxy group, a 3,3-dimethyl-n-butoxy group, a 1-ethyl-n-butoxy group, a 2-ethyl-n-butoxy group, a 1,1,2-trimethyl-n-propoxy group, a 1,2,2-trimethyl-n-propoxy group, a 1-ethyl-1-methyl-n-propoxy group, and a 1-ethyl-2-methyl-n-propoxy group, and examples of the cyclic alkoxy group include a cyclopropoxy group, a cyclobutoxy group, a 1-methyl-cyclopropoxy group, a 2-methyl-cyclopropoxy group, a cyclopentyloxy group, a 1-methyl-cyclobutoxy group, a 2-methyl-cyclobutoxy group, a 3-methyl-cyclobutoxy group, a 1,2-dimethyl-cyclopropoxy group, a 2,3-dimethyl-cyclopropoxy group, a 1-ethyl-cyclopropoxy group, a 2-ethyl-cyclopropoxy group, a cyclohexyloxy group, a 1-methyl-cyclopentyloxy group, a 2-methyl-cyclopentyloxy group, a 3-methyl-cyclopentyloxy group, a 1-ethyl-cyclobutoxy group, a 2-ethyl-cyclobutoxy group, a 3-ethyl-cyclobutoxy group, a 1,2-dimethyl-cyclobutoxy group, a 1,3-dimethyl-cyclobutoxy group, a 2,2-dimethyl-cyclobutoxy group, a 2,3-dimethyl-cyclobutoxy group, a 2,4-dimethyl-cyclobutoxy group, a 3,3-dimethyl-cyclobutoxy group, a 1-n-propyl-cyclopropoxy group, a 2-n-propyl-cyclopropoxy group, a 1-isopropyl-cyclopropoxy group, a 2-isopropyl-cyclopropoxy group, a 1,2,2-trimethyl-cyclopropoxy group, a 1,2,3-trimethyl-cyclopropoxy group, a 2,2,3-trimethyl-cyclopropoxy group, a 1-ethyl-2-methyl-cyclopropoxy group, a 2-ethyl-1-methyl-cyclopropoxy group, a 2-ethyl-2-methyl-cyclopropoxy group, and a 2-ethyl-3-methyl-cyclopropoxy group.

Examples of the acyloxy group include $C_{2-20}$ acyloxy groups such as a methylcarbonyloxy group, an ethylcarbonyloxy group, an n-propylcarbonyloxy group, an isopropylcarbonyloxy group, an n-butylcarbonyloxy group, an isobutylcarbonyloxy group, a sec-butylcarbonyloxy group, a tert-butylcarbonyloxy group, an n-pentylcarbonyloxy group, a 1-methyl-n-butylcarbonyloxy group, a 2-methyl-n-butylcarbonyloxy group, a 3-methyl-n-butylcarbonyloxy group, a 1,1-dimethyl-n-propylcarbonyloxy group, a 1,2-dimethyl-n-propylcarbonyloxy group, a 2,2-dimethyl-n-propylcarbonyloxy group, a 1-ethyl-n-propylcarbonyloxy group, an n-hexylcarbonyloxy group, a 1-methyl-n-pentylcarbonyloxy group, a 2-methyl-n-pentylcarbonyloxy group, a 3-methyl-n-pentylcarbonyloxy group, a 4-methyl-n-pentylcarbonyloxy group, a 1,1-dimethyl-n-butylcarbonyloxy group, a 1,2-dimethyl-n-butylcarbonyloxy group, a 1,3-dimethyl-n-butylcarbonyloxy group, a 2,2-dimethyl-n-butylcarbonyloxy group, a 2,3-dimethyl-n-butylcarbonyloxy group, a 3,3-dimethyl-n-butylcarbonyloxy group, a 1-ethyl-n-butylcarbonyloxy group, a 2-ethyl-n-butylcarbonyloxy group, a 1,1,2-trimethyl-n-propylcarbonyloxy group, a 1,2,2-trimethyl-n-propylcarbonyloxy group, a 1-ethyl-1-methyl-n-propylcarbonyloxy group, a 1-ethyl-2-methyl-n-propylcarbonyloxy group, a phenylcarbonyloxy group, and a tosylcarbonyloxy group.

Examples of the halogen atom include a fluorine atom, a chlorine atom, a bromine atom, and an iodine atom.

Examples of the hydrolyzable silane of Formula (1) include compounds of Formulae below.

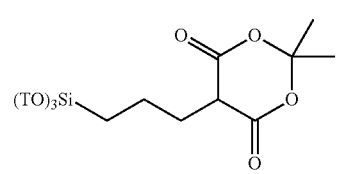

Formula (1-1-1)

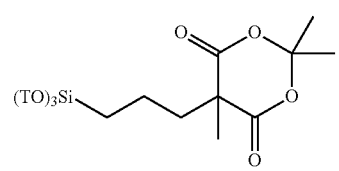

Formula (1-1-2)

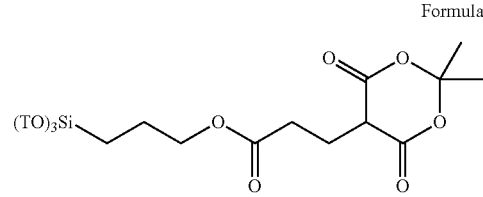

Formula (1-1-3)

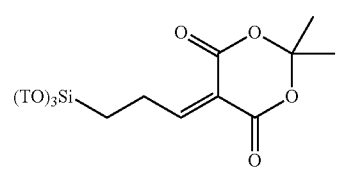

Formula (1-1-4)

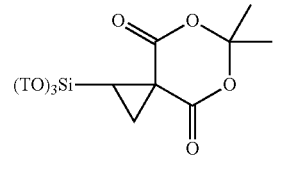

Formula (1-1-5)

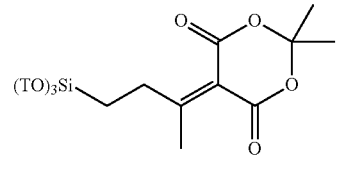

Formula (1-1-6)

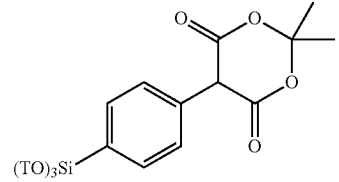

Formula (1-1-7)

-continued
Formula (1-1-8)
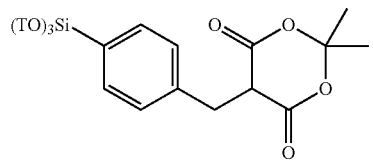
Formula (1-1-10)
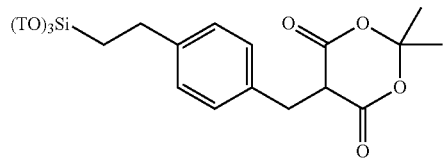
Formula (1-1-11)
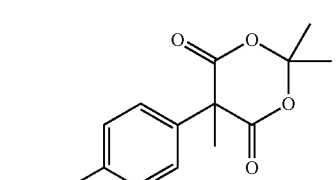
Formula (1-1-12)
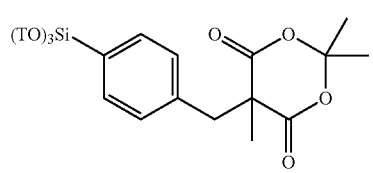
Formula (1-1-13)
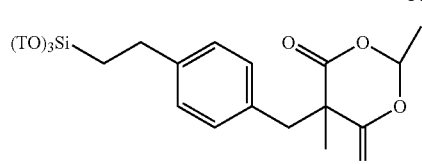
Formula (1-1-14)
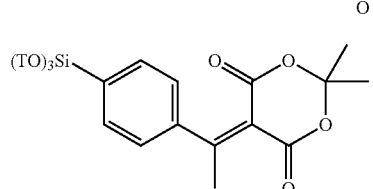
Formula (1-1-15)
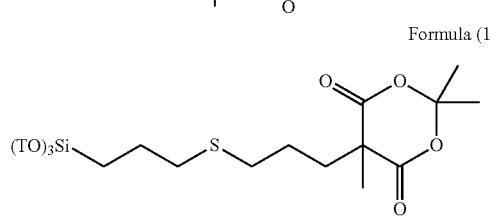
Formula (1-1-16)
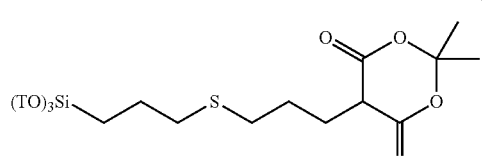
Formula (1-1-17)
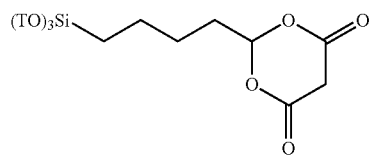
-continued
Formula (1-1-18)
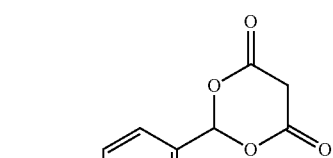
Formula (1-1-19)
Formula (1-1-20)
Formula (1-1-21)
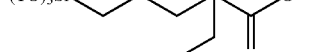
Formula (1-1-22)
Formula (1-1-23)
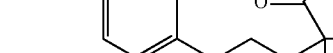
Formula (1-1-24)
Formula (1-1-25)

Formula (1-1-26)

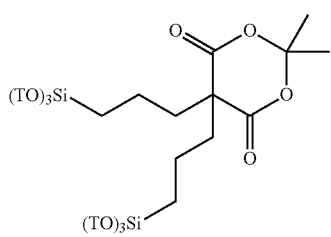

In the above formulae, T is an alkyl group and examples of the alkyl group include the above-exemplified alkyl groups and among them, a methyl group and an ethyl group are preferred.

Examples of the hydrolyzable silane of Formula (2) include compounds of Formulae below.

Formula (2-1-1)

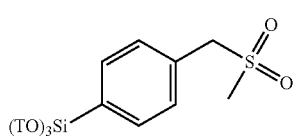

Formula (2-1-2)

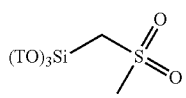

Formula (2-1-3)

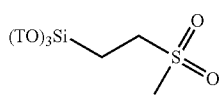

Formula (2-1-4)

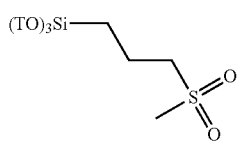

Formula (2-1-5)

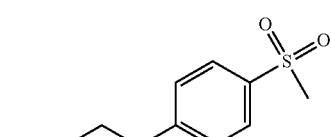

Formula (2-1-6)

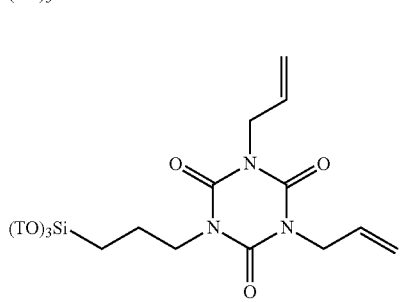

Formula (2-1-7)

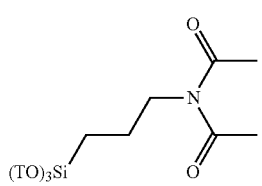

Formula (2-1-8)

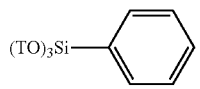

Formula (2-1-7)

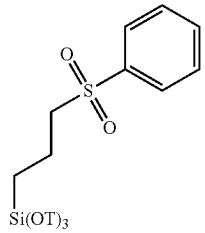

Formula (2-1-8)

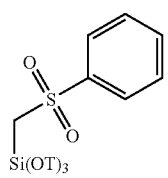

Formula (2-1-9)

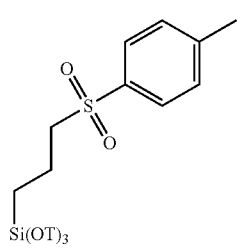

Formula (2-1-10)

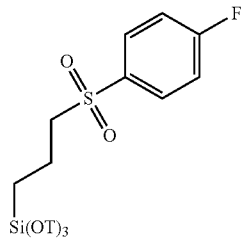

Formula (2-1-11)

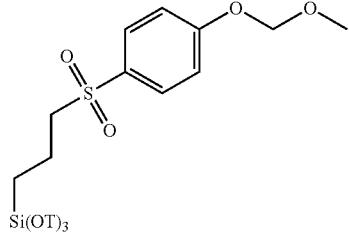

Formula (2-1-12)

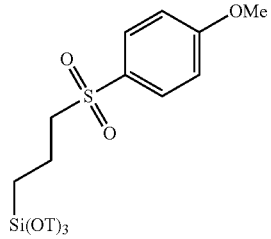

-continued
Formula (2-1-13)
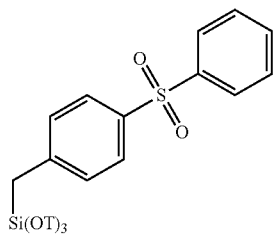
Formula (2-1-14)
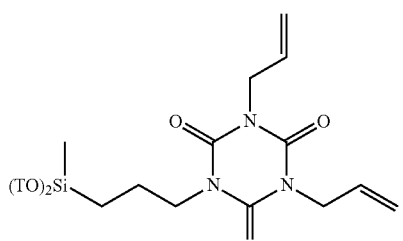
Formula (2-1-15)
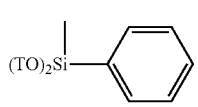
Formula (2-1-16)
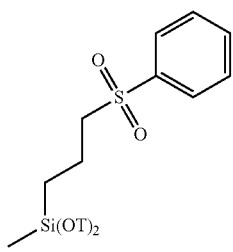
Formula (2-1-17)
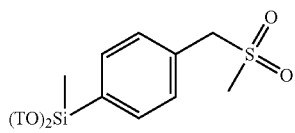
Formula (2-1-18)
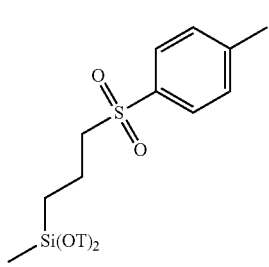
Formula (2-1-19)
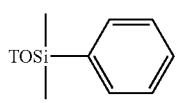
Formula (2-1-20)
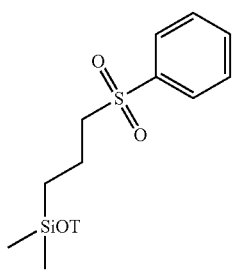
Formula (2-1-21)
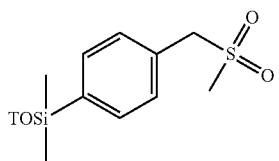
Formula (2-1-22)
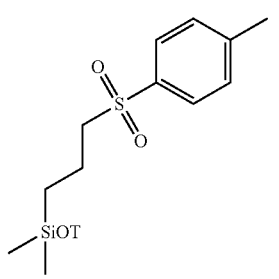
Examples of the hydrolyzable silane of Formula (3) include compounds of Formulae below.
Formula (3-1-1)
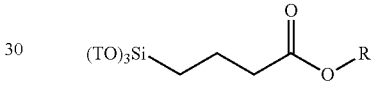
Formula (3-1-2)
Formula (3-1-3)
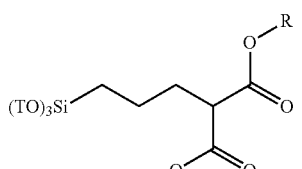
Formula (3-1-4)
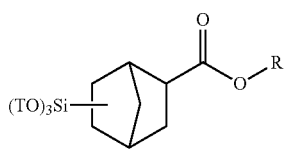
Formula (3-1-5)
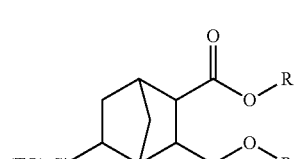
Formula (3-1-6)
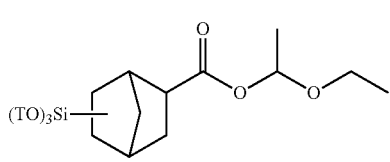

-continued
Formula (3-1-7)
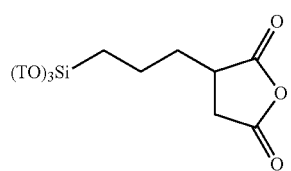
Formula (3-1-8)
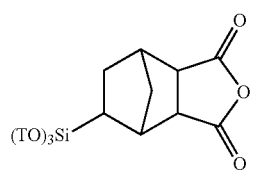
Formula (3-1-9)
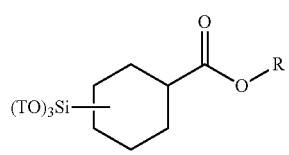
Formula (3-1-10)
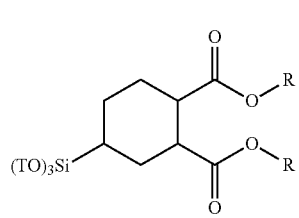
Formula (3-1-11)
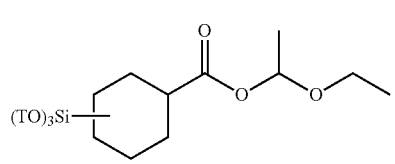
Formula (3-1-12)
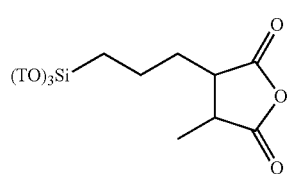
Formula (3-1-13)
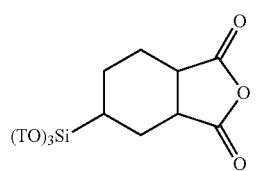
Formula (3-1-14)
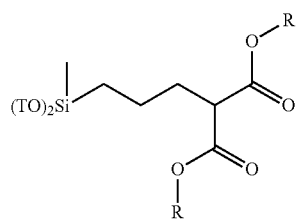
Formula (3-1-15)
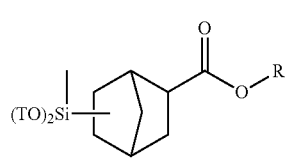
Formula (3-1-16)
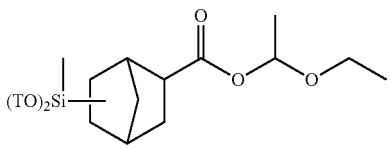
Formula (3-1-17)
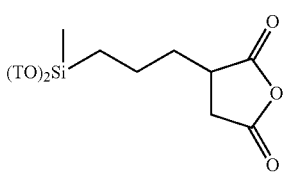
Formula (3-1-18)
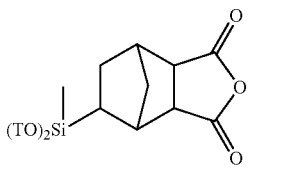
Formula (3-1-19)
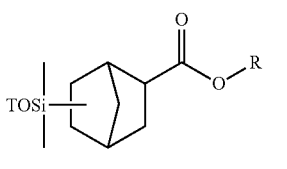
Formula (3-1-20)
Formula (3-1-21)
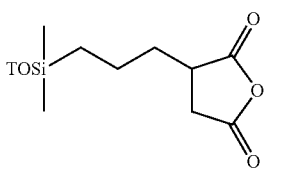
Formula (3-1-22)
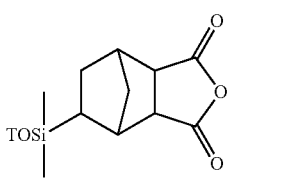
Formula (3-1-23)
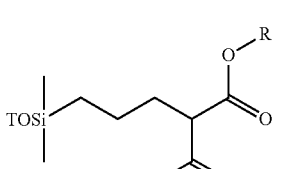
Formula (3-1-24)
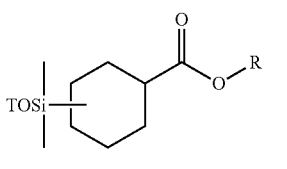

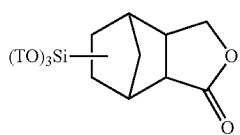
Formula (3-1-25)
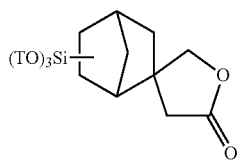
Formula (3-1-26)
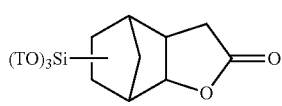
Formula (3-1-27)
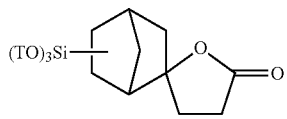
Formula (3-1-28)
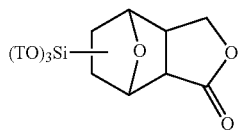
Formula (3-1-29)
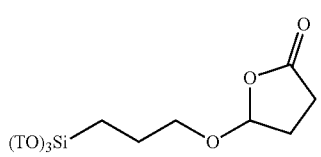
Formula (3-1-30)
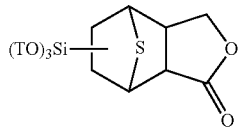
Formula (3-1-31)
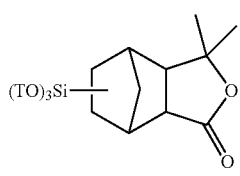
Formula (3-1-32)
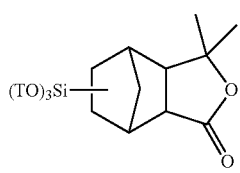
Formula (3-1-33)
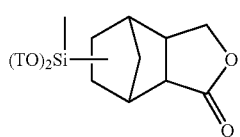
Formula (3-1-34)
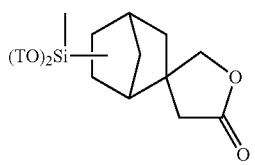
Formula (3-1-35)
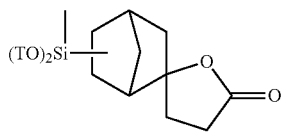
Formula (3-1-36)
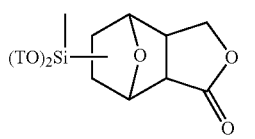
Formula (3-1-37)
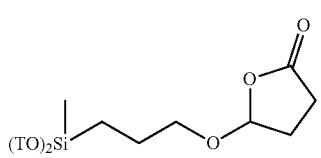
Formula (3-1-38)
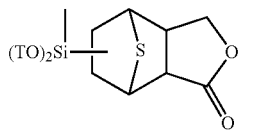
Formula (3-1-39)
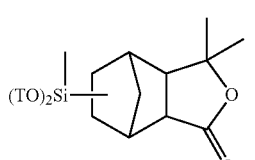
Formula (3-1-40)
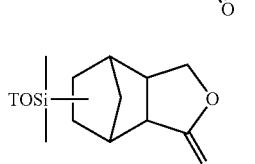
Formula (3-1-41)
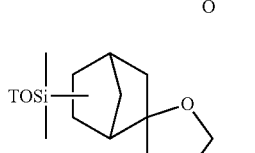
Formula (3-1-42)
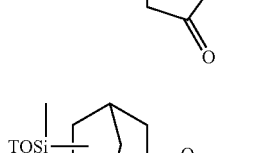
Formula (3-1-43)
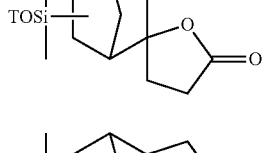
Formual (3-1-44)

Formula (3-1-45)
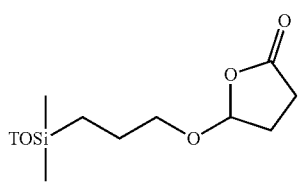
Formula (3-1-46)
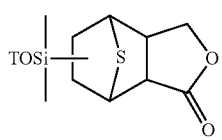
Formula (3-1-47)
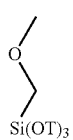
Formula (3-1-48)
Formula (3-1-49)
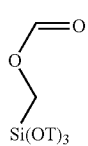
Formula (3-1-50)
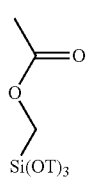
Formula (3-1-51)
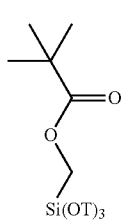
Formula (3-1-52)
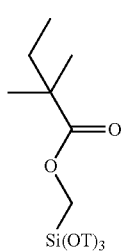
Formula (3-1-53)
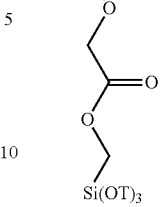
Formula (3-1-54)
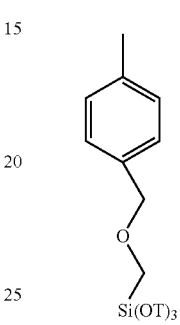
Formula (3-1-55)
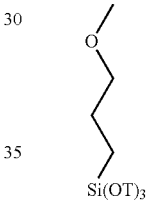
Formula (3-1-56)
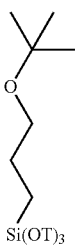
Formula (3-1-57)
Formula (3-1-58)
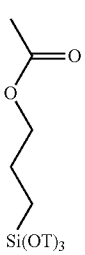

Formula (3-1-59)
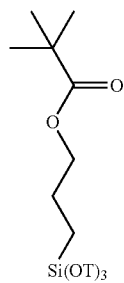
Formula (3-1-60)
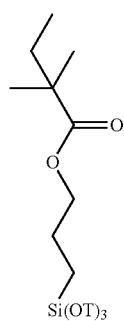
Formula (3-1-61)
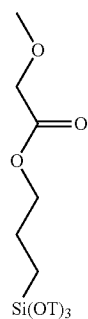
Formula (3-1-62)
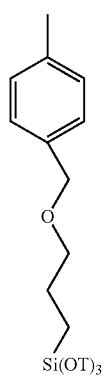
Formula (3-1-63)
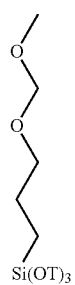
Formula (3-1-64)
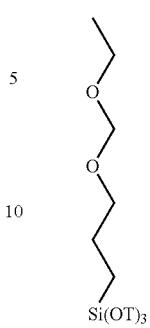
Formula (3-1-65)
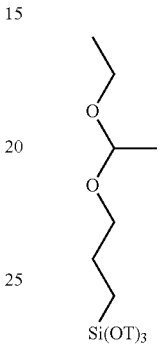
Formula (3-1-66)
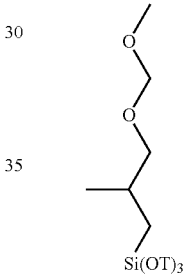
Formula (3-1-67)
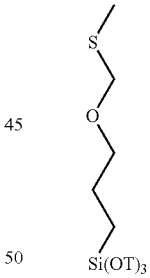
Formula (3-1-68)
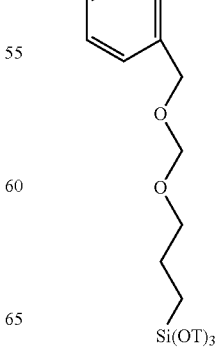

Formula (3-1-69)
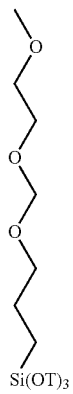
Formula (3-1-70)
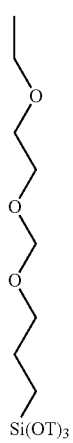
Formula (3-1-71)
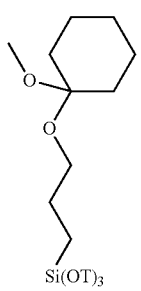
Formula (3-1-72)
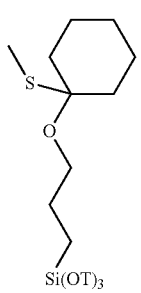
Formula (3-1-73)
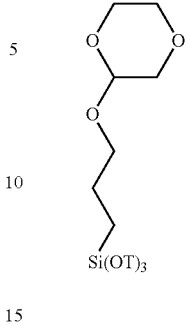
Formula (3-1-74)
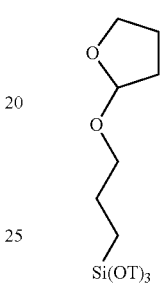
Formula (3-1-75)
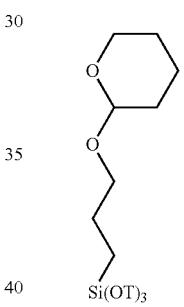
Formula (3-1-76)
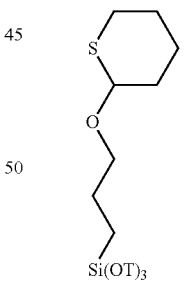
Formula (3-1-77)
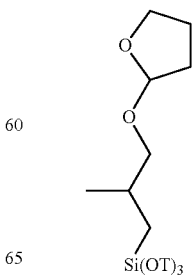

Formula (3-1-78)
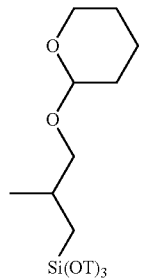
Formula (3-1-83)
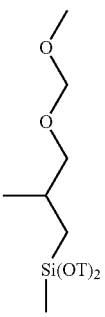
Formula (3-1-79)
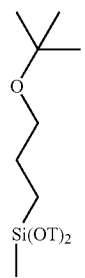
Formula (3-1-84)
Formula (3-1-80)
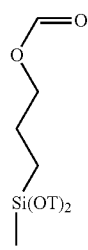
Formula (3-1-85)
Formula (3-1-81)
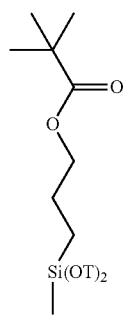
Formula (3-1-86)
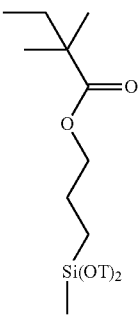
Formula (3-1-82)
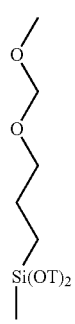
Formula (3-1-87)
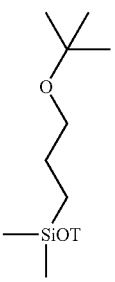

Formula (3-1-88)
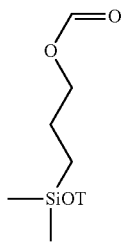

Formula (3-1-89)
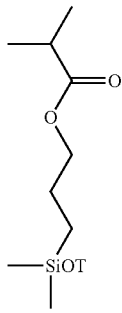

Formula (3-1-90)
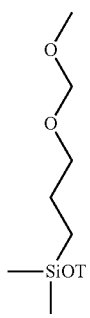

Formula (3-1-91)
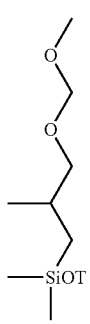

Formula (3-1-92)
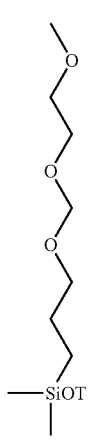

Formula (3-1-93)
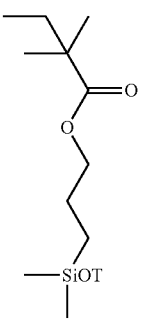

Formula (3-1-94)
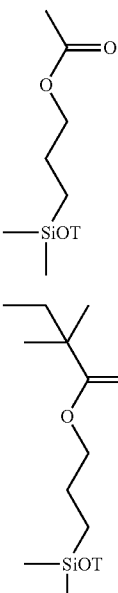

In the above formulae, T is an alkyl group and examples of the alkyl group include the above-exemplified alkyl groups and among them, a methyl group and an ethyl group are preferred.

In the above formulae, examples of R include the groups below.

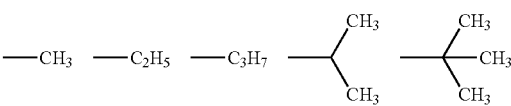
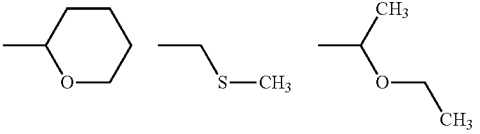
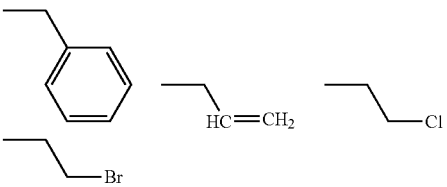

In the resist underlayer film forming composition for lithography of the present invention, the hydrolyzable silane contains a hydrolyzable silane of Formula (1), a combination of a hydrolyzable silane of Formula (1) with a hydrolyzable silane of Formula (2), a combination of a hydrolyzable silane of Formula (1) with a hydrolyzable silane of Formula (3), or a combination of a hydrolyzable silane of Formula (1) and a hydrolyzable silane of Formula (2) and a hydrolyzable silane of Formula (3), and a still other hydrolyzable silane, and the other hydrolyzable silane may be at least one organic silicon compound selected from the group consisting of Formula (4) and Formula (5).

The blending ratio of a hydrolyzable silane of Formula (1), a combination of a hydrolyzable silane of Formula (1) with a hydrolyzable silane of Formula (2), a combination of a hydrolyzable silane of Formula (1) with a hydrolyzable silane of Formula (3), or a hydrolyzable silane containing a combination of a hydrolyzable silane of Formula (1) and a hydrolyzable silane of Formula (2) and a hydrolyzable silane of Formula (3), and the other hydrolyzable silane is in molar ratio of 1:0 to 100, or 1:0.1 to 100, or 1:1 to 100, or 1:1 to 50, or 1:1 to 20.

Although as the silane, a hydrolyzable silane, a hydrolysis product thereof, or a hydrolysis-condensation product thereof is contained, these compounds are preferably used as a hydrolysis-condensation product (polyorganosiloxane), and a hydrolysis-condensation product (polyorganosiloxane) of a hydrolyzable silane of Formula (1), a combination of a hydrolyzable silane of Formula (1) with a hydrolyzable silane of Formula (2), or a combination of a hydrolyzable silane of Formula (1) and a hydrolyzable silane of Formula (2) and a hydrolyzable silane of Formula (3), with a silicon-containing compound of Formula (4) is preferably used.

Examples of an alkyl group, an aryl group, a halogenated alkyl group, a halogenated aryl group, an alkenyl group, and an organic group having an epoxy group, an acryloyl group, a methacryloyl group, a mercapto group, or a cyano group, and further, as a hydrolyzable group, an alkoxy group, an acyloxy group, and a halogen group contained in silicon-containing compounds of Formulae (4) and (5) of $R^{10}$, $R^{11}$, $R^{12}$, and $R^{13}$ include those described above.

Although a hydrolyzable silane of Formula (4) does not include phenylsilane (for example, phenyltrimethoxysilane, phenyltrichlorosilane, phenyltriacetoxysilane, phenyltriethoxysilane, and phenyltriacetoxysilane) exemplified with respect to a hydrolyzable silane of Formula (2) and sulfonyl group-containing phenylsilane, it includes a substituted phenyl silane in which an aryl group of $R^{10}$ is a phenyl group having a substituent other than a sulfonyl group.

The aryl group in the definition of $R^{10}$ in a hydrolyzable silane of Formula (4) is preferably a substituted aryl group such as a substituted phenyl group which is an alkoxyphenyl group, an acyloxyphenyl group, or an organic group containing any of these groups and is bonded to a silicon atom through a Si—C bond. Then, two $R^{10}$s can form a ring with each other and can be bonded to a Si atom.

Examples of the silicon-containing compound of Formula (4) include tetramethoxysilane, tetrachlorosilane, tetraacetoxysilane, tetraethoxysilane, tetra-n-propoxysilane, tetraisopropoxysilane, tetra-n-butoxysilane, methyltrimethoxysilane, methyltrichlorosilane, methyltriacetoxysilane, methyltripropoxysilane, methyltributoxysilane, methyltriamyloxysilane, methyltriphenoxysilane, methyltribenzyloxysilane, methyltriphenethyloxysilane, glycidoxymethyltrimethoxysilane, glycidoxymethyltriethoxysilane, α-glycidoxyethyltrimethoxysilane, α-glycidoxyethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-glycidoxypropyltrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltributoxysilane, γ-glycidoxypropyltriphenoxysilane, α-glycidoxybutyltrimethoxysilane, α-glycidoxybutyltriethoxysilane, β-glycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, β-(3,4-epoxycyclohexyl)ethyltrimethoxysilane, β-(3,4-epoxycyclohexyl)ethyltriethoxysilane, β-(3,4-epoxycyclohexyl)ethyltripropoxysilane, β-(3,4-epoxycyclohexyl)ethyltributoxysilane, β-(3,4-epoxycyclohexyl)ethyltriphenoxysilane, γ-(3,4-epoxycyclohexyl)propyltrimethoxysilane, γ-(3,4-epoxycyclohexyl)propyltriethoxysilane, δ-(3,4-epoxycyclohexyl)butyltrimethoxysilane, δ-(3,4-epoxycyclohexyl)butyltriethoxysilane, glycidoxymethylmethyldimethoxysilane, glycidoxymethylmethyld)butyltriethoxysilane, α-glycidoxyethylmethyldimethoxysilane, α-glycidoxyethylmethyldiethoxysilane, β-glycidoxyethylmethyldimethoxysilane, β-glycidoxyethylethyldimethoxysilane, α-glycidoxypropylmethyldimethoxysilane, α-glycidoxypropylmethyldiethoxysilane, β-glycidoxypropylmethyldimethoxysilane, β-glycidoxypropylethyldimethoxysilane, γ-glycidoxypropylmethyldimethoxysilane, γ-glycidoxypropylmethyldiethoxysilane, γ-glycidoxypropylmethyldipropoxysilane, γ-glycidoxypropylmethyldibutoxysilane, γ-glycidoxypropylmethyldiphenoxysilane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, ethyltrimethoxysilane, ethyltriethoxysilane, vinyltrimethoxysilane, vinyltrichlorosilane, vinyltriacetoxysilane, vinyltriethoxysilane, vinyltriacetoxysilane, methoxyphenyltrimethoxysilane, methoxyphenyltriethoxysilane, methoxyphenyltriacetoxysilane, methoxyphenyltrichlorosilane, methoxybenzyltrimethoxysilane, methoxybenzyltriethoxysilane, methoxybenzyltriacetoxysilane, methoxybenzyltrichlorosilane, methoxyphenethyltrimethoxysilane, methoxyphenethyltriethoxysilane, methoxyphenethyltriacetoxysilane, methoxyphenethyltrichlorosilane, ethoxyphenyltrimethoxysilane, ethoxyphenyltriethoxysilane, ethoxyphenyltriacetoxysilane, ethoxyphenyltrichlorosilane, ethoxybenzyltrimethoxysilane, ethoxybenzyltriethoxysilane, ethoxybenzyltriacetoxysilane, ethoxybenzyltrichlorosilane, isopropoxyphenyltrimethoxysilane, isopropoxyphenyltriethoxysilane, isopropoxyphenyltriacetoxysilane, isopropoxyphenyltrichlorosilane, isopropoxybenzyltrimethoxysilane, isopropoxybenzyltriethoxysilane, isopropoxybenzyltriacetoxysilane, isopropoxybenzyltrichlorosilane, tert-butoxyphenyltrimethoxysilane, tert-butoxyphenyltriethoxysilane, tert-butoxyphenyltriacetoxysilane, tert-butoxyphenyltrichlorosilane, tert-butoxybenzyltrimethoxysilane, tert-butoxybenzyltriethoxysilane, tert-butoxybenzyltriacetoxysilane, tert-butoxybenzyltrichlorosilane, methoxynaphthyltrimethoxysilane, methoxynaphthyltriethoxysilane, methoxynaphthyltriacetoxysilane, methoxynaphthyltrichlorosilane, ethoxynaphthyltrimethoxysilane, ethoxynaphthyltriethoxysilane, ethoxynaphthyltriacetoxysilane, ethoxynaphthyltrichlorosilane, γ-chloropropyltrimethoxysilane, γ-chloropropyltriethoxysilane, γ-chloropropyltriacetoxysilane, 3,3,3-trifluoropropyltrimethoxysilane, γ-methacryloxypropyltrimethoxysilane, γ-mercaptopropyltrimethoxysilane, γ-mercaptopropyltriethoxysilane, β-cyanoethyltriethoxysilane, chloromethyltrimethoxysilane, chloromethyltriethoxysilane, dimethyldimethoxysilane, phenylmethyldimethoxysilane, dimethyldiethoxysilane, phenylmethyldiethoxysilane, γ-chloropropylmethyldimethoxysilane, γ-chloropropylmethyldiethoxysilane, dimethyldiacetoxysilane, γ-methacryloxypropylmethyldimethoxysilane, γ-methacryloxypropylmethyldiethoxysilane, γ-mercaptopropylmethyldimethoxysilane, γ-mercaptomethyldiethoxysilane, methylvinyldimethoxysilane, and methylvinyldiethoxysilane.

In the hydrolyzable silane of Formula (4), the aryl group in the definition of $R^{10}$ is preferably a substituted aryl group and examples thereof include a substituted phenyl group. Examples of the substituted phenyl group include an alkoxyphenyl group, an acyloxyphenyl group, or an organic group containing any of these groups. Examples of such silanes are as follows.
Formula (B-1)
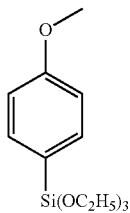
Formula (B-2)
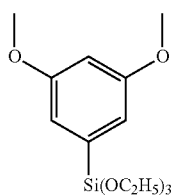
Formula (B-3)
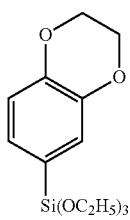
Formula (B-4)
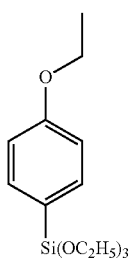
Formula (B-5)
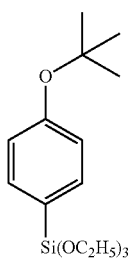
Formula (B-6)
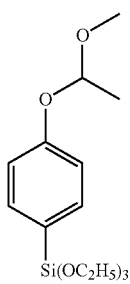
-continued
Formula (B-7)
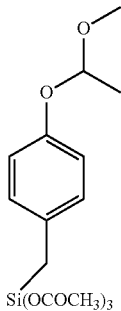
Formula (B-8)
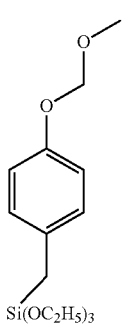
Formula (B-9)
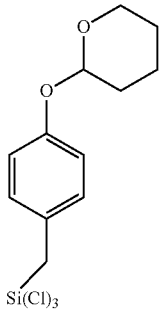
Formula (B-10)
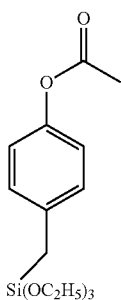
Formula (B-11)
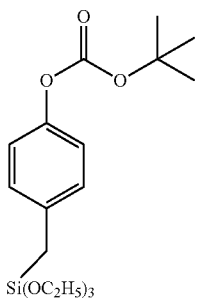

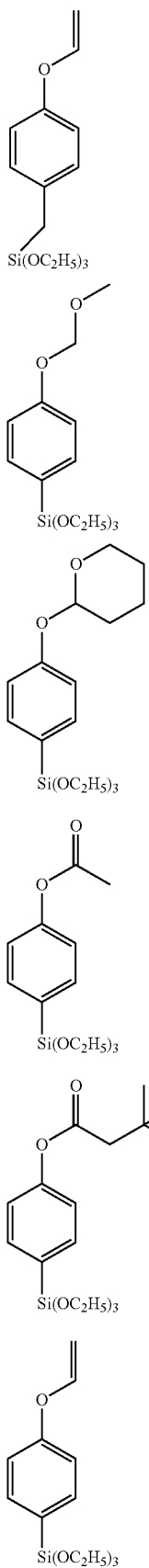
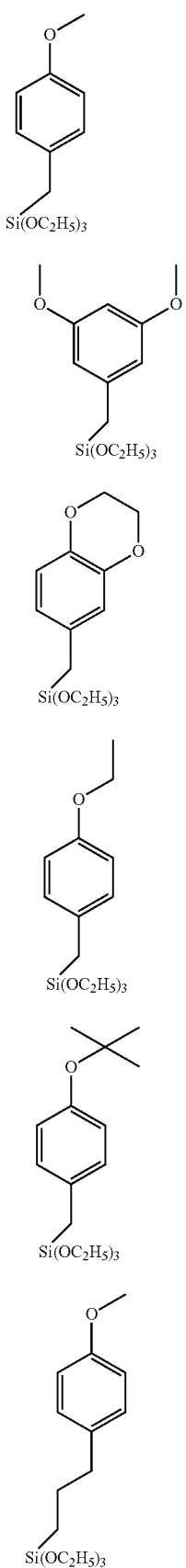
Formula (B-12)
Formula (B-13)
Formula (B-14)
Formula (B-15)
Formula (B-16)
Formula (B-17)
Formula (B-18)
Formula (B-19)
Formula (B-20)
Formula (B-21)
Formula (B-22)
Formula (B-23)

Formula (B-24)
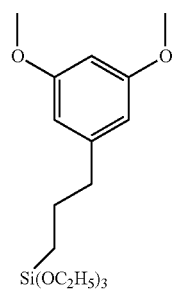
Formula (B-25)
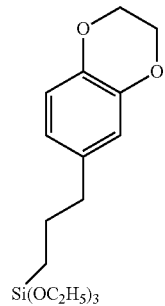
Formula (B-26)
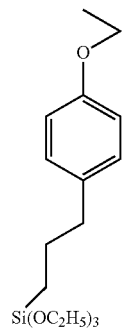
Formula (B-27)
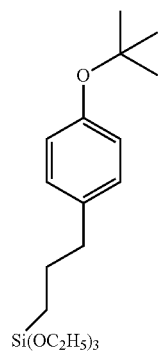
Formula (B-28)
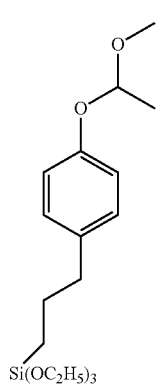
Formula (B-29)
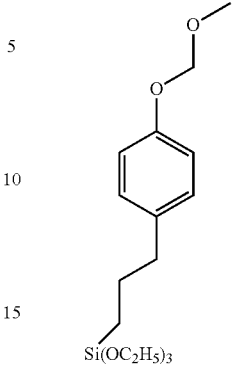
Formula (B-30)
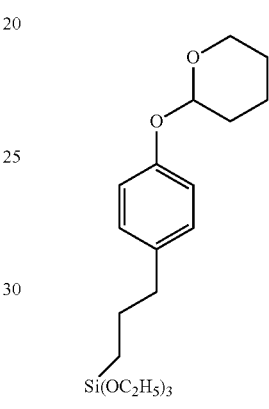
Formula (B-31)
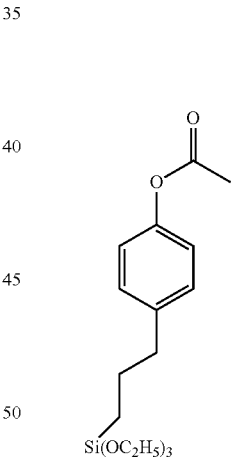
Formula (B-32)
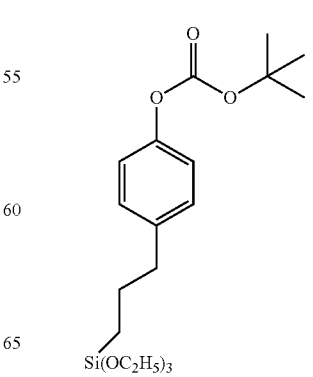

Formula (B-33)
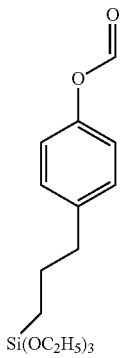

Formula (B-34)
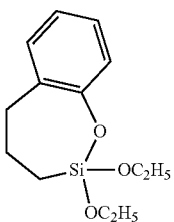

Formula (B-35)
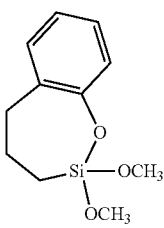

Formula (B-36)
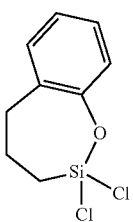

Formula (B-37)
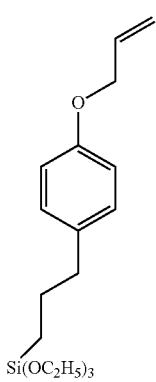

Formula (B-38)
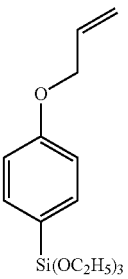

Formula (B-39)
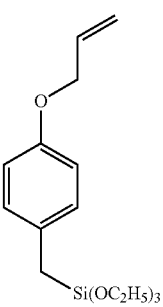

Formula (B-40)
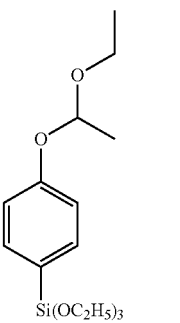

Formula (B-41)
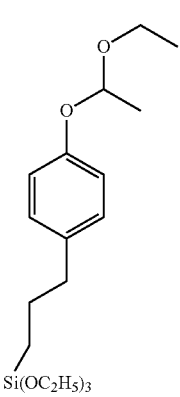

Examples of the silicon-containing compound of Formula (5) include methylenebis(trimethoxysilane), methylenebis(trichlorosilane), methylenebis(triacetoxysilane), ethylenebis(triethoxysilane), ethylenebis(trichlorosilane), ethylenebis(triacetoxysilane), propylenebis(triethoxysilane), butylenebis(trimethoxysilane), phenylenebis(trimethoxysilane), phenylenebis(triethoxysilane), phenylenebis(methyldiethoxysilane), phenylenebis(methyldimethoxysilane), naphthylenebis(trimethoxysilane), bis(trimethoxydisilane), bis(triethoxydisilane), bis(ethyldiethoxydisilane), and bis(methyldimethoxydisilane).

Specific examples of the hydrolysis-condensation product used in the present invention include compounds of Formulae below.

Formula (4-1)
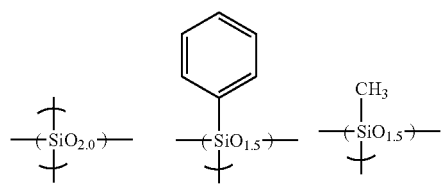
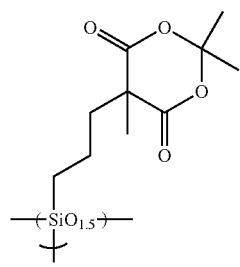
Formula (4-2)
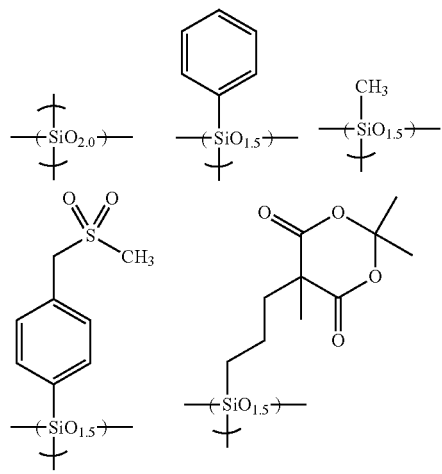
Formula (4-3)
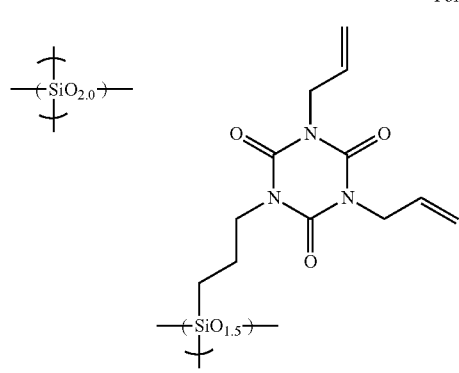
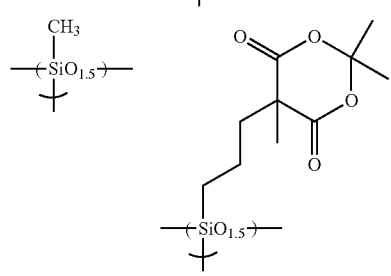
Formula (4-4)
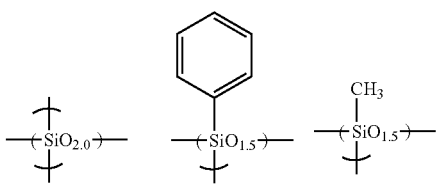
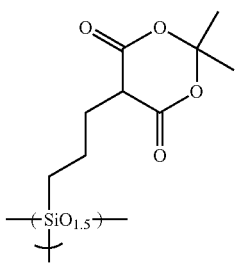
Formula (4-5)
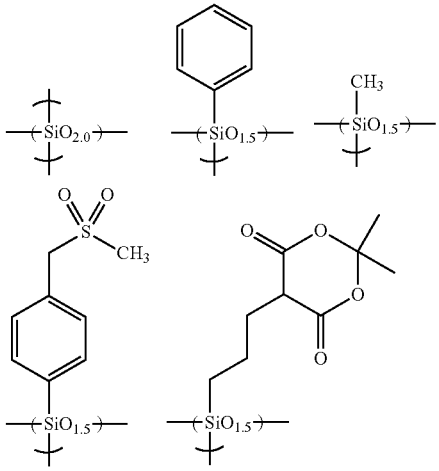
Formula (4-6)
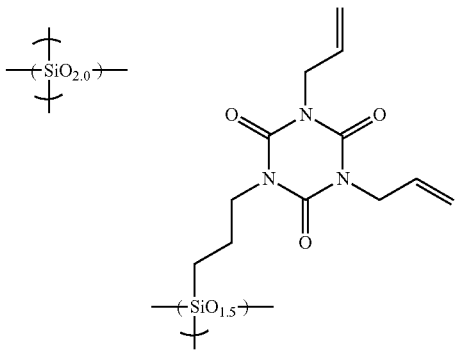
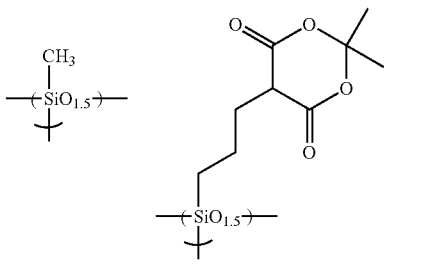

Formula (4-7)
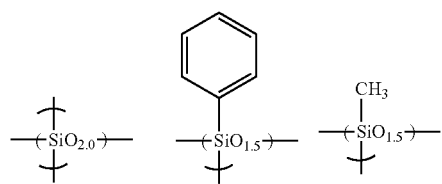
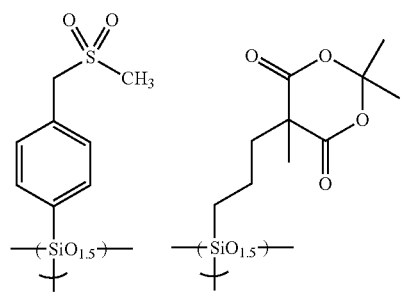
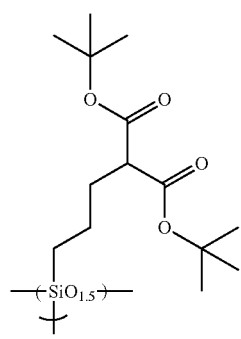
Formula (4-8)
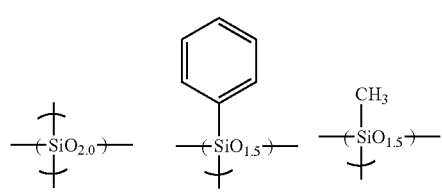
Formula (4-9)
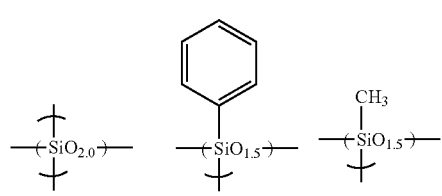
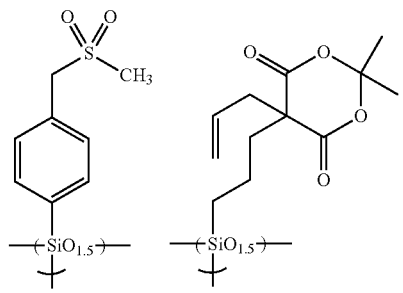
Formula (4-10)
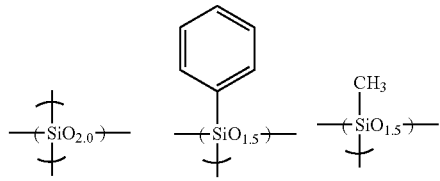
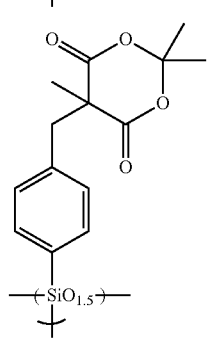
Formula (4-11)
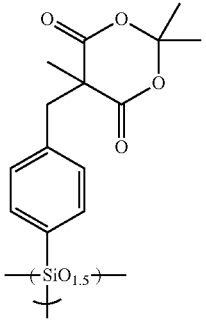
Formula (4-12)
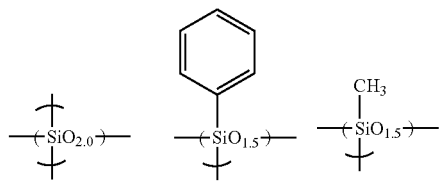
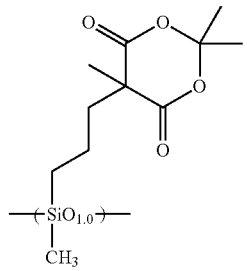

-continued

Formula (4-13)

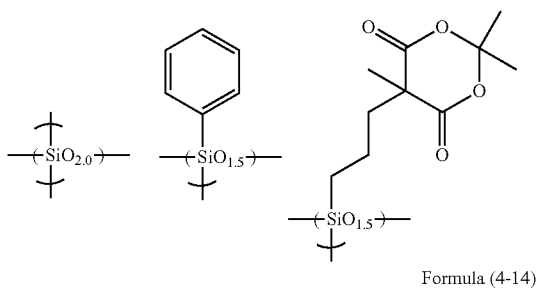

Formula (4-14)

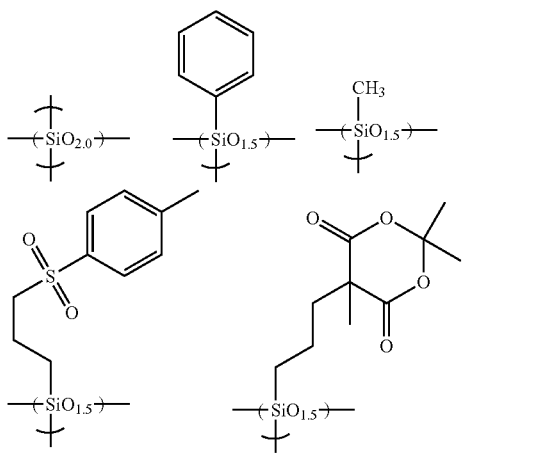

Formula (4-15)

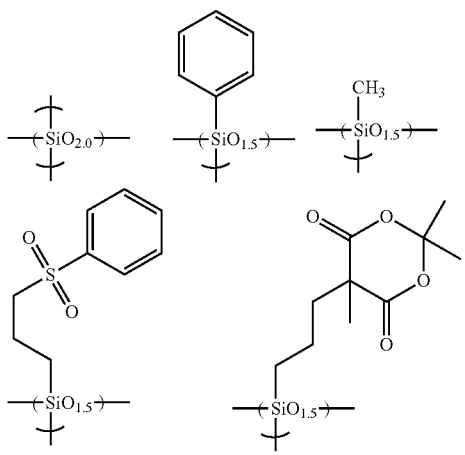

As the hydrolysis-condensation product (polyorganosiloxane) of the hydrolyzable silane, a condensation product having a weight-average molecular weight of 1,000 to 1,000,000 or 1,000 to 100,000 can be obtained. This molecular weight is a molecular weight obtained by a GPC analysis in terms of polystyrene.

Examples of the conditions for the GPC measurement include: using a GPC apparatus (trade name. HLC-8220GPC; manufactured by Tosoh Corporation); using a GPC column (trade names. Shodex KF803L, KF802, and KF801; manufactured by Showa Denko K.K.); using a column temperature of 40° C.; using tetrahydrofuran as the eluting liquid (eluting solvent); using a flow amount (flow rate) of 1.0 mL/min; and using polystyrene (manufactured by Showa Denko K.K.) as the standard sample.

For the hydrolysis of an alkoxysilyl group, an acyloxysilyl group, or a halogenated silyl group, water is used in an amount of 0.5 to 100 mol and preferably 1 to 10 mol, relative to 1 mol of hydrolyzable groups.

A catalyst for the hydrolysis may be used in an amount of 0.001 to 10 mol and preferably 0.001 to 1 mol, relative to 1 mol of hydrolyzable groups.

The reaction temperature for performing the hydrolysis and the condensation is usually 20 to 80° C.

The hydrolysis may be performed either completely or partially. In other words, a hydrolysis product or a monomer may remain in the hydrolysis-condensation product thereof.

During the hydrolysis and the condensation, a catalyst may be used.

Examples of the catalyst for the hydrolysis include metal chelate compounds, organic acids, inorganic acids, organic bases, and inorganic bases.

Examples of the metal chelate compound as the catalyst for the hydrolysis include: titanium chelate compounds such as triethoxy-mono(acetylacetonate)titanium, tri-n-propoxy-mono(acetylacetonate)titanium, triisopropoxy-mono(acetylacetonate)titanium, tri-n-butoxy-mono(acetylacetonate)titanium, tri-sec-butoxy-mono(acetylacetonate)titanium, tri-tert-butoxy-mono(acetylacetonate)titanium, diethoxy-bis(acetylacetonate)titanium, di-n-propoxy-bis(acetylacetonate)titanium, di-isopropoxy-bis(acetylacetonate)titanium, di-n-butoxy-bis(acetylacetonate)titanium, di-sec-butoxy-bis(acetylacetonate)titanium, di-tert-butoxy-bis(acetylacetonate)titanium, monoethoxy-tris(acetylacetonate)titanium, mono-n-propoxy-tris(acetylacetonate)titanium, mono-isopropoxy-tris(acetylacetonate)titanium, mono-n-butoxy-tris(acetylacetonate)titanium, mono-sec-butoxy-tris(acetylacetonate)titanium, mono-tert-butoxy-tris(acetylacetonate)titanium, tetrakis(acetylacetonate)titanium, triethoxy-mono(ethylacetoacetate)titanium, tri-n-propoxy-mono(ethylacetoacetate)titanium, tri-isopropoxy-mono(ethylacetoacetate)titanium, tri-n-butoxy-mono(ethylacetoacetate)titanium, tri-sec-butoxy-mono(ethylacetoacetate)titanium, tri-tert-butoxy-mono(ethylacetoacetate)titanium, diethoxy-bis(ethylacetoacetate)titanium, di-n-propoxy-bis(ethylacetoacetate)titanium, di-isopropoxy-bis(ethylacetoacetate)titanium, di-n-butoxy-bis(ethylacetoacetate)titanium, di-sec-butoxy-bis(ethylacetoacetate)titanium, di-tert-butoxy-bis(ethylacetoacetate)titanium, monoethoxy-tris(ethylacetoacetate)titanium, mono-n-propoxy-tris(ethylacetoacetate)titanium, mono-isopropoxy-tris(ethylacetoacetate)titanium, mono-n-butoxy-tris(ethylacetoacetate)titanium, mono-sec-butoxy-tris(ethylacetoacetate)titanium, mono-tert-butoxy-tris(ethylacetoacetate)titanium, tetrakis(ethylacetoacetate)titanium, mono(acetylacetonate)tris(ethylacetoacetate)titanium, bis(acetylacetonate)bis(ethylacetoacetate)titanium, and tris(acetylacetonate)mono(ethylacetoacetate)titanium; zirconium chelate compounds such as triethoxy-mono(acetylacetonate)zirconium, tri-n-propoxy-mono(acetylacetonate)zirconium, tri-isopropoxy-mono(acetylacetonate)zirconium, tri-n-butoxy-mono(acetylacetonate)zirconium, tri-sec-butoxy-mono(acetylacetonate)zirconium, tri-tert-butoxy-mono(acetylacetonate)zirconium, diethoxy-bis(acetylacetonate)zirconium, di-n-propoxy-bis(acetylacetonate)zirconium, di-isopropoxy-bis(acetylacetonate)zirconium, di-n-butoxy-bis(acetylacetonate)zirconium, di-sec-butoxy-bis(acetylacetonate)zirconium, di-tert-butoxy-bis(acetylacetonate)zirconium, monoethoxy-tris(acetylacetonate)zirconium, mono-n-propoxy-tris(acetylacetonate)zirconium, mono-isopropoxy-tris(acetylacetonate)zirconium, mono-n-butoxy-tris(acetylacetonate)zirconium, mono-sec-butoxy-tris(acetylacetonate)zirconium, mono-tert-butoxy-tris (acetylacetonate)zirconium, tetrakis(acetylacetonate)zirconium, triethoxy-mono(ethylacetoacetate)zirconium, tri-n-propoxy-mono(ethylacetoacetate)zirconium, tri-isopropoxy-mono(ethylacetoacetate)zirconium, tri-n-butoxy-mono(ethylacetoacetate)zirconium, tri-sec-butoxy-mono(ethylacetoacetate)zirconium, tri-tert-butoxy-mono(ethylacetoacetate)zirconium, diethoxy-bis(ethylacetoacetate)zirconium, di-n-propoxy-bis(ethylacetoacetate)zirconium, di-isopropoxy-bis(ethylacetoacetate)zirconium, di-n-butoxy-bis(ethylacetoacetate)zirconium, di-sec-butoxy-bis(ethylacetoacetate)zirconium, di-tert-butoxy-bis(ethylacetoacetate)zirconium, monoethoxy-tris(ethylacetoacetate)zirconium, mono-n-propoxy-tris(ethylacetoacetate)zirconium, mono-isopropoxy-tris(ethylacetoacetate)zirconium, mono-n-butoxy-tris(ethylacetoacetate)zirconium, mono-sec-butoxy-tris(ethylacetoacetate)zirconium, mono-tert-butoxy-tris(ethylacetoacetate)zirconium, tetrakis(ethylacetoacetate)zirconium, mono(acetylacetonate)tris(ethylacetoacetate)zirconium, bis(acetylacetonate)bis(ethylacetoacetate)zirconium, and tris(acetylacetonate)mono(ethylacetoacetate)zirconium; and aluminum chelate compounds such as tris(acetylacetonate)aluminum and tris(ethylacetoacetate)aluminum.

Examples of the organic acid as the catalyst for the hydrolysis include acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, 2-ethylhexanoic acid, oleic acid, stearic acid, linolic acid, linoleic acid, salicylic acid, benzoic acid, p-aminobenzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, and tartaric acid.

Examples of the inorganic acid as the catalyst for the hydrolysis include hydrochloric acid, nitric acid, sulfuric acid, hydrofluoric acid, and phosphoric acid.

Examples of the organic base as the catalyst for the hydrolysis include pyridine, pyrrole, piperazine, pyrrolidine, piperidine, picoline, trimethylamine, triethylamine, monoethanolamine, diethanolamine, dimethylmonoethanolamine, monomethyldiethanolamine, triethanolamine, diazabicyclooctane, diazabicyclo nonane, diazabicyclo undecene, and tetramethylammonium hydroxide. Examples of the inorganic base as the catalyst for the hydrolysis include ammonia, sodium hydroxide, potassium hydroxide, barium hydroxide, and calcium hydroxide. Among these catalysts, metal chelate compounds, organic acids, and inorganic acids are preferred and these catalysts may be used singly or in combination of two or more of them.

Examples of the organic solvent used for the hydrolysis include: aliphatic hydrocarbon solvents such as n-pentane, isopentane, n-hexane, isohexane, n-heptane, isoheptane, 2,2,4-trimethylpentane, n-octane, isooctane, cyclohexane, and methylcyclohexane; aromatic hydrocarbon solvents such as benzene, toluene, xylene, ethylbenzene, trimethylbenzene, methylethylbenzene, n-propylbenzene, isopropylbenzene, diethylbenzene, isobutylbenzene, triethylbenzene, di-isopropylbenzene, n-amylnaphthalene, and trimethylbenzene; monoalcohol solvents such as methanol, ethanol, n-propanol, isopropanol, n-butanol, isobutanol, sec-butanol, tert-butanol, n-pentanol, isopentanol, 2-methylbutanol, sec-pentanol, tert-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethylcarbinol, diacetone alcohol, and cresol; polyalcohol solvents such as ethylene glycol, propylene glycol, 1,3-butylene glycol, pentanediol-2,4,2-methylpentanediol-2,4, hexanediol-2,5, heptanediol-2,4,2-ethylhexanediol-1,3, diethylene glycol, dipropylene glycol, triethylene glycol, tripropylene glycol, and glycerin; ketone solvents such as acetone, methyl ethyl ketone, methyl-n-propyl ketone, methyl-n-butyl ketone, diethyl ketone, methyl-isobutyl ketone, methyl-n-pentyl ketone, ethyl-n-butyl ketone, methyl-n-hexyl ketone, di-isobutyl ketone, trimethylnonanone, cyclohexanone, methylcyclohexanone, 2,4-pentanedione, acetonylacetone, diacetone alcohol, acetophenone, and fenchone; ether solvents such as ethyl ether, isopropyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether, propylene glycol monoethyl ether, propylene glycol monopropyl ether, propylene glycol monobutyl ether, propylene glycol monomethyl ether acetate, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, isopropyl acetate, n-butyl acetate, isobutyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethyleneglycol monomethyl ether acetate, ethyleneglycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, isoamyl propionate, diethyl oxalate, di-n-butyl oxalate, methyl lactate, ethyl lactate, n-butyl lactate, n-amyl lactate, diethyl malonate, dimethyl phthalate, and diethyl phthalate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propane sultone. These solvents may be used singly or in combination of two or more of them.

Particularly preferred are ketone solvents such as acetone, methyl ethyl ketone, methyl-n-propyl ketone, methyl-n-butyl ketone, diethyl ketone, methyl-isobutyl ketone, methyl-n-pentyl ketone, ethyl-n-butyl ketone, methyl-n-hexyl ketone, di-isobutyl ketone, trimethylnonanone, cyclohexanone, methylcyclohexanone, 2,4-pentanedione, acetonylacetone, diacetone alcohol, acetophenone, and fenchone in terms of the storage stability of the solution.

As an additive, bisphenol S or a bisphenol S derivative may be blended in the composition. The blending amount of bisphenol S or a bisphenol S derivative is 0.01 to 20 parts by mass, or 0.01 to 10 parts by mass, or 0.01 to 5 parts by mass, relative to 100 parts by mass of the polyorganosiloxane.

Preferred examples of bisphenol S or a bisphenol S derivative include the compounds below.

Formula (C-1)

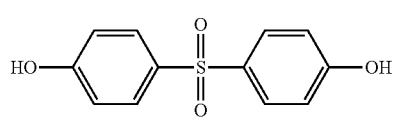

Formula (C-2)

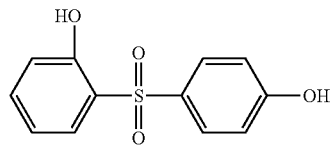

Formula (C-3)

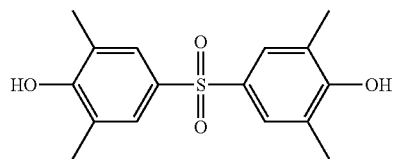

Formula (C-4)

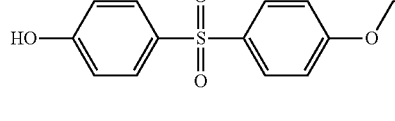

Formula (C-5)

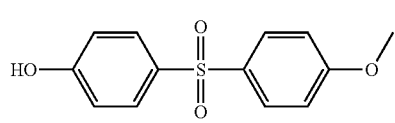

Formula (C-6)

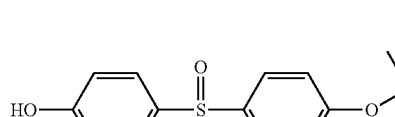

Formula (C-7)

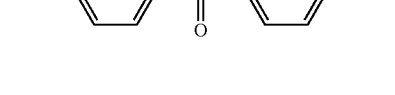

Formula (C-8)

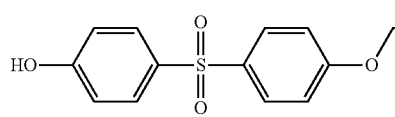

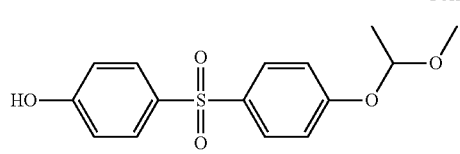

-continued

Formula (C-9)

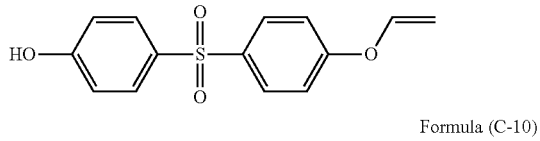

Formula (C-10)

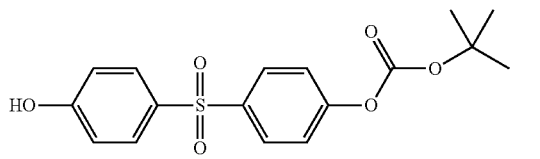

Formula (C-11)

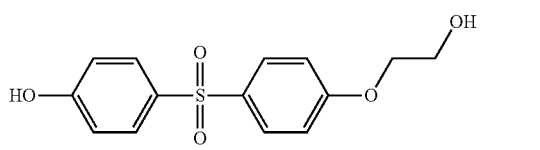

Formula (C-12)

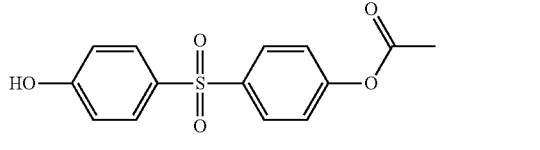

Formula (C-13)

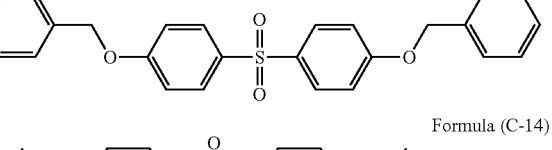

Formula (C-14)

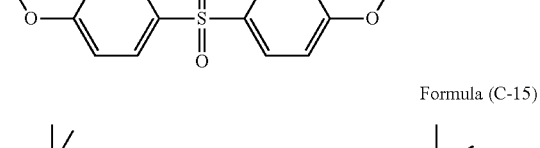

Formula (C-15)

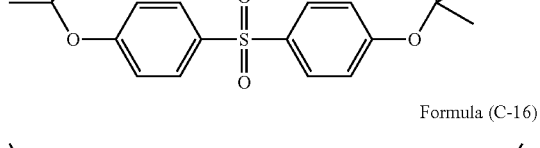

Formula (C-16)

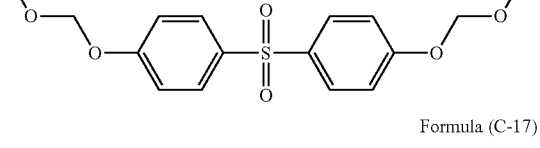

Formula (C-17)

Formula (C-18)

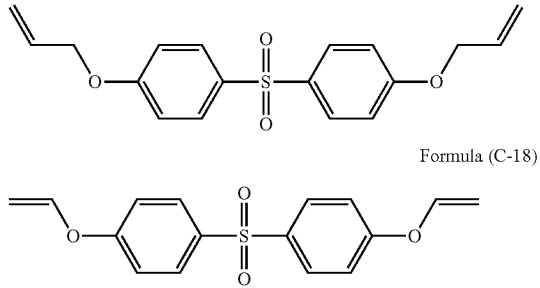

Formula (C-19)

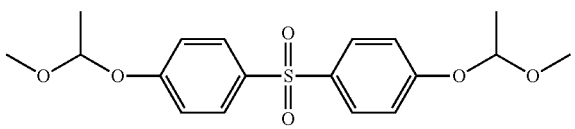

Formula (C-20)

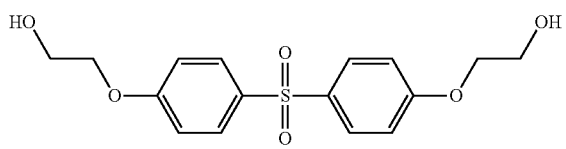

Formula (C-21)

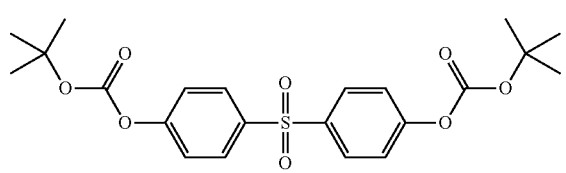

Formula (C-22)

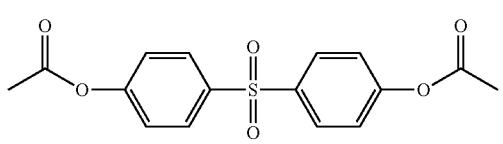

Formula (C-23)

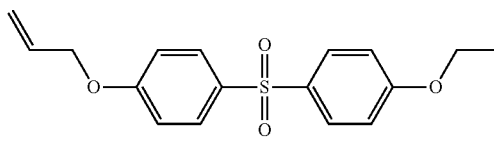

The resist underlayer film forming composition of the present invention may contain a curing catalyst. The curing catalyst performs a function as a curing catalyst when the coating film containing a polyorganosiloxane composed of a hydrolysis-condensation product is cured by heating.

As the curing catalyst, ammonium salts, phosphines, phosphonium salts, and sulfonium salts may be used.

Examples of the ammonium salt include: quaternary ammonium salts having a structure of Formula (D-1):

(Formula (D-1))

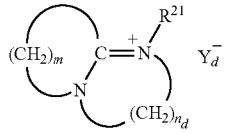

Formula (D-1)

(where m is 2 to 11; $n_d$ is an integer of 2 or 3; $R^{21}$ is an alkyl group or an aryl group; and $Y_d^-$ is an anion);
quaternary ammonium salts having a structure of Formula (D-2):

$$R^{22}R^{23}R^{24}R^{25}N^+Y_d^-$$  Formula (D-2)

(where $R^{22}$, $R^{23}$, $R^{24}$, and $R^{25}$ are an alkyl group or an aryl group; N is a nitrogen atom; $Y_d^-$ is an anion; and $R^{22}$, $R^{23}$, $R^{24}$, and $R^{25}$ are each singly bonded to a nitrogen atom through a C—N bond);
quaternary ammonium salts having a structure of Formula (D-3):

Formula (D-3)

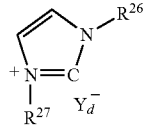

(where $R^{26}$ and $R^{27}$ are an alkyl group or an aryl group; and $Y_d^-$ is an anion); quaternary ammonium salts having a structure of Formula (D-4):

(Formula (D-4))

Formula (D-4)

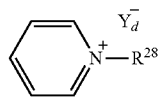

(where $R^{28}$ is an alkyl group or an aryl group; and $Y_d^-$ is an anion);
quaternary ammonium salts having a structure of Formula (D-5):

Formula (D-5)

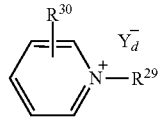

(where $R^{29}$ and $R^{30}$ are an alkyl group or an aryl group; and $Y_d^-$ is an anion); and tertiary ammonium salts having a structure of Formula (D-6):

Formula (D-6)

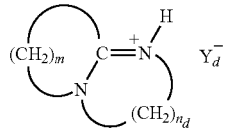

(where m is 2 to 11; $n_d$ is an integer of 2 or 3; H is a hydrogen atom; and $Y_d^-$ is an anion).

Examples of the phosphonium salt include quaternary phosphonium salts of Formula (D-7):

$$R^{31}R^{32}R^{33}R^{34}P^+Y_d^-$$  Formula (D-7)

(where $R^{31}$, $R^{32}$, $R^{33}$, and $R^{34}$ are an alkyl group or an aryl group; P is a phosphorus atom; $Y_d^-$ is an anion; and $R^{31}$, $R^{32}$, $R^{33}$, and $R^{34}$ are each singly bonded to a phosphorus atom through a C—P bond).

Examples of the sulfonium salt include tertiary sulfonium salts of Formula (D-8):

$$R^{15}R^{16}R^{17}S^+Y_d^-$$  Formula (D-8)

(where $R^{15}$, $R^{16}$, and $R^{17}$ are an alkyl group or an aryl group; S is a sulfur atom; $Y_d^-$ is an anion; and $R^{15}$, $R^{16}$, and $R^{17}$ are each singly bonded to a sulfur atom through a C—S bond).

The compound of Formula (D-1) is a quaternary ammonium salt derived from an amine, m is 2 to 11 and $n_d$ is an integer of 2 or 3. $R^{21}$ of the quaternary ammonium salt is a $C_{1-18}$, preferably $C_{2-10}$ alkyl group or a $C_{6-18}$, preferably $C_{6-10}$ aryl group and examples thereof include: linear alkyl groups such as an ethyl group, a propyl group, and a butyl group; a benzyl group; a cyclohexyl group; a cyclohexylmethyl group; and a dicyclopentadienyl group. Examples of the anion ($Y_d^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$).

The compound of Formula (D-2) is a quaternary ammonium salt of $R^{22}R^{23}R^{24}R^{25}N^+Y_d^-$. $R^{22}$, $R^{23}$, $R^{24}$, and $R^{25}$ of the quaternary ammonium salt are each a $C_{1-18}$ alkyl group, a $C_{1-18}$ aryl group, or a silane compound bonded to a silicon atom through a Si—C bond. Examples of the anion ($Y_d^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$) and alcoholate ($-O^-$). The quaternary ammonium salt is commercially available and examples thereof include tetramethylammonium acetate, tetrabutylammonium acetate, triethylbenzylammonium chloride, triethylbenzylammonium bromide, trioctylmethylammonium chloride, tributylbenzylammonium chloride, and trimethylbenzylammonium chloride.

The compound of Formula (D-3) is a quaternary ammonium salt derived from a 1-substituted imidazole. In Formula (D-3), $R^{26}$ and $R^{27}$ are a $C_{1-18}$ alkyl group or a $C_{1-18}$ aryl group. The sum of the numbers of carbon atoms of $R^{26}$ and $R^{27}$ is preferably 7 or more. Examples of $R^{26}$ include a methyl group, an ethyl group, a propyl group, a phenyl group, and a benzyl group and examples of $R^{27}$ include a benzyl group, an octyl group, and an octadecyl group. Examples of the anion ($Y_d^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound is commercially available and may be produced, for example, by allowing an imidazole-based compound such as 1-methylimidazole and 1-benzylimidazole to react with a halogenated alkyl or a halogenated aryl such as benzyl bromide and methyl bromide.

The compound of Formula (D-4) is a quaternary ammonium salt derived from a pyridine. In Formula (D-4), $R^{28}$ is a $C_{1-18}$, preferably $C_{4-18}$ alkyl group or a $C_{1-18}$, preferably $C_{4-18}$ aryl group. Examples of $R^{28}$ include a butyl group, an octyl group, a benzyl group, a lauryl group. Examples of the anion ($Y_d^-$) include: halogen ions such as a chlorine ion ($Cl^-$), a bromine ion ($Br^-$), and an iodine ion (f); and acid groups such as carboxylato ($-COO^-$), sulfonato ($-SO_3^-$), and alcoholate ($-O^-$). The compound is commercially available and may be produced, for example, by allowing a pyridine to react with a halogenated alkyl or a halogenated aryl such as lauryl chloride, benzyl chloride, benzyl bromide, methyl bromide, and octyl bromide. Examples of the compound include N-lauryl pyridinium and bromide N-benzyl pyridinium.

The compound of Formula (D-5) is a quaternary ammonium salt derived from a substituted pyridine such as picoline. In Formula (D-5), $R^{29}$ is a $C_{1-18}$, preferably $C_{4-18}$ alkyl group or a $C_{1-18}$, preferably $C_{4-18}$ aryl group. Examples of $R^{29}$ include a methyl group, an octyl group, a lauryl group, a benzyl group. $R^{30}$ is a $C_{1-18}$, alkyl group or a $C_{1-18}$ aryl group. When $R^{30}$ is a quaternary ammonium salt derived from an picoline, $R^{30}$ is a methyl group. Examples of the anion ($Y_d^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound is commercially available and may be produced, for example, by allowing a substituted pyridine such as picoline to react with a halogenated alkyl or a halogenated aryl such as methyl bromide, octyl bromide, lauryl chloride, benzyl chloride, benzyl bromide. Examples of the compound include N-benzylpicolinium chloride, N-benzylpicolinium bromide, and N-laurylpicolinium chloride.

The compound of Formula (D-6) is a tertiary ammonium salt derived from an amine. In Formula (D-6), m is 2 to 11 and $n_d$ is an integer of 2 or 3. Examples of the anion ($Y_1^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound may be produced by a reaction of an amine with a weak acid such as a carboxylic acid and phenol. Examples of the carboxylic acid include formic acid and acetic acid. When formic acid is used, the anion ($Y_d^-$) is $HCOO^-$ and when acetic acid is used, the anion ($Y_d^-$) is $CH_3COO^-$. In addition, when phenol is used, the anion ($Y_d^-$) is $C_6H_5O^-$.

The compound of Formula (D-7) is a quaternary phosphonium salt having a structure of $R^{31}R^{32}R^{33}R^{34}P^+Y_d^-$. $R^{31}$, $R^{32}$, $R^{33}$, and $R^{34}$ are each a $C_{1-18}$ alkyl group, a $C_{1-18}$ aryl group, or a silane compound bonded to a silicon atom through a Si—C bond. Preferably, three groups among four substituents of $R^{31}$ to $R^{34}$ are a phenyl group or a substituted phenyl group such as a phenyl group and a tolyl group and the remaining one group is a $C_{1-18}$ alkyl group, a $C_{1-18}$ aryl group, or a silane compound bonded to a silicon atom through a Si—C bond. Examples of the anion ($Y_d^-$) include: halogen ions such as a chlorine ion ($Cl^-$), a bromine ion ($Br^-$), and an iodine ion ($I^-$); and acid groups such as carboxylato ($-COO^-$), sulfonato ($-SO_3^-$), and alcoholate ($-O^-$). The compound is commercially available and examples of the compound include: halogenated tetraalkylphosphoniums such as a halogenated tetra-n-butylphosphonium and a halogenated tetra-n-propylphosphonium; halogenated trialkylbenzylphosphoniums such as a halogenated triethylbenzylphosphonium; halogenated triphenylmonoalkylphosphoniums such as a halogenated triphenylmethylphosphonium and a halogenated triphenylethylphosphonium; halogenated triphenylbenzylphosphoniums; halogenated tetraphenylphosphoniums; halogenated tritolylmonoarylphosphoniums; and halogenated tritolylmonoalkylphosphoniums (the halogen atom is a chlorine atom or a bromine atom). Particularly preferred examples of the compound include: halogenated triphenylmonoalkylphosphoniums such as a halogenated triphenylmethylphosphonium and a halogenated triphenylethylphosphonium; halogenated triphenylmonoarylphosphoniums such as a halogenated triphenylbenzylphosphonium; halogenated tritolylmonoarylphosphoniums such as a halogenated tritolylmonophenylphosphonium; and halogenated tritolylmonoalkylphosphoniums such as a halogenated tritolylmonomethylphosphonium (the halogen atom is a chlorine atom or a bromine atom).

Examples of the phosphines include: primary phosphines such as methylphosphine, ethylphosphine, propylphosphine, isopropylphosphine, isobutylphosphine, and phenylphosphine; secondary phosphines such as dimethylphosphine, diethylphosphine, diisopropylphosphine, diisoamylphosphine, and diphenylphosphine; and tertiary phosphines such as trimethylphosphine, triethylphosphine, triphenylphosphine, methyldiphenylphosphine, and dimethylphenylphosphine.

The compound of Formula (D-8) is a tertiary sulfonium salt having a structure of $R^{15}R^{16}R^{17}S^+Y_d^-$. $R^{15}$, $R^{16}$, and $R^{17}$ are each a $C_{1-18}$ alkyl group, a $C_{1-18}$ aryl group, or a silane compound bonded to a silicon atom through a Si—C bond. Preferably, three groups among four substituents of $R^{15}$ to $R^{17}$ are a phenyl group or a substituted phenyl group such as a phenyl group and a tolyl group and the remaining one group is a $C_{1-18}$ alkyl group or a $C_{1-18}$ aryl group. Examples of the anion ($Y_d^-$) include: halogen ions such as a chlorine ion (Cl$^-$), a bromine ion (Br$^-$), and an iodine ion (I$^-$); and acid groups such as carboxylato (—COO$^-$), sulfonato (—SO$_3^-$), and alcoholate (—O$^-$). The compound is commercially available and examples of the compound include: halogenated tetraalkylsulfoniums such as a halogenated tri-n-butylsulfonium and a halogenated tri-n-propylsulfonium; halogenated trialkylbenzylsulfoniums such as a halogenated diethylbenzylsulfonium; halogenated diphenylmonoalkylsulfoniums such as a halogenated diphenylmethylsulfonium and a halogenated diphenylethylsulfonium; halogenated triphenylsulfoniums (the halogen atom is a chlorine atom or a bromine atom); tetraalkylphosphonium carboxylates such as tri-n-butylsulfonium carboxylate and tri-n-propylsulfonium carboxylate; trialkylbenzylsulfonium carboxylates such as diethylbenzylsulfonium carboxylate; diphenylmonoalkylsulfonium carboxylates such as diphenylmethylsulfonium carboxylate and diphenylethylsulfonium carboxylate; and triphenylsulfonium carboxylate. Particularly preferred are a halogenated triphenylsulfonium and triphenylsulfonium carboxylate.

The amount of the curing catalyst is 0.01 to 10 parts by mass, or 0.01 to 5 parts by mass, or 0.01 to 3 parts by mass, relative to 100 parts by mass of the polyorganosiloxane.

From the hydrolysis-condensation product (polymer) obtained by hydrolyzing and condensing a hydrolyzable silane in a solvent using a catalyst, an alcohol as a by-product, the used catalyst for the hydrolysis, and the used water can be simultaneously removed by distilling them under reduced pressure or the like. An acid catalyst or a base catalyst used for the hydrolysis can be removed by neutralization or ion exchange. Then, with respect to the resist underlayer film forming composition for lithography of the present invention, in the resist underlayer film forming composition containing the hydrolysis-condensation product thereof, an organic acid, water, an alcohol, or a combination thereof may be blended to stabilize the composition.

Examples of the organic acid include oxalic acid, malonic acid, methylmalonic acid, succinic acid, maleic acid, malic acid, tartaric acid, phthalic acid, citric acid, glutaric acid, citric acid, lactic acid, and salicylic acid. Among them, oxalic acid and maleic acid are preferred. The amount of the organic acid to be blended in the composition is 0.1 to 5.0 parts by mass, relative to 100 parts by mass of the condensation product (polyorganosiloxane). As the water to be blended in the composition, pure water, ultrapure water, ion-exchanged water, or the like may be used and the blending amount thereof may be 1 to 20 parts by mass, relative to 100 parts by mass of the resist underlayer film forming composition.

The alcohol to be blended in the composition is preferably an alcohol that can be easily diffused by heating the composition after the application of the composition, and examples thereof include methanol, ethanol, propanol, isopropanol, and butanol. The blending amount of the alcohol may be 1 to 20 parts by mass, relative to 100 parts by mass of the resist underlayer film forming composition.

The resist underlayer film forming composition for lithography of the present invention may contain, in addition to the above mentioned components, if necessary, an organic polymer compound, a photoacid generator, a surfactant or the like.

By using an organic polymer compound, the dry etching rate (a decreased amount of the film thickness per unit time), the attenuation coefficient, the refractive index, and the like of a resist underlayer film formed from the underlayer film forming composition for lithography of the present invention can be controlled.

The organic polymer compound is not particularly limited and various organic polymers such as condensation polymerization polymers and addition polymerization polymers may be used. As the organic polymer compound, addition polymerization polymers and condensation polymerization polymers may be used such as polyesters, polystyrene, polyimides, acrylic polymers, methacrylic polymers, polyvinylethers, phenolnovolacs, naphtholnovolacs, polyethers, polyamides, and polycarbonates. Organic polymers having an aromatic ring structure are preferably used, functioning as a light absorbing moiety such as a benzene ring, a naphthalene ring, an anthracene ring, a triazine ring, a quinoline ring, and a quinoxaline ring.

Examples of such an organic polymer compound include addition polymerization polymers containing as a structure unit thereof, an addition polymerizable monomer such as benzyl acrylate, benzyl methacrylate, phenyl acrylate, naphthyl acrylate, anthryl methacrylate, anthrylmethyl methacrylate, styrene, hydroxystyrene, benzyl vinyl ether, and N-phenylmaleimide, and condensation polymerization polymers such as phenolnovolacs and naphtholnovolacs.

When an addition polymerization polymer is used as the organic polymer compound, the polymer compound may be either a homopolymer or a copolymer. For producing the addition polymerization polymer, an addition polymerizable monomer is used. Examples of such an addition polymerizable monomer include acrylic acid, methacrylic acid, acrylic acid ester compounds, methacrylic acid ester compounds, acrylamide compounds, methacrylamide compounds, vinyl compounds, styrene compounds, maleimide compounds, maleic anhydride, and acrylonitrile.

Examples of the acrylic acid ester compound include methyl acrylate, ethyl acrylate, n-hexyl acrylate, isopropyl acrylate, cyclohexyl acrylate, benzyl acrylate, phenyl acrylate, anthrylmethyl acrylate, 2-hydroxyethyl acrylate, 3-chloro-2-hydroxypropyl acrylate, 2-hydroxypropyl acrylate, 2,2,2-trifluoroethyl acrylate, 2,2,2-trichloroethyl acrylate, 2-bromoethyl acrylate, 4-hydroxybutyl acrylate, 2-methoxyethyl acrylate, tetrahydrofurfuryl acrylate, 2-methyl-2-adamantyl acrylate, 5-acryloyloxy-6-hydroxynorbornene-2-carboxylic-6-lactone, 3-acryloxypropyltriethoxysilane, and glycidyl acrylate.

Examples of the methacrylic acid ester compound include methyl methacrylate, ethyl methacrylate, n-hexyl methacrylate, isopropyl methacrylate, cyclohexyl methacrylate, benzyl methacrylate, phenyl methacrylate, anthrylmethyl methacrylate, 2-hydroxyethyl methacrylate, 2-hydroxypropyl methacrylate, 2,2,2-trifluoroethyl methacrylate, 2,2,2-trichloroethyl methacrylate, 2-bromoethyl methacrylate, 4-hydroxybutyl methacrylate, 2-methoxyethyl methacrylate, tetrahydrofurfuryl methacrylate, 2-methyl-2-adamantyl methacrylate, 5-methacryloyloxy-6-hydroxynorbornene-2-carboxylic-6-lactone, 3-methacryloxypropyltriethoxysilane, glycidyl methacrylate, 2-phenylethyl methacrylate, hydroxyphenyl methacrylate, and bromophenyl methacrylate.

Examples of the acrylamide compound include acrylamide, N-methylacrylamide, N-ethylacrylamide, N-benzylacrylamide, N-phenylacrylamide, N,N-dimethylacrylamide, and N-anthrylacrylamide.

Examples of the methacrylamide compound include methacrylamide, N-methylmethacrylamide, N-ethylmethacrylamide, N-benzylmethacrylamide, N-phenylmethacrylamide, N,N-dimethylmethacrylamide, and N-anthrylacrylamide.

Examples of the vinyl compound include vinyl alcohol, 2-hydroxyethyl vinyl ether, methyl vinyl ether, ethyl vinyl ether, benzyl vinyl ether, vinylacetic acid, vinyltrimethoxysilane, 2-chloroethyl vinyl ether, 2-methoxyethyl vinyl ether, vinylnaphthalene, and vinylanthracene.

Examples of the styrene compound include styrene, hydroxystyrene, chlorostyrene, bromostyrene, methoxystyrene, cyanostyrene, and acetylstyrene.

Examples of the maleimide compound include maleimide, N-methylmaleimide, N-phenylmaleimide, N-cyclohexylmaleimide, N-benzylmaleimide, and N-hydroxyethylmaleimide.

When a condensation polymerization polymer is used as such a polymer, examples of such a polymer include condensation polymerization polymers of a glycol compound and a dicarboxylic acid compound. Examples of the glycol compound include diethylene glycol, hexamethylene glycol, and butylene glycol. Examples of the dicarboxylic acid compound include succinic acid, adipic acid, terephthalic acid, and maleic anhydride. Examples of the polymer also include polyesters, polyamides, and polyimides such as polypyromellitimide, poly(p-phenyleneterephthalamide), polybutylene terephthalate, and polyethylene terephthalate.

When the organic polymer compound contains a hydroxy group, the hydroxy group can progress a crosslinking reaction with a polyorganosiloxane.

As the organic polymer compound, a polymer compound having a weight-average molecular weight of, for example, 1,000 to 1,000,000, or 3,000 to 300,000, or 5,000 to 200,000, or 10,000 to 100,000 may be used.

The organic polymer compounds may be used singly or in combination of two or more of them.

When the organic polymer compound is used, the content thereof is 1 to 200 parts by mass, or 5 to 100 parts by mass, or 10 to 50 parts by mass, or 20 to 30 parts by mass, relative to 100 parts by mass of the condensation product (polyorganosiloxane).

The resist underlayer film forming composition of the present invention may contain an acid generator.

Examples of the acid generator include thermoacid generators and photoacid generators.

The photoacid generator generates an acid during exposure of the resist. Therefore, the acidity of the underlayer film can be controlled. This is one method for adjusting the acidity of the underlayer film to that of the resist as an upper layer of the underlayer film. By adjusting the acidity of the underlayer film, the pattern shape of the resist formed in the upper layer can be controlled.

Examples of the photoacid generator contained in the resist underlayer film forming composition of the present invention include onium salt compounds, sulfonimide compounds, and disulfonyl diazomethane compounds.

Examples of the onium salt compound include: iodonium salt compounds such as diphenyliodoniumhexafluorophosphate, diphenyliodoniumtrifluoromethanesulfonate, diphenyliodoniumnonafluoro n-butane sulfonate, diphenyliodoniumperfluoro n-octane sulfonate, diphenyliodoniumcamphorsulfonate, bis(4-tert-butylphenyl)iodoniumcamphorsulfonate, and bis(4-tert-butylphenyl)iodoniumtrifluoromethanesulfonate; and sulfonium salt compounds such as triphenylsulfoniumhexafluoroantimonate, triphenylsulfoniumnonafluoro n-butane sulfonate, triphenylsulfoniumcamphorsulfonate, and triphenylsulfoniumtrifluoromethanesulfonate.

Examples of the sulfonimide compound include N-(trifluoromethanesulfonyloxy)succinimide, N-(nonafluoro n-butane sulfonyloxy)succinimide, N-(camphorsulfonyloxy)succinimide, and N-(trifluoromethanesulfonyloxy) naphthalimide.

Examples of the disulfonyldiazomethane compound include bis(trifluoromethylsulfonyl)diazomethane, bis(cyclohexylsulfonyl)diazomethane, bis(phenylsulfonyl)diazomethane, bis(p-toluenesufonyl)diazomethane, bis(2,4-dimethylbenzenesulfonyl)diazomethane, and methylsulfonyl-p-toluenesulfonyldiazomethane.

These photoacid generators may be used singly or in combination of two or more of them.

When the photoacid generator is used, the content thereof is 0.01 to 5 parts by mass, or 0.1 to 3 parts by mass, or 0.5 to 1 part by mass, relative to 100 parts by mass of the condensation product (polyorganosiloxane).

The surfactant is effective in suppressing the formation of a pin hole, a striation, and the like when the resist underlayer film forming composition for lithography of the present invention is applied onto a substrate.

Examples of the surfactant contained in the resist underlayer film forming composition of the present invention include: nonionic surfactants, for example, polyoxyethylene alkyl ethers such as polyoxyethylene lauryl ether, polyoxyethylene stearyl ether, polyoxyethylene cetyl ether, and polyoxyethylene oleyl ether, polyoxyethylene alkylaryl ethers such as polyoxyethylene octylphenol ether and polyoxyethylene nonylphenol ether, polyoxyethylene-polyoxypropylene block copolymers, sorbitan fatty acid esters such as sorbitan monolaurate, sorbitan monopalmitate, sorbitan monostearate, sorbitan monooleate, sorbitan trioleate, and sorbitan tristearate, polyoxyethylene sorbitan fatty acid esters such as polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorinated surfactants, for example, EFTOP EF301, EF303, and EF352 (trade names; manufactured by Tohkem Products Corp.), MEGAFAC F171, F173, R-08, and R-30 (trade names; manufactured by Dainippon Ink & Chemicals Inc.), Fluorad FC430 and FC43 1 (trade names; manufactured by Sumitomo 3M Limited), AsahiGuard AG710 and Surflon S-382, SC101, SC102, SC103, SC104, SC105, and SC106 (trade names; manufactured by Asahi Glass Co., Ltd.); and organosiloxane polymer KP341 (manufactured by Shin-Etsu Chemical Co., Ltd.). These surfactants may be used singly or in combination of two or more of them. When the surfactant is used, the content thereof is 0.0001 to 5 parts by mass, or 0.001 to 1 part by mass, or 0.01 to 0.5 part by mass, relative to 100 parts by mass of the condensation product (polyorganosiloxane).

In the resist underlayer film forming composition of the present invention, a rheology controlling agent and an adhesion assistant may be blended. The rheology controlling agent is effective in enhancing the fluidity of the underlayer film forming composition. The adhesion assistant is effective in enhancing the adhesion of the underlayer film to the semiconductor substrate or the resist.

The solvent used for the resist underlayer film forming composition of the present invention is not particularly limited to be used so long as the solvent can dissolve the solid content. Examples of such a solvent include methyl cellosolve acetate, ethyl cellosolve acetate, propylene glycol, propylene glycol monomethyl ether, propylene glycol monoethyl ether, methylisobutylcarbinol, propylene glycol monobutyl ether, propylene glycol monomethyl ether acetate, propylene glycol monoethyl ether acetate, propylene glycol monopropyl ether acetate, propylene glycol monobutyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethylene glycol monomethyl ether, ethylene glycol monoethyl ether, ethylene glycol monopropyl ether, ethylene glycol monobutyl ether, ethylene glycol monomethyl ether acetate, ethylene glycol monoethyl ether acetate, ethylene glycol monopropyl ether acetate, ethylene glycol monobutyl ether acetate, diethylene glycol dimethyl ether, diethylene glycol diethyl ether, diethylene glycol dipropyl ether, diethylene glycol dibutyl ether, propylene glycol monomethyl ether, propylene glycol dimethyl ether, propylene glycol diethyl ether, propylene glycol dipropyl ether, propylene glycol dibutyl ether, ethyl lactate, propyl lactate, isopropyl lactate, butyl lactate, isobutyl lactate, methyl formate, ethyl formate, propyl formate, isopropyl formate, butyl formate, isobutyl formate, amyl formate, isoamyl formate, methyl acetate, ethyl acetate, amyl acetate, isoamyl acetate, hexyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, isobutyl butyrate, ethyl hydroxyacetate, ethyl 2-hydroxy-2-methylpropionate, methyl 3-methoxy-2-methylpropionate, methyl 2-hydroxy-3-methylbutyrate, ethyl methoxyacetate, ethyl ethoxyacetate, methyl 3-methoxypropionate, ethyl 3-ethoxypropionate, ethyl 3-methoxypropionate, 3-methoxybutyl acetate, 3-methoxypropyl acetate, 3-methyl-3-methoxybutyl acetate, 3-methyl-3-methoxybutyl propionate, 3-methyl-3-methoxybutyl butyrate, methyl acetoacetate, toluene, xylene, methyl ethyl ketone, methyl propyl ketone, methyl butyl ketone, 2-heptanone, 3-heptanone, 4-heptanone, cyclohexanone, N,N-dimethylformamide, N-methylacetamide, N,N-dimethylacetamide, N-methylpyrrolidone, 4-methyl-2-pentanol, and γ-butyrolactone. These solvents may be used singly or in combination of two or more of them.

Hereinafter, the use of the resist underlayer film forming composition of the present invention is described.

By using the resist underlayer film forming composition of the present invention, the resist underlayer film is formed by an coating method either on a substrate or on an organic underlayer film on a substrate, and on the resist underlayer film, a resist film (for example, a photoresist or an electron beam resist) is formed. Then, a resist pattern is formed by exposure and development. By dry etching the resist underlayer film using the resist pattern to transfer the pattern, the substrate is processed by the transferred pattern. Alternatively, by etching the organic underlayer film to transfer the pattern, the substrate is processed by the etched organic underlayer film.

In forming a fine pattern, for preventing a pattern collapse, the resist film thickness tends to become smaller. Due to the thinning of the resist, the dry etching for transferring the pattern to a film existing as an underlayer of the resist cannot transfer the pattern unless the etching rate of the underlayer film is higher than that of the upper layer film. An organic component film and an inorganic component film have significantly different dry etching rates from each other depending on the selection of the etching gas. The dry etching rate of the organic component film is enhanced by an oxygen-based gas and the dry etching rate of the inorganic component film is enhanced by using a halogen-containing gas.

Accordingly, for example, a resist pattern is formed and transferred to the resist underlayer film of the present invention existing as the underlayer of the resist pattern by dry etching the resist underlayer film with a halogen-containing gas, and the substrate is processed with a halogen-containing gas using the pattern transferred to the resist underlayer film. Alternatively, by dry etching the organic underlayer film existing as the underlayer of the resist underlayer film to which the pattern has been transferred with an oxygen-based gas using the resist underlayer film, the pattern is transferred to the organic underlayer film, and the substrate is processed with a halogen-containing gas using the organic underlayer film to which the pattern has been transferred.

The resist underlayer film forming composition of the present invention is applied onto a substrate used in the production of semiconductor devices (for example, silicon wafer substrates, substrates coated with silicon/silicon dioxide, silicon nitride substrates, glass substrates, ITO substrates, polyimide substrates, substrates coated with a low dielectric constant material (low-k material)) by an appropriate coating method such as a spinner and a coater and then, is baked to form a resist underlayer film. The baking conditions are appropriately selected from baking temperatures of 80° C. to 250° C. and baking time of 0.3 to 60 minutes. Preferably, the baking temperature is 150° C. to 250° C. and the baking time is 0.5 to 2 minutes. Here, the formed underlayer film has a film thickness of, for example, 10 to 1,000 nm, or 20 to 500 nm, or 50 to 300 nm, or 100 to 200 nm.

Next, on the resist underlayer film, for example, a photoresist layer is formed. The formation of the photoresist layer may be performed by a known method, that is, by applying a photoresist composition solution onto the underlayer film and by baking the composition solution. The photoresist has a film thickness of, for example, 50 to 10,000 nm, or 100 to 2,000 nm, or 200 to 1,000 nm.

In the present invention, after the organic underlayer film is formed on the substrate, the resist underlayer film may be formed from the composition of the present invention on the organic underlayer film and further, the resist underlayer film may be coated with the photoresist. Thus, even when the pattern width of the photoresist becomes smaller and the resist underlayer film is coated thinly with the photoresist for preventing a pattern collapse, the processing of the substrate may be performed by selecting an appropriate etching gas. For example, the resist underlayer film of the present invention may be processed with a fluorine-based gas as an etching gas having a sufficiently higher etching rate of the resist underlayer film than that of the photoresist, and the organic underlayer film may be processed with an oxygen-based gas as an etching gas having a sufficiently higher etching rate of the organic underlayer film than that of the resist underlayer film of the present invention. Furthermore, the substrate may be processed with a fluorine-based gas as an etching gas having a sufficiently higher etching rate of the substrate than that of the organic underlayer film.

The photoresist formed on the resist underlayer film of the present invention is not particularly limited so long as the photoresist is sensitive to light used for exposure, and both a negative-type photoresist and a positive-type photoresist may be used. Examples of the photoresist include: a positive-type photoresist made of a novolac resin and 1,2-naphthoquinonediazide sulfonic acid ester; a chemical amplification-type photoresist made of a binder having a group elevating the alkali dissolving rate by being decomposed by an acid, and a photoacid generator; a chemical amplification-type photoresist made of a low molecular compound elevating the alkali dissolving rate of the photoresist by being decomposed by an acid, an alkali-soluble binder, and a photoacid generator; and a chemical amplification-type photoresist made of a binder having a group elevating the alkali dissolving rate by being decomposed by an acid, a low molecular compound elevating the alkali dissolving rate of the photoresist by being decomposed by an acid, and a photoacid generator. Examples of the photoresist include trade name: APEX-E manufactured by Shipley Company, L.L.C., trade name: PAR710 manufactured by Sumitomo Chemical Co., Ltd., and trade name: SEPR430 manufactured by Shin-Etsu Chemical Co., Ltd. The examples also include fluorine atom-containing polymer-based photoresists described in Proc. SPIE, Vol. 3999, 330-334 (2000), Proc. SPIE, Vol. 3999, 357-364 (2000), and Proc. SPIE, Vol. 3999, 365-374 (2000).

Next, the exposure is performed through a predetermined mask. For the exposure, a KrF excimer laser (wavelength: 248 nm), an ArF excimer laser (wavelength: 193 nm), a F2 excimer laser (wavelength: 157 nm), or the like may be used. After exposure, if necessary, post exposure bake may also be performed. The post exposure bake is performed under conditions appropriately selected from baking temperatures of 70° C. to 150° C. and baking time of 0.3 to 10 minutes.

In the present invention, as the resist, a resist for electron beam lithography or a resist for EUV lithography may be used instead of the photoresist. As the electron beam resist, both a positive type and a negative type can be used. Examples of the electron beam resist include: a chemical amplification-type resist made of an acid generator and a binder having a group changing the alkali dissolving rate by being decomposed by an acid; a chemical amplification-type resist made of an alkali-soluble binder, an acid generator, and a low molecular compound changing the alkali dissolving rate of the resist by being decomposed by an acid; a chemical amplification-type resist made of an acid generator, a binder having a group changing the alkali dissolving rate by being decomposed by an acid, and a low molecular compound changing the alkali dissolving rate of the resist by being decomposed by an acid; a non-chemical amplification-type resist made of a binder having a group changing the alkali dissolving rate by being decomposed by an electron beam; and a non-chemical amplification-type resist made of a binder having a moiety changing the alkali dissolving rate by being broken by an electron beam. Also in the case of using such an electron beam resist, a resist pattern can be formed in a manner similar to that in the case of using a photoresist, by using an electron beam as an irradiation source.

As an EUV resist, a methacrylate resin-based resist may be used.

Next, the development is performed by using a developer (for example, an alkaline developer). Consequently, for example when a positive-type photoresist is used, the photoresist of an exposed part is removed to form a photoresist pattern.

Examples of the developer include alkaline aqueous solutions such as: aqueous solutions of alkali metal hydroxides such as potassium hydroxide and sodium hydroxide; aqueous solutions of quaternary ammonium hydroxides such as tetramethylammonium hydroxide, tetraethylammonium hydroxide, and choline; and aqueous solutions of amines such as ethanolamine, propylamine, and ethylenediamine. Furthermore, in these developers, a surfactant or the like may also be blended. The conditions for development are appropriately selected from temperatures of 5 to 50° C. and time of 10 to 600 seconds.

In the present invention, as the developer, an organic solvent may be used. After exposure, development is performed by using a developer (solvent). By development, for example when a positive-type photoresist is used, the photoresist of an unexposed part is removed to form a photoresist pattern. Examples of the developer include methyl acetate, butyl acetate, ethyl acetate, isopropyl acetate, amyl acetate, isoamyl acetate, ethyl methoxyacetate, ethyl ethoxyacetate, propylene glycol monomethyl ether acetate, ethylene glycol monoethyl ether acetate, ethylene glycol monopropyl ether acetate, ethylene glycol monobutyl ether acetate, ethylene glycol monophenyl ether acetate, diethylene glycol monomethyl ether acetate, diethylene glycol monopropyl ether acetate, diethylene glycol monoethyl ether acetate, diethylene glycol monophenyl ether acetate, diethylene glycol monobutyl ether acetate, diethylene glycol monoethyl ether acetate, 2-methoxybutyl acetate, 3-methoxybutyl acetate, 4-methoxybutyl acetate, 3-methyl-3-methoxybutyl acetate, 3-ethyl-3-methoxybutyl acetate, propylene glycol monomethyl ether acetate, propylene glycol monoethyl ether acetate, propylene glycol monopropyl ether acetate, 2-ethoxybutyl acetate, 4-ethoxybutyl acetate, 4-propoxybutyl acetate, 2-methoxypentyl acetate, 3-methoxypentyl acetate, 4-methoxypentyl acetate, 2-methyl-3-methoxypentyl acetate, 3-methyl-3-methoxypentyl acetate, 3-methyl-4-methoxypentyl acetate, 4-methyl-4-methoxypentyl acetate, propylene glycol diacetate, methyl formate, ethyl formate, butyl formate, propyl formate, ethyl lactate, butyl lactate, propyl lactate, ethyl carbonate, propyl carbonate, butyl carbonate, methyl pyruvate, ethyl pyruvate, propyl pyruvate, butyl pyruvate, methyl acetoacetate, ethyl acetoacetate, methyl propionate, ethyl propionate, propyl propionate, isopropyl propionate, methyl 2-hydroxypropionate, ethyl 2-hydroxypropionate, methyl 3-methoxypropionate, ethyl 3-methoxypropionate, ethyl 3-ethoxypropionate, and propyl 3-methoxypropionate. Furthermore, in these developers, a surfactant or the like may also be blended. The conditions for development are appropriately selected from temperatures of 5 to 50° C. and time of 10 to 600 seconds.

Then, using the thus formed pattern of the photoresist (upper layer) thus formed as a protecting film, the removal of the resist underlayer film (intermediate layer) of the present invention is performed and next, using the film composed of the patterned photoresist and the patterned resist underlayer film (intermediate layer) of the present invention as a protecting film, the removal of the organic underlayer film (underlayer) is performed. Finally, using the patterned resist underlayer film (intermediate layer) of the present invention and the patterned organic underlayer film (underlayer) as a protecting film, the processing of the semiconductor substrate is performed.

First, the resist underlayer film (intermediate layer) of the present invention at the part where the photoresist is removed is removed by dry etching to expose the semiconductor substrate.

For dry etching the resist underlayer film of the present invention, gases such as tetrafluoromethane ($CF_4$), perfluorocyclobutane($C_4F_8$), perfluoropropane ($C_3F_8$), trifluoromethane, carbon monoxide, argon, oxygen, nitrogen, sulfur hexafluoride, difluoromethane, nitrogen trifluoride, chlorine trifluoride, chlorine, trichloroborane, and dichloroborane may be used. For dry etching the resist underlayer film, a halogen-based gas is preferably used. By dry etching with a halogen-based gas, fundamentally, a photoresist that is composed of organic substances is difficult to be removed. On the contrary, the resist underlayer film of the present invention containing a large amount of silicon atoms is promptly removed by using a halogen-based gas. Therefore, the decrease of the film thickness of the photoresist according to dry etching of the resist underlayer film can be suppressed. As the result thereof, the photoresist may be used as a thin film. The resist underlayer film is dry-etched preferably with a fluorine-based gas and examples of the fluorine-based gas include tetrafluoromethane ($CF_4$), perfluorocyclobutane ($C_4F_8$), perfluoropropane ($C_3F_8$), trifluoromethane, and difluoromethane ($CH_2F_2$).

Subsequently, using the film composed of the patterned photoresist and the patterned resist underlayer film of the present invention as a protecting film, the removal of the organic underlayer film is performed. The removal of the organic underlayer film (underlayer) is performed by dry etching preferably with an oxygen-based gas. This is because the resist underlayer film of the present invention containing a large amount of silicon atoms is difficult to be removed by dry etching with an oxygen-based gas.

Finally, the processing of the semiconductor substrate is performed. The processing of the semiconductor substrate is performed by dry etching preferably with a fluorine-based gas.

Examples of the fluorine-based gas include tetrafluoromethane (CFA perfluorocyclobutane ($C_4F_8$), perfluoropropane ($C_3F_8$), trifluoromethane, and difluoromethane ($CH_2F_2$).

As an upper layer of the resist underlayer film of the present invention, an organic anti-reflective coating may be formed before the formation of the photoresist. The anti-reflective coating composition used here is not particularly limited and may be optionally selected to be used from the compositions commonly used in a conventional lithography process. The formation of the anti-reflective coating may be performed by a commonly used method, for example, by applying an anti-reflective coating composition by a spinner or a coater and by baking the composition.

The substrate onto which the resist underlayer film forming composition of the present invention is applied may also be a substrate having an organic or inorganic anti-reflective coating formed by a CVD method on its surface and, on the anti-reflective coating, the underlayer film of the present invention can also be formed.

A resist underlayer film formed from the resist underlayer film forming composition of the present invention may absorb light used in a lithography process depending on the wavelength of light. Then, in such a case, the resist underlayer film can function as an anti-reflective coating having the effect of preventing light reflected on the substrate. Furthermore, the underlayer film of the present invention may also be used as a layer for preventing an interaction between the substrate and the photoresist, a layer having a function of preventing an adverse action of a material used in the photoresist or of a substance generated during exposure of the photoresist against the substrate, a layer having a function of preventing the diffusion of a substance generated in or on the substrate during heating and baking to the upper layer photoresist, a barrier layer for reducing a poisoning effect to the photoresist layer by a semiconductor substrate dielectric layer, and the like.

A resist underlayer film formed from the resist underlayer film forming composition may be applied to a substrate in which a via hole used in the dual damascene process is formed to be used as an embedding material capable of filling the hole without any void. The resist underlayer film may also be used as a planarizing material for planarizing the surface of a semiconductor substrate having unevenness.

The above resist underlayer film may be used as an underlayer film of an EUV resist also for the following purpose besides the purpose of the function as a hardmask. The above resist underlayer film forming composition may be used as an EUV resist underlayer anti-reflective coating capable of preventing a reflection of exposure light undesirable during EUV exposure (wavelength: 13.5 nm) such as UV and DUV (ArF light and KrF light) on the substrate or the interface as an underlayer film of an EUV resist without causing intermixing with the EUV resist. The above resist underlayer film forming composition can efficiently prevent light reflection as an underlayer of an EUV resist. When the above resist underlayer film forming composition is used as the EUV resist underlayer film, the process can be performed in a manner similar to that in the case of an underlayer film for a photoresist.

Further, the present invention relates also to a novel silane compound of Formula (A). In Formula (A), $R^1$ is an organic group containing a group of Formula (A-1), Formula (A-2), or Formula (A-3) and in a group of Formula (A-1), Formula (A-2), or Formula (A-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups and atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is independently a hydrogen atom an alkyl group, an alkenyl group, or a hydrolyzable silyl group bonded optionally through an alkylene group; and $T^{11}$ is an alkylene group and is bonded to a silicon atom through a Si—C bond. $R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group, and is bonded to a silicon atom through a Si—C bond. $R^3$ is an alkoxy group, an acyloxy group, or a halogen group. $a_a$ is an integer of 1 and $b_a$ is an integer of 0 or 1, where $a_a+b_a$ is an integer of 1 or 2.

Examples of the alkylene group, the cyclic alkylene group, the alkenylene group, the arylene group, the sulfur atom, the oxygen atom, the oxycarbonyl group, the amido group, the secondary amino group, the tertiary amino group, the alkylidyne group, the alkanetriyl group, the alkyl group, the aryl group, the halogenated alkyl group, the halogenated aryl group, the alkenyl group, or the organic group having an epoxy group, an acryloyl group, a methacryloyl group, a mercapto group, an amino group, or a cyano group include the above-exemplified examples of each group.

EXAMPLES

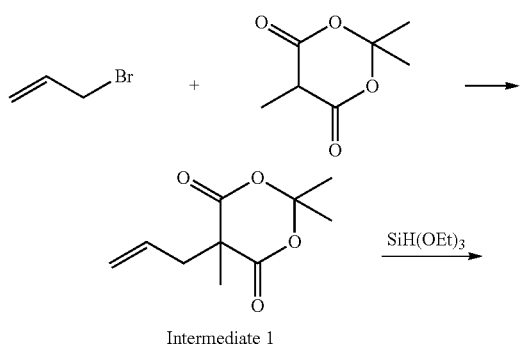

(Synthesis of Compound 1)

Intermediate 1

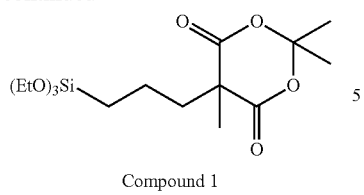

Compound 1

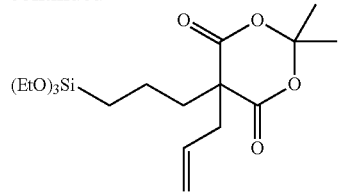

Compound 2

Into a 200 mL four-neck flask equipped with a magnetic stirrer, 20.00 g of 2,2,5-trimethyl-1,3-dioxane-4,6-dione, 26.22 g of potassium carbonate, and 200.00 g of dimethylformamide were charged and into the resultant reaction mixture, 15.30 g of allyl bromide was added dropwise at room temperature and at room temperature, the reaction was progressed overnight. Then, an extraction operation of the reaction mixture was performed using ethyl acetate and water and the resultant organic phase was dried over magnesium sulfate, followed by concentrating and drying the organic phase by an evaporator. The resultant crude product was purified by distillation under reduced pressure to obtain an intermediate 1.

$^1$H-NMR (500 MHz) in DMSO-$d_6$: 1.55 ppm (s, 3H), 1.67 ppm (s, 3H), 1.71 ppm (s, 3H), 2.64 ppm (d, 2H), 5.10-5.16 ppm (m, 2H), 5.56-5.62 ppm (m, 1H)

Into a 200 mL four-neck flask equipped with a magnetic stirrer, 12.00 g of intermediate 1, 2.31 g of Karstedt's catalyst solution (a 2% by weight xylene solution of a platinum(0)-1,3-divinyl-1,1,3,3-tetramethyldisiloxane complex), and 90 g of toluene were charged and into the resultant reaction mixture, 10.94 g of triethoxysilane was added dropwise over 10 minutes. At room temperature, the resultant reaction mixture was stirred for 5 hours and the reaction liquid was concentrated and dried, followed by purifying the resultant crude product by distillation under reduced pressure to obtain a compound 1. An NMR spectrum of the compound 1 is shown in FIG. 1.

$^1$H-NMR (500 MHz) in DMSO-$d_6$: 0.53 ppm (t, 2H), 1.13 ppm (t, 6H), 1.21 ppm (quint, 2H), 1.52 ppm (s, 3H), 1.69 ppm (s, 3H), 1.71 ppm (s, 3H), 1.93 ppm (t, 2H), 3.72 ppm (q, 6H)

(Synthesis of Compound 2)

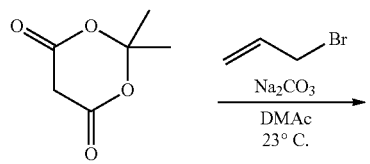

Molecular weight: 144.13

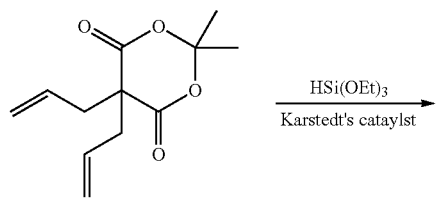

Figure 2:
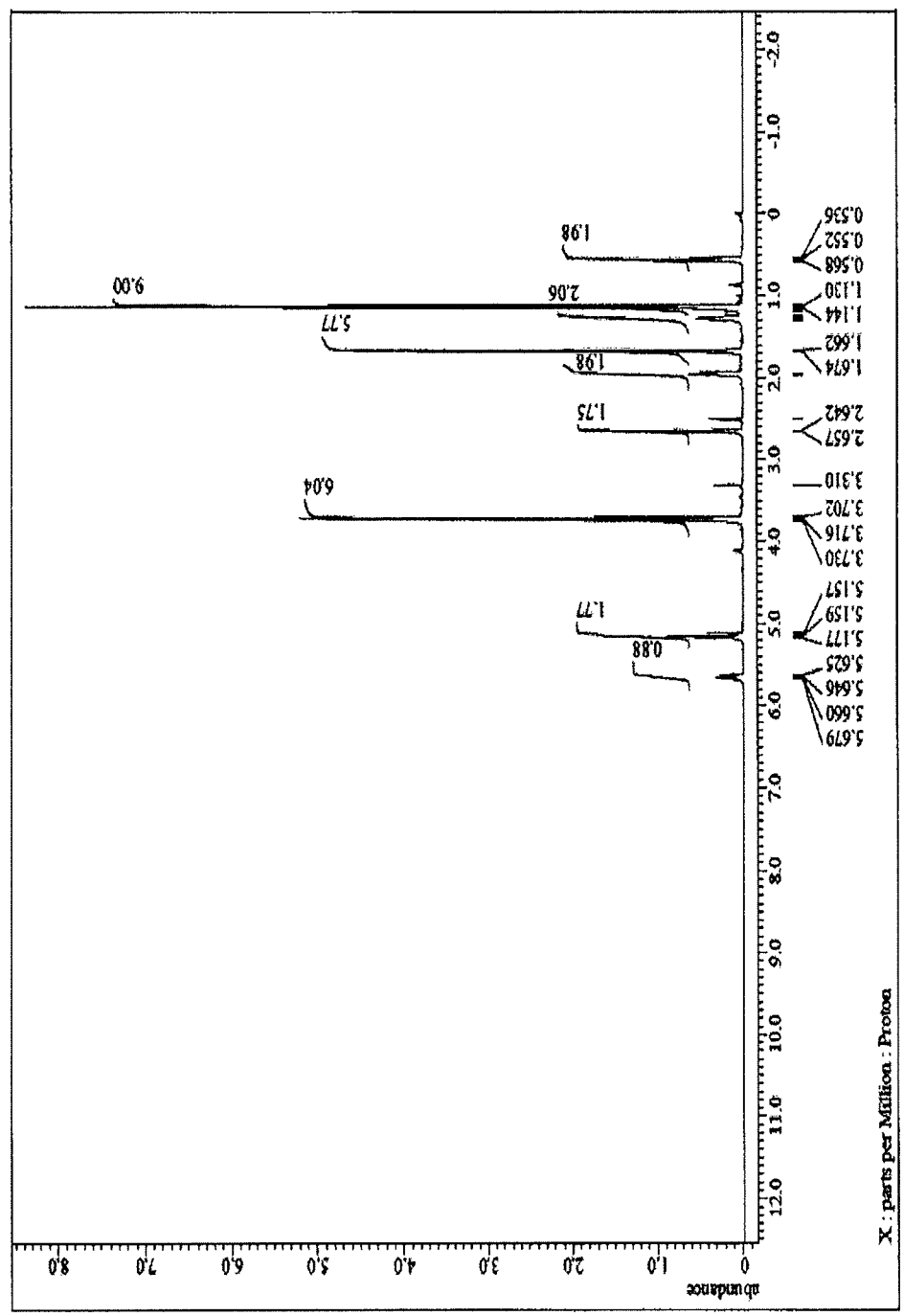
FIG. 2 shows an NMR spectrum of a compound 2.

Into an egg-plant shaped flask, 10.0 g of 2,2-dimethyl-1,3-dioxane-4,6-dione, 17.6 g of allyl bromide, 15.4 g of sodium carbonate, and 40.0 g of dimethyl acetamide were charged and the resultant reaction mixture was stirred at 23° C. Then, the reaction mixture was extracted and concentrated. To the resultant concentrate, 11.4 g of triethoxysilane, 1.0 g of Karstedt's catalyst (2% xylene solution), and 40.0 g of toluene were added to perform hydrosilylation to obtain a crude product. By distilling the crude product under reduced pressure, a compound 2 as the objective product was obtained. An NMR spectrum of the compound 2 is shown in FIG. 2.

$^1$H-NMR (500 MHz, DMSO-$d_6$): 0.55 ppm (t, 2H), 1.13 ppm (t, 9H), 1.28 ppm (m, 2H), 1.66 ppm (s, 3H), 1.67 ppm (s, 3H), 1.96 ppm (m, 2H), 2.65 ppm (d, 2H), 3.72 ppm (q, 6H), 5.13-5.18 ppm (m, 2H), 5.63-5.67 ppm (m, 1H)

(Synthesis of Compound 3)

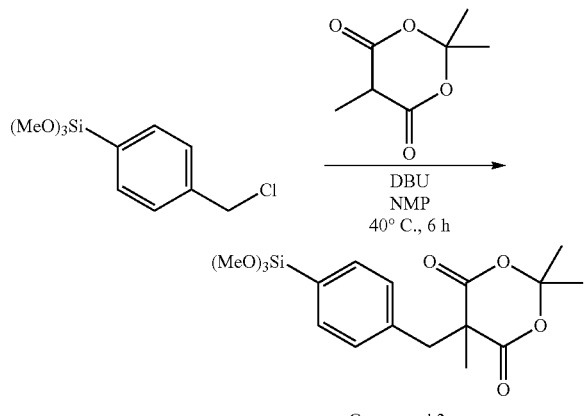

Compound 3

Figure 3:
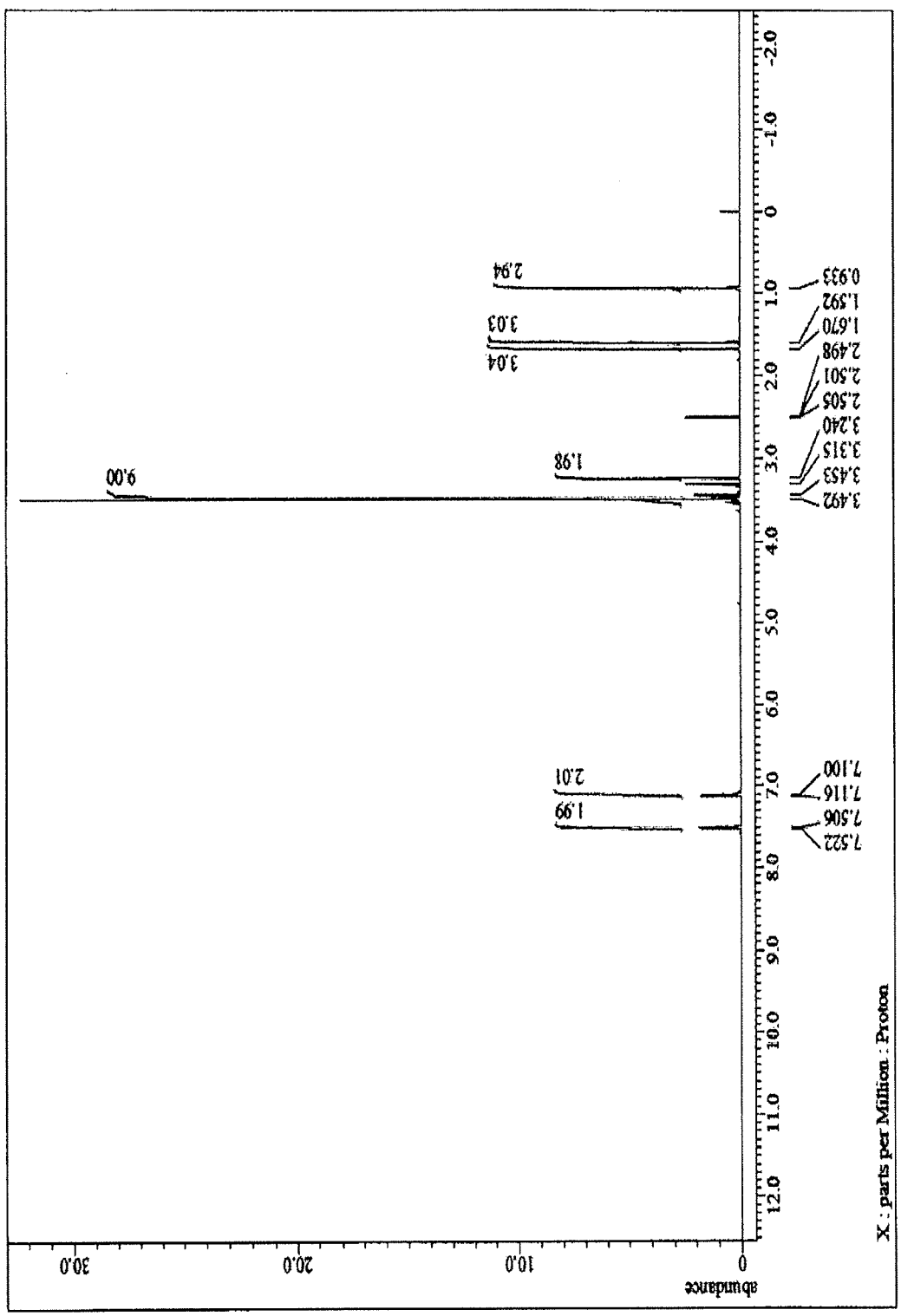
FIG. 3 shows an NMR spectrum of a compound 3.

Into a 100 mL egg-plant shaped flask, 10.00 g (0.0405 mol) of (p-chloromethyl)phenyltrimethoxysilane and 1.0 g of N-methylpyrrolidone were charged and the resultant reaction mixture was heated to 40° C. Thereinto, a solution in which 7.69 g (0.0486 mol) of 2,2,5-trimethyl-1,3-dioxane-4,6-dione, 7.40 g (0.0486 mol) of 1,8-diazabicyclo[5.4.0]undeca-7-ene, and 19.0 g of N-methylpyrrolidone were mixed was added dropwise and the reaction was progressed for 6 hours. The reaction liquid was subjected to phase separation using toluene and water and toluene was removed by an evaporator to obtain a crude product. The crude product was subjected to distillation under reduced pressure and recrystallization to obtain a compound 3 as the objective product. An NMR spectrum of the compound 3 is shown in FIG. 3.

$^1$H-NMR (500 MHz, DMSO-$d_6$): 0.93 ppm (s, 3H), 1.59 ppm (s, 3H), 1.67 ppm (s, 3H), 3.24 ppm (s, 2H), 3.49 ppm (s, 9H), 7.11 (d, 2H), 7.51 ppm (d, 2H)

(Synthesis of Compound 4)

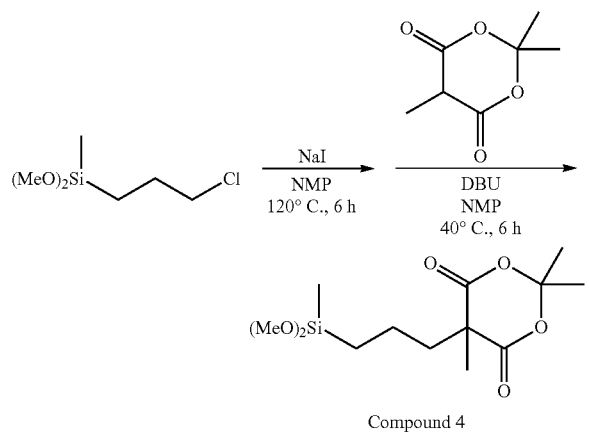

Compound 4

Figure 4:
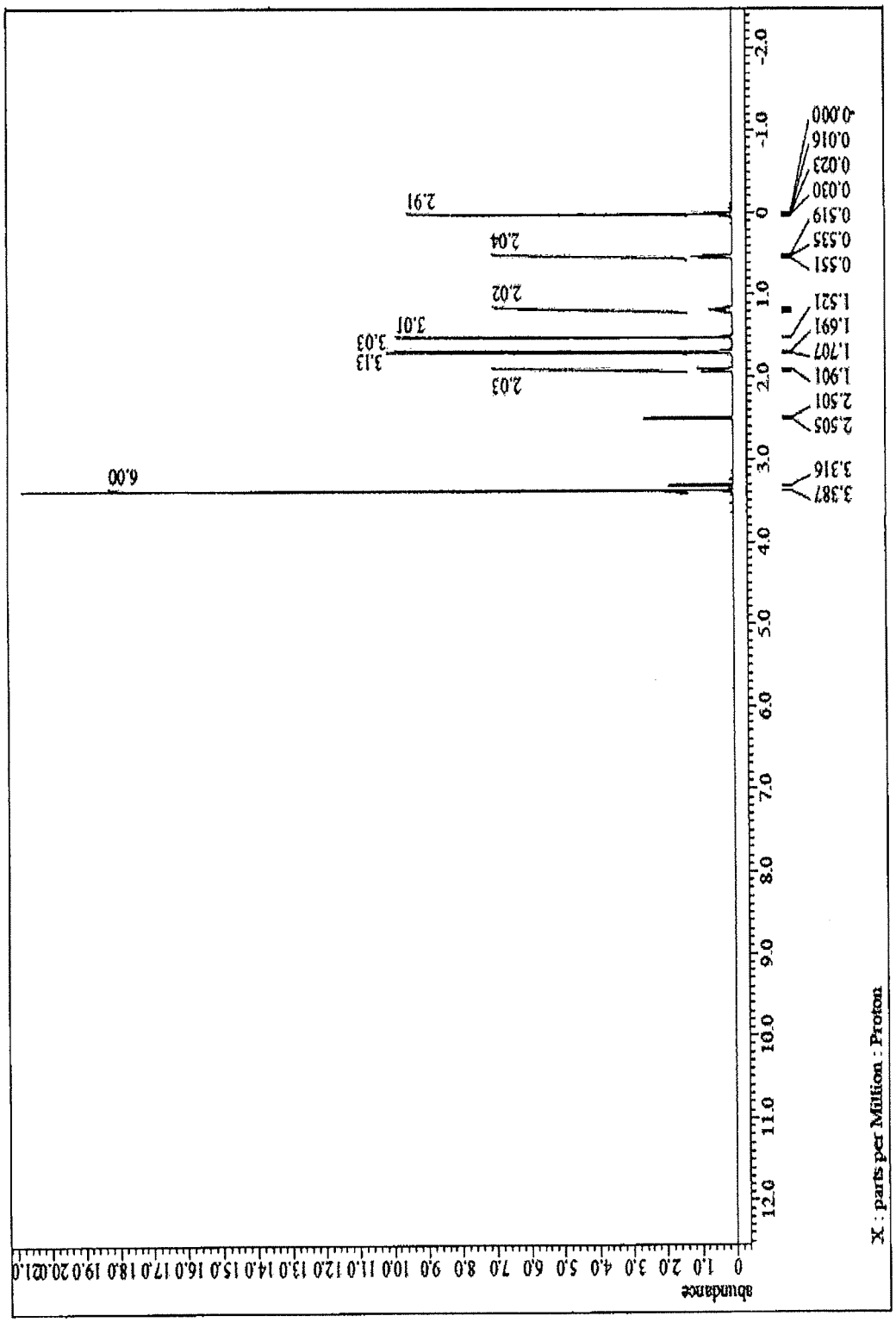
FIG. 4 shows an NMR spectrum of a compound 4.

Into a 100 mL egg-plant shaped flask, 10.00 g (0.0547 mol) of 3-chloropropylmethyldimethoxysilane, 9.84 g (0.0657 mol) of NaI, and 1.0 g of N-methylpyrrolidone were charged and the resultant reaction mixture was heated at 120° C. for 6 hours. Thereinto, after the temperature is decreased to 40° C., a solution in which 10.36 g (0.0657 mol) of 2,2,5-trimethyl-1,3-dioxane-4,6-dione, 10.00 g (0.0657 mol) of 1,8-diazabicyclo[5.4.0]undeca-7-ene, and 19.0 g of N-methylpyrrolidone were mixed was added dropwise and the reaction was progressed for 6 hours. The reaction liquid was subjected to phase separation using toluene and water and toluene was removed by an evaporator to obtain a crude product. The crude product was subjected to distillation under reduced pressure and recrystallization to obtain a compound 4 as the objective product. An NMR spectrum of the compound 4 is shown in FIG. 4.

$^1$H-NMR (500 MHz, DMSO-$d_6$): 0.02 ppm (s, 3H), 0.54 ppm (t, 2H), 1.19 ppm (m, 2H), 1.52 ppm (s, 3H), 1.69 ppm (s, 3H), 1.71 ppm (s, 3H), 0.1.91 ppm (m, 2H), 3.34 ppm (s, 6H)

Synthesis Example 1

14.76 g (70 mol % in all silanes) of tetraethoxysilane, 2.71 g (15 mol % in all silanes) of methyltriethoxysilane, 2.01 g (10 mol % in all silanes) of phenyltrimethoxysilane, 1.83 g (5 mol % in all silanes) of the compound 1, and 31.95 g of acetone were charged into a 100 mL flask. While the resultant mixture solution was stirred with a magnetic stirrer, 6.75 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-1)) had a weight-average molecular weight measured by GPC of Mw 1,500 in terms of polystyrene.

Synthesis Example 2

15.29 g (75 mol % in all silanes) of tetraethoxysilane, 1.22 g (7 mol % in all silanes) of methyltriethoxysilane, 1.36 g (7 mol % in all silanes) of phenyltrimethoxysilane, 1.71 g (6 mol % in all silanes) of methylsulfonyl methylphenyl trimethoxysilane, 1.77 g (5 mol % in all silanes) of the compound 1, and 32.03 g of acetone were charged into a 100 mL flask. While the resultant mixture solution was stirred with a magnetic stirrer, 6.61 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-2)) had a weight-average molecular weight measured by GPC of Mw 1,500 in terms of polystyrene.

Synthesis Example 3

15.29 g (70 mol % in all silanes) of tetraethoxysilane, 4.49 g (24 mol % in all silanes) of methyltriethoxysilane, 1.04 g (5 mol % in all silanes) of phenyltrimethoxysilane, 0.38 g (1 mol % in all silanes) of the compound 1, and 31.80 g of acetone were charged into a 100 mL flask. While the resultant mixture solution was stirred with a magnetic stirrer, 6.99 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-1)) had a weight-average molecular weight measured by GPC of Mw 1,500 in terms of polystyrene.

Synthesis Example 4

15.53 g (75 mol % in all silanes) of tetraethoxysilane, 3.37 g (19 mol % in all silanes) of methyltriethoxysilane, 2.06 g (5 mol % in all silanes) of 3-(triethoxysilylpropyl)diallyl isocyanurate, 0.36 g (1 mol % in all silanes) of the compound 1, and 31.97 g of acetone were charged into a 100 mL flask. While the resultant mixture solution was stirred with a magnetic stirrer, 6.72 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-3)) had a weight-average molecular weight measured by GPC of Mw 1,600 in terms of polystyrene.

Synthesis Example 5

15.19 g (75 mol % in all silanes) of tetraethoxysilane, 1.21 g (7 mol % in all silanes) of methyltriethoxysilane, 1.35 g (7 mol % in all silanes) of phenyltrimethoxysilane, 1.70 g (6 mol % in all silanes) of methylsulfonyl methylphenyl trimethoxysilane, 1.23 g (3 mol % in all silanes) of di-tert-butyl 2-(3-triethoxysilyl)propyl)malonate, 0.70 g (2 mol % in all silanes) of the compound 1, and 32.06 g of acetone were charged into a 100 mL flask. While the resultant mixture solution was stirred with a magnetic stirrer, 6.57 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-7)) had a weight-average molecular weight measured by GPC of Mw 1,500 in terms of polystyrene.

Synthesis Example 6

15.60 g (75 mol % in all silanes) of tetraethoxysilane, 1.78 g (10 mol % in all silanes) of methyltriethoxysilane, 1.98 g (10 mol % in all silanes) of phenyltrimethoxysilane, 1.94 g (5 mol % in all silanes) of the compound 2 and 31.95 g of acetone were charged into a 100 mL flask. While the resultant mixture solution was stirred with a magnetic stirrer, 6.74 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-8)) had a weight-average molecular weight measured by GPC of Mw 1,500 in terms of polystyrene.

Synthesis Example 7

15.48 g (75 mol % in all silanes) of tetraethoxysilane, 1.77 g (10 mol % in all silanes) of methyltriethoxysilane, 1.57 g (8 mol % in all silanes) of phenyltrimethoxysilane, 0.58 g (2 mol % in all silanes) of methylsulfonyl methylphenyl trimethoxysilane, 1.93 g (5 mol % in all silanes) of the compound 2 and 31.98 g of acetone were charged into a 100 mL flask. While the resultant mixture solution was stirred with a magnetic stirrer, 6.70 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-9)) had a weight-average molecular weight measured by GPC of Mw 1,500 in terms of polystyrene.

Synthesis Example 8

15.73 g (75 mol % in all silanes) of tetraethoxysilane, 2.69 g (15 mol % in all silanes) of methyltriethoxysilane, 1.00 g (5 mol % in all silanes) of phenyltrimethoxysilane, 1.85 g (5 mol % in all silanes) of the compound 3, and 31.92 g of acetone were charged into a 100 mL flask. While the resultant mixture solution was stirred with a magnetic stirrer, 6.80 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-10)) had a weight-average molecular weight measured by GPC of Mw 1,500 in terms of polystyrene.

Synthesis Example 9

15.80 g (75 mol % in all silanes) of tetraethoxysilane, 3.61 g (20 mol % in all silanes) of methyltriethoxysilane, 1.86 g (5 mol % in all silanes) of the compound 3, and 31.90 g of acetone were charged into a 100 mL flask. While the resultant mixture solution was stirred with a magnetic stirrer, 6.83 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-11)) had a weight-average molecular weight measured by GPC of Mw 1,500 in terms of polystyrene.

Synthesis Example 10

15.90 g (75 mol % in all silanes) of tetraethoxysilane, 1.81 g (10 mol % in all silanes) of methyltriethoxysilane, 2.02 g (10 mol % in all silanes) of phenyltrimethoxysilane, 1.55 g (5 mol % in all silanes) of the compound 4, and 31.93 g of acetone were charged into a 100 mL flask. While the resultant mixture solution was stirred with a magnetic stirrer, 6.79 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-12)) had a weight-average molecular weight measured by GPC of Mw 1,500 in terms of polystyrene.

Synthesis Example 11

16.06 g (90 mol % in all silanes) of tetraethoxysilane, 0.85 g (5 mol % in all silanes) of phenyltrimethoxysilane, 1.55 g (5 mol % in all silanes) of the compound 1, and 27.69 g of methanol were charged into a 100 mL flask. While the resultant mixture solution was stirred with a magnetic stirrer, 0.01 g of a 70% nitric acid and 13.85 g of ultrapure water were added dropwise into the mixture solution. After the completion of the addition, the flask was transferred into an oil bath adjusted to 40° C. and the reaction was progressed for 12 hours. Then, to the reaction solution, 70 g of propylene glycol monoethyl ether was added. From the resultant reaction solution, methanol and ethanol as reaction by-products and water were distilled off under reduced pressure and the resultant reaction mixture was concentrated to obtain a hydrolysis-condensation product (polymer) propylene glycol monoethyl ether solution. The content of a solid residue in the obtained hydrolysis-condensation product (polymer) propylene glycol monoethyl ether solution at 140° C. was 12% by weight. The obtained polymer (corresponding to Formula (4-13)) had a weight-average molecular weight measured by GPC of Mw 1,700 in terms of polystyrene.

Synthesis Example 12

16.77 g (90 mol % in all silanes) of tetraethoxysilane, 0.80 g (5 mol % in all silanes) of methyltriethoxysilane, 0.89 g (5 mol % in all silanes) of phenyltrimethoxysilane, and 27.69 g of methanol were charged into a 100 mL flask. While the resultant mixture solution was stirred with a magnetic stirrer, 0.01 g of a 70% nitric acid and 13.85 g of ultrapure water were added dropwise into the mixture solution. After the completion of the addition, the flask was transferred into an oil bath adjusted to 40° C. and the reaction was progressed for 12 hours. Then, to the reaction solution, 70 g of propylene glycol monoethyl ether was added. From the resultant reaction solution, methanol and ethanol as reaction by-products and water were distilled off under reduced pressure and the resultant reaction mixture was concentrated to obtain a hydrolysis-condensation product (polymer) propylene glycol monoethyl ether solution. The content of a solid residue in the obtained hydrolysis-condensation product (polymer) propylene glycol monoethyl ether solution at 140° C. was 12% by weight. The obtained polymer (corresponding to Formula (E-1)) had a weight-average molecular weight measured by GPC of Mw 1,700 in terms of polystyrene.

Synthesis Example 13

15.43 g (75 mol % in all silanes) of tetraethoxysilane, 1.41 g (8 mol % in all silanes) of methyltriethoxysilane, 1.76 g (9 mol % in all silanes) of phenyltrimethoxysilane, 0.94 g (3 mol % in all silanes) of 3-tosylpropyltrimethoxysilane, 1.79 g (5 mol % in all silanes) of the compound 1, and 32.06 g of acetone were charged into a 100 mL flask. While the resultant mixture solution was stirred with a magnetic stirrer, 6.57 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-14)) had a weight-average molecular weight measured by GPC of Mw 1,500 in terms of polystyrene.

Synthesis Example 14

15.40 g (75 mol % in all silanes) of tetraethoxysilane, 1.58 g (9 mol % in all silanes) of methyltriethoxysilane, 1.37 g (7 mol % in all silanes) of phenyltrimethoxysilane, 1.20 g (4 mol % in all silanes) of 3-phenylsulfonylpropyltrimethoxysilane, 1.79 g (5 mol % in all silanes) of the compound 1, and 32.06 g of acetone were charged into a 100 mL flask. While the resultant mixture solution was stirred with a magnetic stirrer, 6.66 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (4-15)) had a weight-average molecular weight measured by GPC of Mw 1,500 in terms of polystyrene.

Comparative Synthesis Example 1

15.35 g (70 mol % in all silanes) of tetraethoxysilane, 3.75 g (20 mol % in all silanes) of methyltriethoxysilane, 2.09 g (10 mol % in all silanes) of phenyltrimethoxysilane, and 31.79 g of acetone were charged into a 100 mL flask. While the resultant mixture solution was stirred with a magnetic stirrer, 7.02 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-1)) had a weight-average molecular weight measured by GPC of Mw 1,500 in terms of polystyrene.

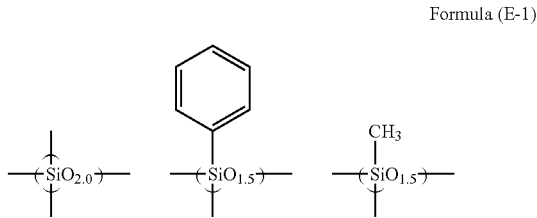

Formula (E-1)

Comparative Synthesis Example 2

15.42 g (70 mol % in all silanes) of tetraethoxysilane, 4.71 g (25 mol % in all silanes) of methyltriethoxysilane, 1.05 g (5 mol % in all silanes) of phenyltrimethoxysilane, and 31.77 g of acetone were charged into a 100 mL flask. While the resultant mixture solution was stirred with a magnetic stirrer, 7.05 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-1)) had a weight-average molecular weight measured by GPC of Mw 1,500 in terms of polystyrene.

Comparative Synthesis Example 3

15.65 g (75 mol % in all silanes) of tetraethoxysilane, 3.57 g (20 mol % in all silanes) of methyltriethoxysilane, 2.07 g (5 mol % in all silanes) of 3-(triethoxysilylpropyl)diallyl isocyanurate, and 31.94 g of acetone were charged into a 100 mL flask. While the resultant mixture solution was stirred with a magnetic stirrer, 6.77 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-2)) had a weight-average molecular weight measured by GPC of Mw 1,600 in terms of polystyrene.

Formula (E-2)

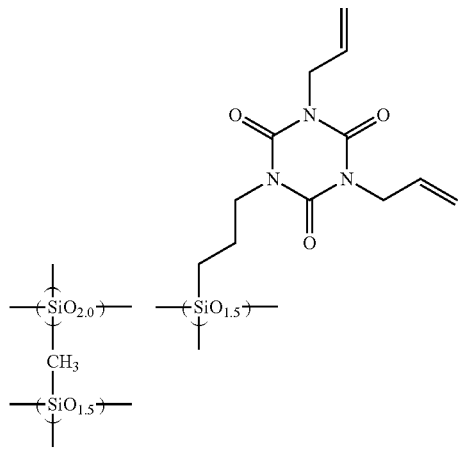

Comparative Synthesis Example 4

4.24 g (20 mol % in all silanes) of tetraethoxysilane, 3.63 g (20 mol % in all silanes) of methyltriethoxysilane, 10.10 g (50 mol % in all silanes) of phenyltrimethoxysilane, 3.69 g (10 mol % in all silanes) of the compound 1, and 32.48 g of acetone were charged into a 100 mL flask. While the resultant mixture solution was stirred with a magnetic stirrer, 5.87 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 22 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-3)) had a weight-average molecular weight measured by GPC of Mw 900 in terms of polystyrene.

Formula (E-3)

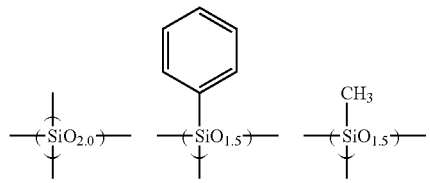

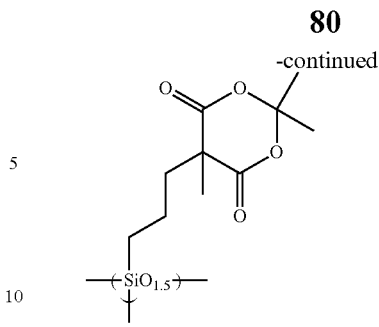

Comparative Synthesis Example 5

4.37 g (20 mol % in all silanes) of tetraethoxysilane, 3.74 g (20 mol % in all silanes) of methyltriethoxysilane, 10.41 g (50 mol % in all silanes) of phenyltrimethoxysilane, 3.05 g (10 mol % in all silanes) of methylsulfonyl methylphenyl trimethoxysilane, and 32.37 g of acetone were charged into a 100 mL flask. While the resultant mixture solution was stirred with a magnetic stirrer, 6.05 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-4)) had a weight-average molecular weight measured by GPC of Mw 1,000 in terms of polystyrene.

Formula (E-4)

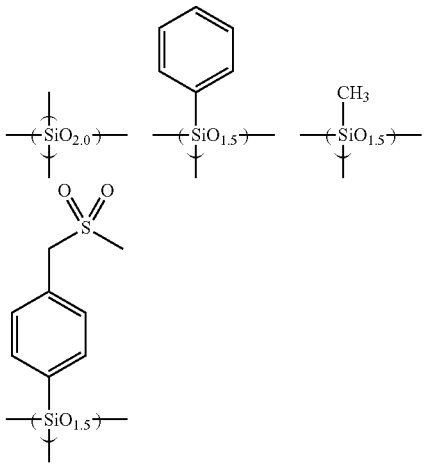

Comparative Synthesis Example 6

4.15 g (20 mol % in all silanes) of tetraethoxysilane, 3.55 g (20 mol % in all silanes) of methyltriethoxysilane, 9.88 g (50 mol % in all silanes) of phenyltrimethoxysilane, 4.12 g (10 mol % in all silanes) of 3-(triethoxysilylpropyl)diallyl isocyanurate, and 32.55 g of acetone were charged into a 100 mL flask. While the resultant mixture solution was stirred with a magnetic stirrer, 5.75 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 21 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-5)) had a weight-average molecular weight measured by GPC of Mw 1,000 in terms of polystyrene.

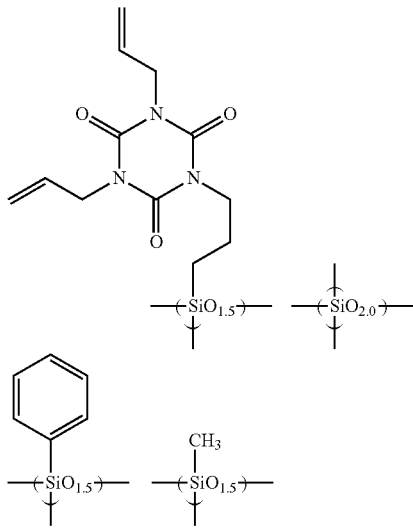

Formula (E-5)

Comparative Synthesis Example 7

4.31 g (20 mol % in all silanes) of tetraethoxysilane, 3.69 g (20 mol % in all silanes) of methyltriethoxysilane, 10.25 g (50 mol % in all silanes) of phenyltrimethoxysilane, 1.50 g (5 mol % in all silanes) of methylsulfonyl methylphenyl trimethoxysilane, 1.87 g (5 mol % in all silanes) of the compound 1 and 32.42 g of acetone were charged into a 100 mL flask. While the resultant mixture solution was stirred with a magnetic stirrer, 5.96 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 22 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (E-6)) had a weight-average molecular weight measured by GPC of Mw 900 in terms of polystyrene.

Formula (E-6)

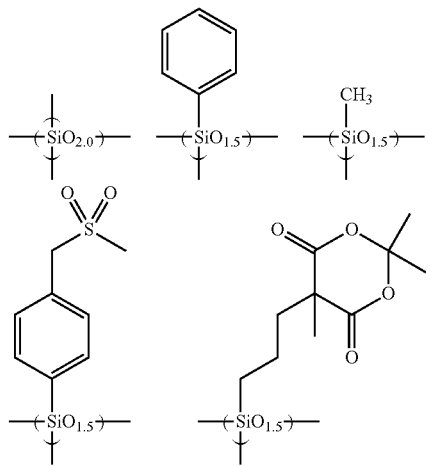

(Synthesis of Additive 1)

8.32 g (70 mol % in all silanes) of methyltriethoxysilane, 7.25 g (30 mol % in all silanes) of the compound 1, and 23.36 g of acetone were charged into a 100 mL flask. While the resultant mixture solution was stirred with a magnetic stirrer, 3.60 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 32 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (F-1)) had a weight-average molecular weight measured by GPC of Mw 1,000 in terms of polystyrene.

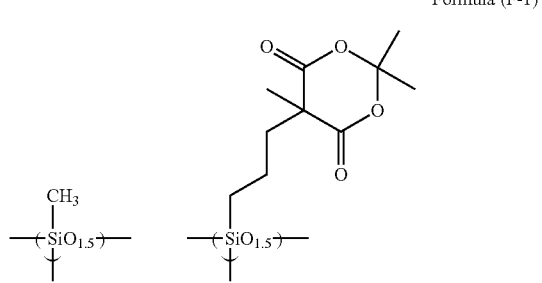

Formula (F-1)

(Synthesis of Additive 2)

9.36 g (70 mol % in all silanes) of methyltriethoxysilane, 5.44 g (20 mol % in all silanes) of the compound 1, 2.18 g (10 mol % in all silanes) of methylsulfonyl methylphenyl trimethoxysilane, and 25.46 g of acetone were charged into a 100 mL flask. While the resultant mixture solution was stirred with a magnetic stirrer, 4.05 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 32 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (F-2)) had a weight-average molecular weight measured by GPC of Mw 1,500 in terms of polystyrene.

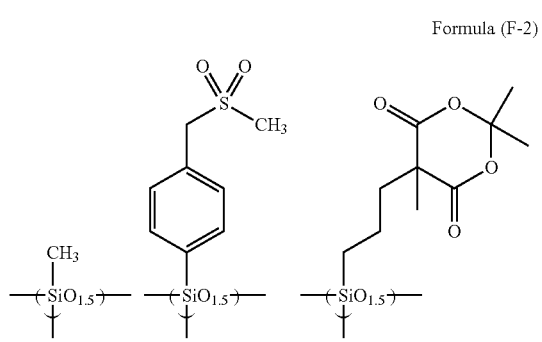

Formula (F-2)

(Synthesis of Additive 3)

9.36 g (70 mol % in all silanes) of methyltriethoxysilane, 5.44 g (20 mol % in all silanes) of the compound 1, 2.43 g (10 mol % in all silanes) of 3-((2-methoxyethoxy)methoxy)-2-methyl propyl)triethoxysilane, and 25.85 g of acetone were charged into a 100 mL flask. While the resultant mixture solution was stirred with a magnetic stirrer, 4.05 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 32 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (F-3)) had a weight-average molecular weight measured by GPC of Mw 1,200 in terms of polystyrene.

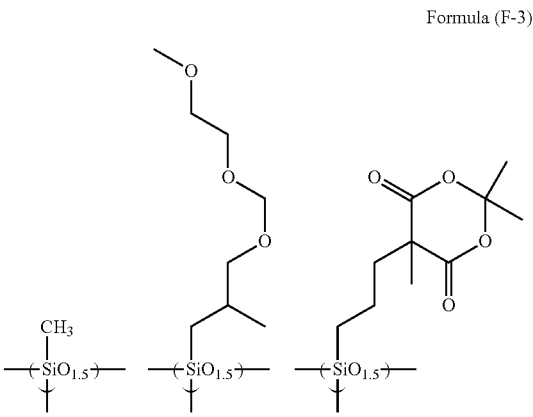

Formula (F-3)

(Synthesis of Additive 4)

Into a 200 mL flask equipped with a stirrer, a thermometer, and a condenser tube, 4.07 g of a 35% by weight tetramethylammonium hydroxide aqueous solution and 28.94 g of acetone were charged to prepare a reaction solvent. A mixture solution of 6.02 g (70 mol % in all silanes) of methyl triethoxysilane, 4.18 g (30 mol % in all silanes) of methylsulfonyl methylphenyl trimethoxysilane, and 4.18 g of acetone was prepared. While the reaction solvent was stirred with a magnetic stirrer, the mixture solution was added dropwise into the reaction solvent at room temperature. After the completion of the addition, while maintaining the temperature of the resultant reaction mixture at 40° C. using an oil bath, the reaction was progressed for 240 minutes and then the reaction mixture was cooled down to room temperature, followed by adding 2 mol % hydrochloric acid to the reaction mixture to neutralize the reaction mixture. To the reaction liquid, 70 mL of ethyl acetate and 70 mL of water were added and the resultant reaction mixture was shaken, followed by subjecting the reaction mixture to phase separation into two phases. Further, the organic phase was washed with 70 mL of water three times. To the resultant organic phase, 12 g of propylene glycol monomethyl ether acetate was added and from the organic phase, methanol and ethanol as reaction by-products and water were distilled off under reduced pressure. The resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 20% by weight at 160° C. The obtained polymer (corresponding to Formula (F-4)) had a weight-average molecular weight measured by GPC of Mw 6,200 in terms of polystyrene.

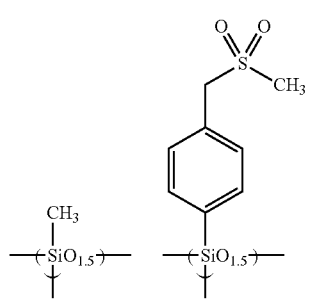

Formula (F-4)

(Synthesis of Additive 5)

22.85 g (70 mol % in all silanes) of methyltriethoxysilane, 13.27 g (20 mol % in all silanes) of the compound 1, 5.39 g (10 mol % in all silanes) of (1-ethoxyethoxy)propyl trimethoxysilane, and 62.27 g of propylene glycol monopropyl ether were charged into a 200 mL flask. While the resultant mixture solution was stirred with a magnetic stirrer, 0.03 g of tert-butylamine and 11.52 g of water were added dropwise into the mixture solution slowly over 30 minutes. After the completion of the addition, the flask was transferred into an oil bath adjusted to 40° C. and the reaction was progressed for 12 hours. Then, to the reaction solution, 155 g of propylene glycol monoethyl ether was added. From the resultant reaction solution, methanol and ethanol as reaction by-products, water, and tert-butylamine were distilled off under reduced pressure and the resultant reaction mixture was concentrated to obtain a hydrolysis-condensation product (polymer) propylene glycol monoethyl ether solution. In the obtained hydrolysis-condensation product (polymer) propylene glycol monoethyl ether solution, the content of a solid residue was 10% by weight at 140° C. The obtained polymer (corresponding to Formula (F-5)) had a weight-average molecular weight measured by GPC of Mw 1,800 in terms of polystyrene.

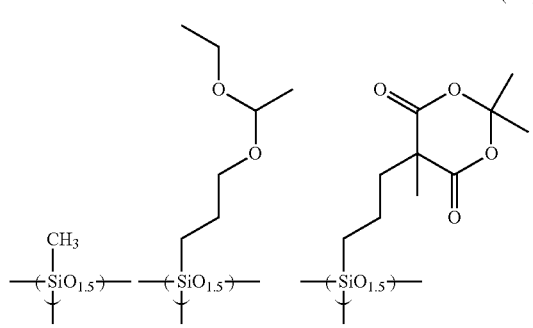

Formula (F-5)

(Synthesis of Additive 6)

12.00 g (70 mol % in all silanes) of methyltriethoxysilane, 6.97 g (20 mol % in all silanes) of the compound 1, 2.95 g (10 mol % in all silanes) of triethoxy(3-((tetrahydro-2H-pyran-2-yl)oxy)propyl)silane, and 32.88 g of acetone were charged into a 100 mL flask. While the resultant mixture solution was stirred with a magnetic stirrer, 5.20 g of a 0.01 mol/L hydrochloric acid was added dropwise into the mixture solution. After the completion of the addition, the flask was transferred into an oil bath adjusted to 85° C., and under warming-reflux, the reaction was progressed for 240 minutes. Then, the reaction solution was cooled down to room temperature and to the reaction solution, 44 g of propylene glycol monomethyl ether acetate was added. From the resultant reaction solution, ethanol as a reaction by-product, water, and hydrochloric acid were distilled off under reduced pressure and the resultant reaction mixture was concentrated to obtain a hydrolysis-condensation product (polymer) propylene glycol monomethyl ether acetate solution. To the obtained solution, propylene glycol monoethyl ether was added to adjust the resultant solution to contain a solid residue in a proportion of 15% by weight at 140° C. while the solvent ratio of propylene glycol monomethyl ether acetate/propylene glycol monoethyl ether was 20/80. The obtained polymer (corresponding to Formula (F-6)) had a weight-average molecular weight measured by GPC of Mw 1,500 in terms of polystyrene.

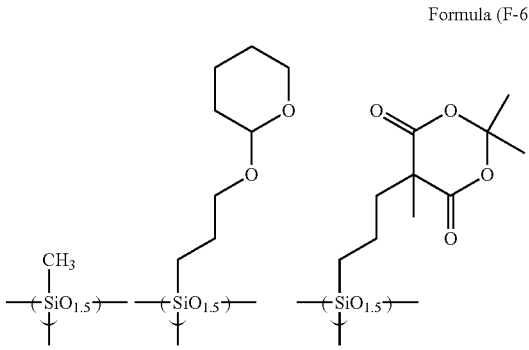

Formula (F-6)

(Preparation of Resist Underlayer Film)

The silicon-containing polymers obtained in Synthesis Examples 1 to 14, Comparative Synthesis Examples 1 to 7, and Additive Synthesis Examples 1 to 6 were each blended with an acid, a curing catalyst, an additive, a solvent, and water in ratios shown in Table 1. The resultant blend was filtered with a 0.1 μm fluorinated resin filter to prepare each of the solutions of the resist underlayer film forming compositions.

In Table 1, maleic acid is abbreviated as MA; (3-triethoxysilylpropyl)-4,5-dihydroimidazole is abbreviated as IMID-TEOS; triphenylsulfonium trifluoromethanesulfonate is abbreviated as TPS 105; monotriphenylsulfonium maleate is abbreviated as TPSMA; triphenylsulfonium camphorsulfonate is abbreviated as TPSCS; propylene glycol monomethyl ether acetate is abbreviated as PGMEA; and propylene glycol monoethyl ether is abbreviated as PGEE. As the water, ultrapure water was used. Each blending amount is expressed in parts by mass. The blending amount of the polymer is indicated not as the mass of the polymer solution, but as the mass of the polymer itself.

TABLE 1

| | Polymer | Acid | Curing catalyst | Additive | Solvent | | Water |
|---|---|---|---|---|---|---|---|
| Example 1 | Synthesis Example 1 | MA | IMIDTEOS | | PGMEA | PGEE | Water |
| (Parts by mass) | 2 | 0.06 | 0.012 | | 7 | 80 | 13 |
| Example 2 | Synthesis Example 1 | MA | TPSMA | | PGMEA | PGEE | Water |
| (Parts by mass) | 2 | 0.06 | 0.02 | | 7 | 80 | 13 |
| Example 3 | Synthesis Example 1 | MA | TPSCS | | PGMEA | PGEE | Water |
| (Parts by mass) | 2 | 0.06 | 0.02 | | 7 | 80 | 13 |
| Example 4 | Synthesis Example 1 | MA | IMIDTEOS | TPS105 | PGMEA | PGEE | Water |
| (Parts by mass) | 2 | 0.06 | 0.012 | 0.02 | 7 | 80 | 13 |
| Example 5 | Synthesis Example 2 | MA | IMIDTEOS | | PGMEA | PGEE | Water |
| (Parts by mass) | 2 | 0.06 | 0.012 | | 7 | 80 | 13 |
| Example 6 | Synthesis Example 3 | MA | IMIDTEOS | | PGMEA | PGEE | Water |
| (Parts by mass) | 2 | 0.06 | 0.012 | | 7 | 80 | 13 |
| Example 7 | Synthesis Example 3 | MA | TPSMA | | PGMEA | PGEE | Water |
| (Parts by mass) | 2 | 0.06 | 0.02 | | 7 | 80 | 13 |
| Example 8 | Synthesis Example 3 | MA | TPSCS | | PGMEA | PGEE | Water |
| (Parts by mass) | 2 | 0.06 | 0.02 | | 7 | 80 | 13 |
| Example 9 | Synthesis Example 3 | MA | IMIDTEOS | TPS105 | PGMEA | PGEE | Water |
| (Parts by mass) | 2 | 0.06 | 0.012 | 0.02 | 7 | 80 | 13 |
| Example 10 | Synthesis Example 4 | MA | TPSMA | | PGMEA | PGEE | Water |
| (Parts by mass) | 2 | 0.06 | 0.02 | | 7 | 80 | 13 |
| Example 11 | Synthesis Example 5 | MA | IMIDTEOS | | PGMEA | PGEE | Water |
| (Parts by mass) | 2 | 0.06 | 0.012 | | 7 | 80 | 13 |
| Example 12 | Synthesis Example 5 | MA | TPSMA | | PGMEA | PGEE | Water |
| (Parts by mass) | 2 | 0.06 | 0.02 | | 7 | 80 | 13 |
| Example 13 | Synthesis Example 5 | MA | TPSCS | | PGMEA | PGEE | Water |
| (Parts by mass) | 2 | 0.06 | 0.02 | | 7 | 80 | 13 |
| Example 14 | Synthesis Example 5 | MA | IMIDTEOS | TPS105 | PGMEA | PGEE | Water |
| (Parts by mass) | 2 | 0.06 | 0.012 | 0.02 | 7 | 80 | 13 |
| Example 15 | Synthesis Example 6 | MA | IMIDTEOS | | PGMEA | PGEE | Water |
| (Parts by mass) | 2 | 0.06 | 0.012 | | 7 | 80 | 13 |
| Example 16 | Synthesis Example 7 | MA | IMIDTEOS | | PGMEA | PGEE | Water |
| (Parts by mass) | 2 | 0.06 | 0.012 | | 7 | 80 | 13 |
| Example 17 | Synthesis Example 8 | MA | IMIDTEOS | | PGMEA | PGEE | Water |
| (Parts by mass) | 2 | 0.06 | 0.012 | | 7 | 80 | 13 |
| Example 18 | Synthesis Example 9 | MA | IMIDTEOS | | PGMEA | PGEE | Water |
| (Parts by mass) | 2 | 0.06 | 0.012 | | 7 | 80 | 13 |
| Example 19 | Synthesis Example 10 | MA | IMIDTEOS | | PGMEA | PGEE | Water |
| (Parts by mass) | 2 | 0.06 | 0.012 | | 7 | 80 | 13 |

TABLE 1-continued

| | Polymer | Acid | Curing catalyst | Additive | Solvent | | Water |
|---|---|---|---|---|---|---|---|
| Example 20 | Synthesis Example 11 | MA | IMIDTEOS | | PGMEA | PGEE | Water |
| (Parts by mass) | 2 | 0.06 | 0.012 | | 7 | 80 | 13 |
| Example 21 | Synthesis Example 11 | MA | IMIDTEOS | Additive 1 | PGMEA | PGEE | Water |
| (Parts by mass) | 2 | 0.06 | 0.012 | 0.05 | 7 | 80 | 13 |
| Example 22 | Synthesis Example 11 | MA | IMIDTEOS | Additive 2 | PGMEA | PGEE | Water |
| (Parts by mass) | 2 | 0.06 | 0.012 | 0.05 | 7 | 80 | 13 |
| Example 23 | Synthesis Example 11 | MA | IMIDTEOS | Additive 3 | PGMEA | PGEE | Water |
| (Parts by mass) | 2 | 0.06 | 0.012 | 0.05 | 7 | 80 | 13 |
| Example 24 | Synthesis Example 12 | MA | IMIDTEOS | Additive 1 | PGMEA | PGEE | Water |
| (Parts by mass) | 2 | 0.06 | 0.012 | 0.05 | 7 | 80 | 13 |
| Example 25 | Synthesis Example 12 | MA | IMIDTEOS | Additive 2 | PGMEA | PGEE | Water |
| (Parts by mass) | 2 | 0.06 | 0.012 | 0.05 | 7 | 80 | 13 |
| Example 26 | Synthesis Example 12 | MA | IMIDTEOS | Additive 3 | PGMEA | PGEE | Water |
| (Parts by mass) | 2 | 0.06 | 0.012 | 0.05 | 7 | 80 | 13 |
| Example 27 | Synthesis Example 11 | MA | IMIDTEOS | Additive 4 | PGMEA | PGEE | Water |
| (Parts by mass) | 2 | 0.06 | 0.012 | 0.05 | 7 | 80 | 13 |
| Example 28 | Synthesis Example 12 | MA | IMIDTEOS | Additive 5 | PGMEA | PGEE | Water |
| (Parts by mass) | 2 | 0.06 | 0.012 | 0.05 | 7 | 80 | 13 |
| Example 29 | Synthesis Example 12 | MA | IMIDTEOS | Additive 6 | PGMEA | PGEE | Water |
| (Parts by mass) | 2 | 0.06 | 0.012 | 0.05 | 7 | 80 | 13 |
| Example 30 | Synthesis Example 13 | MA | IMIDTEOS | | PGMEA | PGEE | Water |
| (Parts by mass) | 2 | 0.06 | 0.012 | | 7 | 80 | 13 |
| Example 31 | Synthesis Example 14 | MA | IMIDTEOS | | PGMEA | PGEE | Water |
| (Parts by mass) | 2 | 0.06 | 0.012 | | 7 | 80 | 13 |

TABLE 2

| | Polymer | Acid | Curing catalyst | Additive | Solvent | | Water |
|---|---|---|---|---|---|---|---|
| Comparative Example 1 | Comparative Synthesis Example 1 | MA | IMIDTEOS | | PGMEA | PGEE | Water |
| (Parts by mass) | 2 | 0.06 | 0.012 | | 7 | 80 | 13 |
| Comparative Example 2 | Comparative Synthesis Example 2 | MA | IMIDTEOS | | PGMEA | PGEE | Water |
| (Parts by mass) | 2 | 0.06 | 0.012 | | 7 | 80 | 13 |
| Comparative Example 3 | Comparative Synthesis Example 3 | MA | IMIDTEOS | | PGMEA | PGEE | Water |
| (Parts by mass) | 2 | 0.06 | 0.012 | | 7 | 80 | 13 |
| Comparative Example 4 | Comparative Synthesis Example 4 | MA | IMIDTEOS | | PGMEA | PGEE | Water |
| (Parts by mass) | 2 | 0.02 | 0.006 | | 7 | 80 | 13 |

TABLE 2-continued

| | Polymer | Acid | Curing catalyst | Additive | Solvent | | Water |
|---|---|---|---|---|---|---|---|
| Comparative Example 5 | Comparative Synthesis Example 5 | MA | IMIDTEOS | | PGMEA | PGEE | Water |
| (Parts by mass) | 2 | 0.02 | 0.006 | | 7 | 80 | 13 |
| Comparative Example 6 | Comparative Synthesis Example 6 | MA | IMIDTEOS | | PGMEA | PGEE | Water |
| (Parts by mass) | 2 | 0.02 | 0.006 | | 7 | 80 | 13 |
| Comparative Example 7 | Comparative Synthesis Example 7 | MA | IMIDTEOS | | PGMEA | PGEE | Water |
| (Parts by mass) | 2 | 0.02 | 0.006 | | 7 | 80 | 13 |

(Measurement of Optical Constants)

The Si-containing resist underlayer film forming compositions prepared in Examples 1 to 31 and Comparative Examples 1 to 7 were each applied onto a silicon wafer using a spinner. The composition was heated on a hot plate at 200° C. for 1 minute to form a Si-containing resist underlayer film (film thickness: 0.05 μm). Then, the refractive index (n value) and the optical absorptivity (k value; also called the attenuation coefficient) at a wavelength of 193 nm of the resist underlayer film were measured using a spectro-ellipsometer (VUV-VASEVU-302; manufactured by J. A. Woollam Co., Inc.).

(Measurement of Dry Etching Rate)

Etchers and etching gases used in the measurement of dry etching rates were as follows:
ES401 (manufactured by Nippon Scientific Co., Ltd.): $CF_4$
RIE-10NR (manufactured by Samco, Inc.): $O_2$.

The solutions of the Si-containing resist underlayer film forming compositions prepared in Examples 1 to 31 and Comparative Examples 1 to 7 were each applied onto a silicon wafer using a spinner. The solutions were heated on a hot plate at 240° C. for 1 minute to form Si-containing resist underlayer films (film thickness: 0.08 μm (for measurement of etching rate with $CF_4$ gas), and 0.05 μm (for measurement of etching rate with $O_2$ gas)). In a similar manner, an organic underlayer film forming composition was applied onto a silicon wafer using a spinner to form a coating film (film thickness: 0.20 μm) thereon. By using $O_2$ gas as the etching gas, the dry etching rate of the organic underlayer film was measured and compared with the dry etching rates of the Si-containing resist underlayer films of Examples 1 to 31 and Comparative Examples 1 to 7.

TABLE 3

| | Refractive index | Optical Absorption coefficient | Etching rate with fluorine-based gas | Oxygen-based gas resistance |
|---|---|---|---|---|
| Example 1 | 1.68 | 0.20 | 21 | 0.03 |
| Example 2 | 1.67 | 0.21 | 21 | 0.03 |
| Example 3 | 1.67 | 0.21 | 21 | 0.03 |
| Example 4 | 1.67 | 0.21 | 21 | 0.03 |
| Example 5 | 1.63 | 0.30 | 23 | 0.03 |
| Example 6 | 1.62 | 0.11 | 21 | 0.02 |
| Example 7 | 1.61 | 0.11 | 21 | 0.02 |
| Example 8 | 1.61 | 0.11 | 21 | 0.02 |
| Example 9 | 1.61 | 0.11 | 21 | 0.02 |
| Example 10 | 1.67 | 0.10 | 24 | 0.02 |

TABLE 3-continued

| | Refractive index | Optical Absorption coefficient | Etching rate with fluorine-based gas | Oxygen-based gas resistance |
|---|---|---|---|---|
| Example 11 | 1.63 | 0.30 | 23 | 0.03 |
| Example 12 | 1.62 | 0.31 | 23 | 0.03 |
| Example 13 | 1.62 | 0.31 | 23 | 0.03 |
| Example 14 | 1.62 | 0.31 | 23 | 0.03 |
| Example 15 | 1.68 | 0.20 | 21 | 0.03 |
| Example 16 | 1.66 | 0.21 | 21 | 0.03 |
| Example 17 | 1.64 | 0.27 | 21 | 0.03 |
| Example 18 | 1.54 | 0.16 | 21 | 0.02 |
| Example 19 | 1.68 | 0.20 | 21 | 0.03 |
| Example 20 | 1.64 | 0.11 | 22 | 0.02 |
| Example 21 | 1.65 | 0.11 | 22 | 0.02 |
| Example 22 | 1.65 | 0.11 | 24 | 0.02 |
| Example 23 | 1.64 | 0.11 | 23 | 0.02 |
| Example 24 | 1.64 | 0.11 | 22 | 0.02 |
| Example 25 | 1.64 | 0.12 | 22 | 0.02 |
| Example 26 | 1.64 | 0.11 | 22 | 0.02 |
| Example 27 | 1.64 | 0.13 | 22 | 0.02 |
| Example 28 | 1.64 | 0.11 | 22 | 0.03 |
| Example 29 | 1.64 | 0.11 | 22 | 0.02 |
| Example 30 | 1.67 | 0.25 | 23 | 0.03 |
| Example 31 | 1.70 | 0.23 | 23 | 0.03 |
| Comparative Example 1 | 1.69 | 0.23 | 22 | 0.02 |
| Comparative Example 2 | 1.62 | 0.12 | 20 | 0.02 |
| Comparative Example 3 | 1.67 | 0.10 | 24 | 0.03 |
| Comparative Example 4 | 1.84 | 0.70 | 21 | 0.05 |
| Comparative Example 5 | 1.80 | 0.81 | 22 | 0.05 |
| Comparative Example 6 | 1.92 | 0.76 | 23 | 0.06 |
| Comparative Example 7 | 1.82 | 0.75 | 22 | 0.05 |

(Preparation of Organic Resist Underlayer Film A)

In nitrogen, into a 100 mL four-neck flask, carbazole (6.69 g, 0.040 mol, manufactured by Tokyo Chemical Industry Co., Ltd.), 9-fluorenone (7.28 g, 0.040 mol, manufactured by Tokyo Chemical Industry Co., Ltd.), and p-toluenesulfonic acid monohydrate (0.76 g, 0.0040 mol, manufactured by Tokyo Chemical Industry Co., Ltd.) were charged and thereto, 1,4-dioxane (6.69 g, manufactured by Kanto Chemical Co., Inc.) was added, followed by stirring the resultant mixture. The temperature of the reaction mixture was elevated to 100° C. to dissolve the mixture and the polymerization was initiated. After 24 hours, the reaction mixture was left to be cooled down to 60° C., and then, to the reaction mixture, chloroform (34 g, manufactured by Kanto Chemical Co., Inc.) was added to dilute the reaction mixture, followed by reprecipitating the resultant reaction mixture in methanol (168 g, manufactured by Kanto Chemical Co., Inc.). The obtained precipitate was filtered and was dried using a vacuum drier at 80° C. for 24 hours to obtain 9.37 g of the objective polymer (corresponding to Formula (G-1), hereinafter abbreviated as PCzFL).

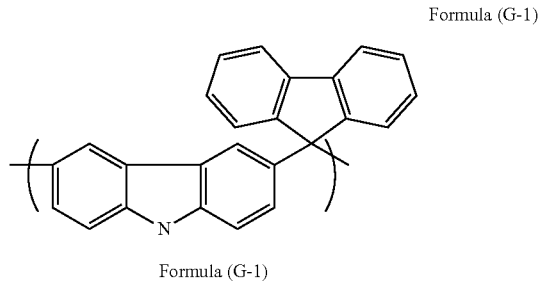

Formula (G-1)

The measurement result of $^1$H-NMR of PCzFL was as follows:

$^1$H-NMR (400 MHz, DMSO-$d_6$): δ7.03-7.55 (br, 12H), δ7.61-8.10 (br, 4H), δ11.18 (br, 1H).

PCzFL had a weight-average molecular weight Mw of 2,800 that was measured by GPC in terms of polystyrene, and a polydispersity Mw/Mn of 1.77.

With 20 g of the obtained resin, 3.0 g of tetramethoxymethyl glycoluril (trade name: POWDER LINK 1174; manufactured by Mitsui Cytec Ltd.) as a crosslinking agent, 0.30 g of pyridinium p-toluenesulfonate as a catalyst, and 0.06 g of MEGAFAC R-30 (trade name; manufactured by Dainippon Ink & Chemicals Inc.) as a surfactant were mixed. The resultant mixture was dissolved in 88 g of propylene glycol monomethyl ether acetate to prepare a solution. The solution was then filtered using a polyethylene microfilter having a pore diameter of 0.10 μM and was further filtered using a polyethylene microfilter having a pore diameter of 0.05 μm to prepare a solution of an organic resist underlayer film (layer A) forming composition to be used for a lithography process with a multilayer film.

(Resist Patterning Evaluation: Evaluation Through NTD Process in which Development is Performed with Organic Solvent)

The organic underlayer film (layer A) forming composition obtained by the above formula was applied onto a silicon wafer, and the composition was baked on a hot plate at 240° C. for 60 seconds to obtain an organic underlayer film (layer A) having a film thickness of 200 nm. The Si-containing resist underlayer film (layer B) forming compositions obtained in Examples 1 to 5 and 11 to 31 and Comparative Examples 1, 4 to 7 were each applied onto the organic underlayer film (layer A). The composition was baked on a hot plate at 240° C. for 60 seconds to obtain a Si-containing resist underlayer film (layer B). The Si-containing resist underlayer film (layer B) had a film thickness of 35 nm.

Onto each of the layers B, a commercially available photoresist solution (trade name. FAiRS-9521NT05; manufactured by FUJIFILM Corporation) was applied by a spinner and the solution was heated on a hot plate at 100° C. for 1 minute to form a photoresist film (layer C) having a film thickness of 85 nm.

Using an NSR-S307E scanner (manufactured by Nikon Corporation (wavelength: 193 nm, NA, σ: 0.85, 0.93/0.85), exposure was performed through a mask set to form a photoresist after the development having a line width and a width between lines of 0.060 μm each, that is, 0.060 μm-dense line and space (L/S)=1/2, and through a mask set to form a photoresist after the development having a line width and a width between lines of 0.058 μm each, that is, 0.058 μm-dense line and space (L/S)=1/1. Then, the resist pattern was baked on a hot plate at 100° C. for 60 seconds, was cooled down, and was developed using butyl acetate (solvent developer) for 60 seconds to form a negative-type pattern on the resist underlayer film (layer B). With respect to the obtained photoresist patterns, a photoresist pattern in which no large pattern peeling, no undercut, or no widening (footing) at a line bottom occurred was evaluated as good.

In Table 4, the results of observing a skirt shape of the resist after the lithography evaluation are shown.

TABLE 4

| | Pattern width and interval 1/1 | Pattern width and interval 1/2 |
|---|---|---|
| Example 1 | Good | Good |
| Example 2 | Good | Good |
| Example 3 | Good | Good |
| Example 4 | Good | Good |
| Example 5 | Good | Good |
| Example 11 | Good | Good |
| Example 12 | Good | Good |
| Example 13 | Good | Good |
| Example 14 | Good | Good |
| Example 15 | Good | Good |
| Example 16 | Good | Good |
| Example 17 | Good | Good |
| Example 18 | Good | Good |
| Example 19 | Good | Good |
| Example 20 | Good | Good |
| Example 21 | Good | Good |
| Example 22 | Good | Good |
| Example 23 | Good | Good |
| Example 24 | Good | Good |
| Example 25 | Good | Good |
| Example 26 | Good | Good |
| Example 27 | Good | Good |
| Example 28 | Good | Good |
| Example 29 | Good | Good |
| Example 30 | Good | Good |
| Example 31 | Good | Good |
| Comparative Example 1 | Good (partial peeling) | Poor (large peeling) |
| Comparative Example 4 | Poor (large peeling) | Poor (large peeling) |
| Comparative Example 5 | Poor (large peeling) | Poor (large peeling) |
| Comparative Example 6 | Poor (large peeling) | Poor (large peeling) |
| Comparative Example 7 | Poor (large peeling) | Poor (large peeling) |

(Resist Patterning Evaluation: Evaluation Via PTD Process of Performing Development with Alkaline Developer)

The organic underlayer film (layer A) forming composition obtained by the above formula was applied onto a silicon wafer, and the applied composition was baked on a hot plate at 240° C. for 60 seconds to obtain an organic underlayer film (layer A) having a film thickness of 200 nm. The Si-containing resist underlayer film (layer B) forming compositions obtained in Examples 6 to 10 and Comparative Examples 2 to 7 were each applied onto the organic underlayer film (layers A). The applied composition was baked on a hot plate at 240° C. for 60 seconds to obtain a Si-containing resist underlayer film (layer B). The Si-containing resist underlayer films (layers B) had a film thickness of 35 nm Onto each of the layers B, a commercially available photoresist solution (trade name: AR 2772; manufactured by JSR Corporation) was applied by a spinner, and the applied solution was baked on a hot plate at 110° C. for 60 seconds to form a photoresist film (layer C)

having a film thickness of 120 nm. The patterning of the resist was performed using an ArF exposing machine S-307E, manufactured by Nikon Corporation (wavelength: 193 nm, NA, σ: 0.85, 0.93/0.85 (Dipole), immersion liquid: water). The target was a photoresist after the development having a line width and a width between lines of 0.065 μm each, which is what is called lines and spaces (dense lines), and the exposure was performed through a mask set to form such a photoresist.

Then, the resultant product was baked on a hot plate at 110° C. for 60 seconds, was cooled down, and was developed with a tetramethylammonium hydroxide aqueous solution (developer) having a concentration of 2.38% by mass in a 60-second single paddle process. With respect to the obtained photoresist patterns, a photoresist pattern in which no large pattern peeling, no undercut, or no widening (footing) at a line bottom occurred was evaluated as good.

Table 5 lists the results of observing a skirt shape of the resist after the lithography evaluation.

TABLE 5

Skirt shape of the resist after the lithography evaluation

| | |
|---|---|
| Example 6 | Good |
| Example 7 | Good |
| Example 8 | Good |
| Example 9 | Good |
| Example 10 | Good |
| Comparative Example 2 | Footing |
| Comparative Example 3 | Footing |
| Comparative Example 4 | Poor (large peeling) |
| Comparative Example 5 | Poor (large peeling) |
| Comparative Example 6 | Poor (large peeling) |
| Comparative Example 7 | Poor (large peeling) |

INDUSTRIAL APPLICABILITY

A resist underlayer film forming composition for lithography usable for the production of semiconductor devices is provided. A resist underlayer film forming composition for lithography for forming a resist underlayer film usable as a hardmask is provided. Further, a resist underlayer film forming composition for lithography for forming a resist underlayer film usable as an anti-reflective coating is provided.

The invention claimed is:

1. A resist underlayer film forming composition, comprising: a hydrolysis product of a hydrolyzable silane of Formula (1) and a hydrolyzable silane of Formula (2) and a hydrolyzable silane of Formula (4), as a polymer, where Formula (1) is:

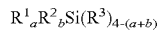   Formula (1)

where in Formula (1),

R$^1$ is an organic group containing Formula (1-1), Formula (1-2), or Formula (1.3), and is bonded to a silicon atom through a Si—C bond, where Formula (A-1), Formula (A-2), and Formula (A-3) are:

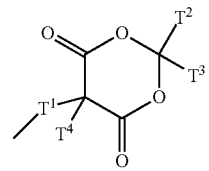   Formula (1-1)

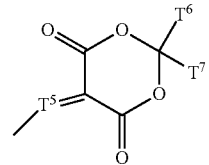   Formula (1-2)

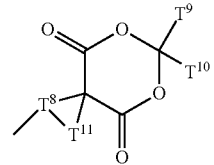   Formula (1-3)

in Formula (1-1), Formula (1-2), and Formula (1-3), T$^1$ is an alkylene group, a cyclic alkylene group, an alkenylene group, an arylene group, a sulfur atom, an oxygen atom, an oxycarbonyl group, an amido group, a secondary amino group, or a combination of these groups and atoms; T$^5$ is an alkylidyne group, a sulfur atom, an amido group, a tertiary amino group, or a combination of these groups and atom; T$^8$ is an alkanetriyl group, a sulfur atom, an amido, group a tertiary amino group, or a combination of these groups and atom; each of T$^2$, T$^3$, T$^4$, T$^6$, T$^7$, T$^9$, and T$^{10}$ is independently a hydrogen atom, an alkyl group, an alkenyl group, or a hydrolyzable silyl group bonded optionally through an alkylene group; and T$^{11}$ is an alkylene group;

R$^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond;

R$^3$ is an alkoxy group, an acyloxy group, or a halogen group; and a is an integer of 1 and b is an integer of 0 to 2, where a+b is an integer of 1 to 3;

Formula (2) is:

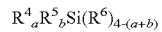   Formula (2)

where in Formula (2),

R$^4$ is an organic group containing Formula (2-1), Formula (2-2), or Formula (2-3):

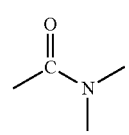   Formula (2-1)

   Formula (2-2)

-continued

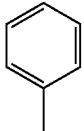
Formula (2-3)

and is bonded to a silicon atom through a Si—C bond:
$R^5$ is an alkyl group, aryl group, a halogenated alkyl group, a halogenated aryl group, an alkenyl group, or an organic group, having an epoxy group, an acryloyl group, a methacryloyl group, a mercapto group, an amino group, or a cyano group and is bonded to a silicon atom through a Si—C bond;
$R^6$ is an alkoxy group, an acyloxy group, or halogen group; and
a is an integer of 1 and b is an integer of 0 to 2, where a+b is an integer of 1 to 3; and
Formula (4) is:

Formula (4)

where
in Formula (4), $R^{10}$ is an alkyl group, an aryl group, a halogenated alkyl group, a halogenated aryl group, an alkenyl group, or an organic group having an epoxy group, an acryloyl group, a methacryloyl group, a mercapto group, or a cyano group and is bonded to a silicon atom through a Si—C bond; $R^{11}$ is an alkoxy group, an acyloxy group, or a halogen group; and $a_1$ is an integer of 0 to 3.

2. The resist underlayer film forming composition of claim 1, wherein the polymer hydrolysis product further comprises a hydrolyzable silane of Formula (3) where Formula (3) is:

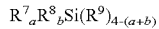
Formula (3)

where
in Formula (3), $R^7$ is an organic group containing Formula (3-1), Formula (3-2), Formula (3-3), Formula (3-4), Formula (3-5), or Formula (3-6):

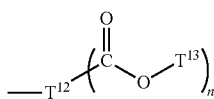
Formula (3-1)

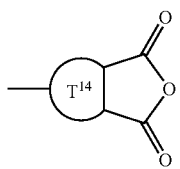
Formula (3-2)

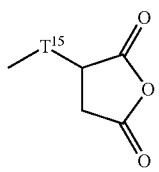
Formula (3-3)

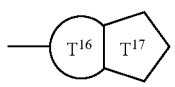
Formula (3-4)

-continued

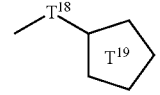
Formula (3-5)

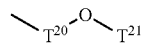
Formula (3-6)

in Formula (3-1), Formula (3-2), Formula (3-3), Formula (3-4), Formula (3-5), and Formula (3-6), each of $T^{12}$, $T^{15}$, $T^{18}$, and $T^{20}$ is an alkylene group, a cyclic alkylene group, an alkenylene group, an arylene group, a sulfur atom, an oxygen atom, an oxycarbonyl group, an amido group, a secondary amino group, or a combination of these groups or atoms; $T^{13}$ is an alkyl group; each of $T^{14}$ and $T^{16}$ is an aliphatic ring or an aromatic ring; each of $T^{17}$ and $T^{19}$ is a lactone ring; $T^{21}$ is a $C_{1-10}$ alkyl group, a $C_{6-20}$ aryl group, a $C_{2-10}$ alkenyl group, or a group containing a $C_{1-10}$ alkylene group, a $C_{6-20}$ arylene group, an ether group, an ester group, a sulfide group, a carbonyl group, or a combination of these groups; and n is an integer of 1 or 2), and is bonded to a silicon atom through a Si—C bond; $R^8$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond; $R^9$ is an alkoxy group, an acyloxy group, or a halogen group; and a is an integer of 1 and b is an integer of 0 to 2, where a+b is an integer of 1 to 3.

3. A silane compound of Formula (A):

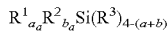
Formula (A)

where
in Formula (A),
$R^1$ is an organic group containing Formula (A-1), Formula (A-2), or Formula (A-3) and is bonded to a silicon atom through a Si—C bond, where Formula (A-1), Formula (A-2), and Formula (A-3) are:

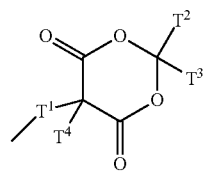
Formula (A-1)

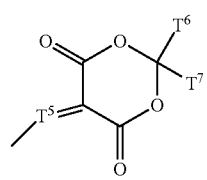
Formula (A-2)

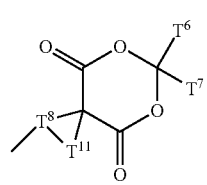
Formula (A-3)

in Formula (A-1), Formula (A-2), or Formula (A-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups or atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is independently a hydrogen atom, an alkyl group, an alkenyl group, or a hydrolyzable silyl group bonded optionally through an alkylene group; and $T^{11}$ is an alkylene group;

$R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond;

$R^3$ is an alkoxy group, an acyloxy group, or a halogen group;

$a_a$ is an integer of 1 and $b_a$ is an integer of 0 or 1, where $a_a+b_a$ is an integer of 1 or 2.

4. A resist underlayer film forming composition for lithography, comprising:

as a silane, a hydrolyzable silane, a hydrolysis product of the hydrolyzable silane, or a hydrolysis-condensation product of the hydrolyzable silane, wherein the hydrolyzable silane includes:

a hydrolyzable silane of Formula (1) or a hydrolyzable silane containing a combination of a hydrolyzable silane of Formula (1) with a hydrolyzable silane of Formula (2); wherein a content of:

the hydrolyzable silane of Formula (1) or the hydrolyzable silane containing the combination of the hydrolyzable silane of Formula (1) with the hydrolyzable silane of Formula (2), is less than 50% by mole with respect to all silanes in the resist underlayer film forming composition; in which Formula (1):

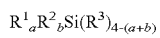   Formula (1)

where in Formula (1), $R^1$ is an organic group containing Formula (1-1), Formula (1-2), or Formula (1-3), and is bonded to a silicon atom through a Si—C bond, where Formula (A-1), Formula (A-2), and Formula (A-3) are:

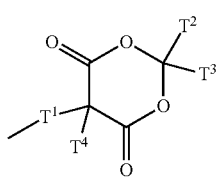   Formula (1-1)

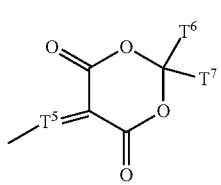   Formula (1-2)

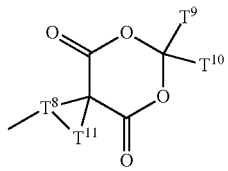   Formula (1-3)

in Formula (1-1), Formula (1-2), and Formula (1-3), $T^1$ is an alkylene group, a cyclic alkylene group, an alkenylene group, an arylene group, a sulfur atom, an oxygen atom, an oxycarbonyl group, an amido group, a secondary amino group, or a combination of these groups and atoms; $T^5$ is an alkylidyne group, a sulfur atom, an amido group, a tertiary amino group, or a combination of these groups and atom; $T^8$ is an alkanetriyl group, a sulfur atom, an amido group, a tertiary amino group, or a combination of these groups and atom; each of $T^2$, $T^3$, $T^4$, $T^6$, $T^7$, $T^9$, and $T^{10}$ is independently a hydrogen atom, an alkyl group, an alkenyl group, or a hydrolyzable silyl group bonded optionally through an alkylene group; and $T^{11}$ is an alkylene group;

$R^2$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond;

$R^3$ is an alkoxy group, an acyloxy group, or a halogen group; and a is an integer of 1 and b is an integer of 0 to 2, where a+b is an integer of 1 to 3; and Formula (2):

   Formula (2)

where in Formula (2), $R^4$ is an organic group containing Formula (2-1), Formula (2-2), or Formula (2-3):

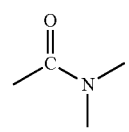   Formula (2-1)

   Formula (2-2)

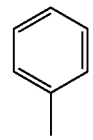   Formula (2-3)

and is bonded to a silicon atom through a Si—C bond;

$R^5$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond;

$R^6$ is an alkoxy group, an acyloxy group, or a halogen group; and a is an integer of 1 and b is an integer of 0 to 2, where a+b is an integer of 1 to 3.

5. The resist underlayer film forming composition according to claim 4, wherein the content of the hydrolyzable silane of Formula (1) or the hydrolyzable silane containing a combination of a hydrolyzable silane of Formula (1) with a hydrolyzable silane of Formula (2)

is 5 to 45% by mole with respect to all silanes in the resist underlayer film forming composition.

6. The resist underlayer film forming composition according to claim 4, wherein the hydrolyzable silane of Formula (2) is a hydrolyzable silane in which $R^4$ is an organic group containing a group of Formula (2-1), a hydrolyzable silane in which $R^4$ is an organic group containing a group of Formula (2-2), a hydrolyzable silane in which $R^4$ is an organic group containing a group of Formula (2-3), or a mixture of these hydrolyzable silanes.

7. The resist underlayer film forming composition according to claim 4, wherein the hydrolyzable silane containing a combination of a hydrolyzable silane of Formula (1) with a hydrolyzable silane of Formula (2) contains the hydrolyzable silane of Formula (1) and the hydrolyzable silane of Formula (2) in a molar ratio of 1.0:0.01 to 10.

8. The resist underlayer film forming composition for lithography according to claim 4, wherein the hydrolyzable silane contains a hydrolyzable silane of Formula (1) or a hydrolyzable silane containing a combination of a hydrolyzable silane of Formula (1) with a hydrolyzable silane of Formula (2), and further comprises a hydrolyzable silane of Formula (3):

$$R^7_a R^8_b Si(R^9)_{4-(a+b)} \quad \text{Formula (3)}$$

where in Formula (3), $R^7$ is an organic group containing Formula (3-1), Formula (3-2), Formula (3-3), Formula (3-4), Formula (3-5), or Formula (3-6), and is bonded to a silicon atom through a Si—C bond, where

Formula (3-1)

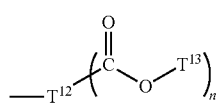
Formula (3-2)

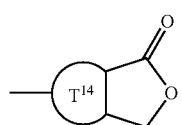
Formula (3-3)

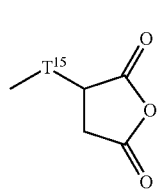
Formula (3-4)

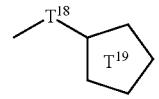
Formula (3-5)

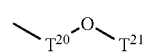
Formula (3-6)

in Formula (3-1), Formula (3-2), Formula (3-3), Formula (3-4), Formula (3-5), and Formula (3-6), each of $T^{12}$, $T^{15}$, $T^{18}$, and $T^{20}$ is an alkylene group, a cyclic alkylene group, an alkenylene group, an arylene group, a sulfur atom, an oxygen atom, an oxycarbonyl group, an amido group, a secondary amino group, or a combination of these groups or atoms; $T^{13}$ is an alkyl group; each of $T^{14}$ and $T^{16}$ is an aliphatic ring or an aromatic ring; each of $T^{17}$ and $T^{19}$ is a lactone ring; $T^{21}$ is a $C_{1-10}$ alkyl group, a $C_{6-20}$ aryl group, a $C_{2-10}$ alkenyl group, or a group containing a $C_{1-10}$ alkylene group, a $C_{6-20}$ arylene group, man ether group, man ester group, a sulfide group, a carbonyl group, or a combination of these groups; and n is an integer of 1 or 2);

$R^8$ is an alkyl group, an aryl group, a halogenated alkyl group, a halogenated aryl group, an alkenyl group, or an organic group having an epoxy group, an acryloyl group, a methacryloyl group, a mercapto group, an amino group, or a cyano group and is bonded to a silicon atom through a Si—C bond;

$R^9$ is an alkoxy group, an acyloxy group, or a halogen group; and a is an integer of 1 and b is an integer of 0 to 2, where a+b is an integer of 1 to 3.

9. The resist underlayer film forming composition according to claim 8, comprising the hydrolyzable silane of Formula (1) and the hydrolyzable silane of Formula (2) and the hydrolyzable silane of Formula (3) in a molar ratio of 1.0 to 10:0.01 to 10.

10. The resist underlayer film forming composition for lithography according to claim 8, wherein the hydrolyzable silane contains the hydrolyzable silane of Formula (1), the combination of a hydrolyzable silane of Formula (1) with a hydrolyzable silane of Formula (2), a combination of a hydrolyzable silane of Formula (1) with a hydrolyzable silane of Formula (3), or a combination of a hydrolyzable silane of Formula (1) and a hydrolyzable silane of Formula (2) and a hydrolyzable silane of Formula (3), and a further hydrolyzable silane, and the further hydrolyzable silane being at least one organic silicon compound selected from the group consisting of Formula (4) and Formula (5):

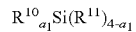
Formula (4)

where in Formula (4), $R^{10}$ is an alkyl group, an aryl group, a halogenated alkyl group, a halogenated aryl group, an alkenyl group, or an organic group having an epoxy group, an acryloyl group, a methacryloyl group, a mercapto group, or a cyano group and is bonded to a silicon atom through a Si—C bond; $R^{11}$ is an alkoxy group, an acyloxy group, or a halogen group; and $a_1$ is an integer of 0 to 3,

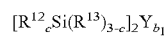
Formula (5)

where in Formula (5), $R^{12}$ is an alkyl group and is bonded to a silicon atom through a Si—C bond; $R^{13}$ is an alkoxy group, an acyloxy group, or a halogen group; Y is an alkylene group or an arylene group; $b_1$ is an integer of 0 or 1; and c is an integer of 0 or 1.

11. The resist underlayer film forming composition according to claim 4, further comprising an acid as a hydrolysis catalyst.

12. The resist underlayer film forming composition according to claim 4, further comprising water.

13. A resist underlayer film obtained by applying the resist underlayer film forming composition according to claim 4 onto a semiconductor substrate and baking the composition.

14. A method for producing a semiconductor device, the method comprising:
  applying the resist underlayer film forming composition according to claim 4 onto a semiconductor substrate and baking the composition to form a resist underlayer film;
  applying a composition for a resist onto the underlayer film to form a resist film;
  exposing the resist film to light;
  developing the resist after the exposure to obtain a resist pattern;
  etching the resist underlayer film using the resist pattern; and
  processing the semiconductor substrate using the patterned resist and the patterned resist underlayer film.

15. A method for producing a semiconductor device, the method comprising:
  forming an organic underlayer film on a semiconductor substrate;
  applying the resist underlayer film forming composition according to claim 4 onto the organic underlayer film and baking the composition to form a resist underlayer film;
  applying a composition for a resist onto the resist underlayer film to form a resist film;
  exposing the resist film to light;
  developing the resist after the exposure to obtain a resist pattern;
  etching the resist underlayer film using the resist pattern;
  etching the organic underlayer film using the patterned resist underlayer film; and
  processing the semiconductor substrate using the patterned organic underlayer film.

* * * * *